United States Patent
Haber et al.

(10) Patent No.: US 10,596,162 B2
(45) Date of Patent: *Mar. 24, 2020

(54) METHOD FOR TREATING GEFITINIB RESISTANT CANCER

(71) Applicants: WYETH LLC, New York, NY (US); The General Hospital Corporation, Boston, MA (US)

(72) Inventors: Daniel A. Haber, Chestnut Hill, MA (US); Daphne Winifred Bell, Chevy Chase, MD (US); Jeffrey E. Settleman, Newton, MA (US); Raffaella Sordella, Cold Spring Harbor, NY (US); Nadia G. Godin-Heymann, Middlesex (GB); Eunice L. Kwak, Marlborough, MA (US); Sridhar Krishna Rabindran, Eagleville, PA (US)

(73) Assignees: Wyeth LLC, New York, NY (US); The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/207,349

(22) Filed: Jul. 11, 2016

(65) Prior Publication Data

US 2016/0310482 A1    Oct. 27, 2016

Related U.S. Application Data

(63) Continuation of application No. 11/883,474, filed as application No. PCT/US2006/003717 on Feb. 2, 2006.

(60) Provisional application No. 60/671,989, filed on Apr. 15, 2005, provisional application No. 60/649,483, filed on Feb. 3, 2005.

(51) Int. Cl.
*A61K 31/4709* (2006.01)
*A61K 31/4706* (2006.01)
*A61K 38/17* (2006.01)

(52) U.S. Cl.
CPC ...... *A61K 31/4709* (2013.01); *A61K 31/4706* (2013.01); *A61K 38/17* (2013.01)

(58) Field of Classification Search
None
See application file for complete search history.

(56) References Cited

U.S. PATENT DOCUMENTS

| | | | |
|---|---|---|---|
| 4,966,891 A | 10/1990 | Fujiu et al. | |
| 5,362,718 A | 11/1994 | Skotnicki et al. | |
| 5,453,497 A | 9/1995 | Kamiya et al. | |
| 5,472,949 A | 12/1995 | Arasaki et al. | |
| 5,476,932 A | 12/1995 | Brinkman et al. | |
| 5,715,151 A | 2/1998 | Moriura | |
| 5,760,041 A | 6/1998 | Wissner et al. | |
| 6,002,008 A | 12/1999 | Wissner et al. | |
| 6,143,764 A | 11/2000 | Kubo et al. | |
| 6,251,912 B1 | 6/2001 | Wissner et al. | |
| 6,277,983 B1 | 8/2001 | Shaw et al. | |
| 6,288,082 B1 | 9/2001 | Wissner et al. | |
| 6,297,258 B1 | 10/2001 | Wissner et al. | |
| 6,384,051 B1 | 5/2002 | Frost et al. | |
| 6,387,371 B1 | 5/2002 | Hudziak et al. | |
| 6,399,063 B1 | 6/2002 | Hudziak et al. | |
| 6,432,979 B1 | 8/2002 | Frost et al. | |
| 6,511,986 B2 | 1/2003 | Zhang et al. | |
| 6,617,333 B2 | 9/2003 | Rabindran et al. | |
| 6,780,996 B2 | 8/2004 | Boschelli et al. | |
| 6,821,515 B1 | 11/2004 | Cleland et al. | |
| 6,821,988 B2 | 11/2004 | Wissner et al. | |
| 7,026,330 B2 | 4/2006 | Grupp et al. | |
| 7,091,213 B2 | 8/2006 | Metcalf et al. | |
| 7,126,025 B2 | 10/2006 | Considine et al. | |
| 7,189,735 B2 | 3/2007 | Dukart et al. | |
| 7,235,564 B2 | 6/2007 | Scott et al. | |
| 7,294,468 B2 | 11/2007 | Bell et al. | |
| 7,297,795 B2 | 11/2007 | Sutherland et al. | |
| 7,306,801 B2 | 12/2007 | Caligiuri et al. | |
| RE40,418 E | 7/2008 | Rabindran et al. | |
| 7,399,865 B2 | 7/2008 | Wissner et al. | |
| 7,846,936 B2 | 12/2010 | Hilberg et al. | |
| 7,897,159 B2 | 3/2011 | Weber | |
| 7,915,402 B2 | 3/2011 | Anderson et al. | |

(Continued)

FOREIGN PATENT DOCUMENTS

CN    1437942 A    8/2003
CN    101185633 A    5/2008

(Continued)

OTHER PUBLICATIONS

Wissner et al. (J. Med. Chem. 2003, 46:49-63).*

(Continued)

*Primary Examiner* — Peter J Reddig
(74) *Attorney, Agent, or Firm* — Jones Day

(57) ABSTRACT

The present invention is directed to methods for the treatment of gefitinib and/or erlotinib resistant cancer. An individual with cancer is monitored for cancer progression following treatment with gefitinib and/or erlotinib. Progression of the cancer is indicative that the cancer is resistant to gefitinib and/or erlotinib. Once progression of cancer is noted, the subject is administered a pharmaceutical composition comprising an irreversible epidermal growth factor receptor (EGFR) inhibitor. In preferred embodiments, the irreversible EGFR inhibitor is EKB 569, HKI-272 and HKI-357.

4 Claims, 12 Drawing Sheets

Specification includes a Sequence Listing.

(56) References Cited

U.S. PATENT DOCUMENTS

| | | |
|---|---|---|
| 7,943,778 B2 | 5/2011 | Jiang et al. |
| 7,964,349 B2 | 6/2011 | Bell et al. |
| 7,982,043 B2 | 7/2011 | Wissner et al. |
| 8,022,216 B2 | 9/2011 | Lu et al. |
| 8,105,769 B2 | 1/2012 | Bell et al. |
| 8,173,814 B2 | 5/2012 | Lu et al. |
| 8,173,817 B2 | 5/2012 | Reddy et al. |
| 8,338,456 B2 | 12/2012 | Coughlin et al. |
| 8,394,959 B2 | 3/2013 | Lu et al. |
| 8,465,916 B2 | 6/2013 | Bell et al. |
| 8,518,446 B2 | 8/2013 | Asraf et al. |
| 8,524,281 B2 | 9/2013 | Venkata Raman Rao et al. |
| 8,669,273 B2 | 3/2014 | Zacharchuk et al. |
| 8,790,708 B2 | 7/2014 | Asraf et al. |
| 9,139,558 B2 | 9/2015 | Lu et al. |
| 9,511,063 B2 | 12/2016 | Zacharchuk |
| 9,630,946 B2 | 4/2017 | Lu et al. |
| 2002/0002162 A1 | 1/2002 | Lee |
| 2002/0183239 A1 | 12/2002 | Gibbons, Jr. et al. |
| 2002/0183240 A1 | 12/2002 | Gibbons et al. |
| 2002/0198137 A1 | 12/2002 | Dukart et al. |
| 2002/0198317 A1 | 12/2002 | Dukart et al. |
| 2003/0144252 A1 | 7/2003 | Furr |
| 2003/0149056 A1 | 8/2003 | Wissner et al. |
| 2003/0153593 A1 | 8/2003 | Dukart et al. |
| 2004/0039010 A1 | 2/2004 | Grupp et al. |
| 2004/0096436 A1 | 5/2004 | Carson et al. |
| 2004/0162442 A1 | 8/2004 | Considine et al. |
| 2004/0176339 A1 | 9/2004 | Sherman et al. |
| 2004/0209930 A1 | 10/2004 | Carboni et al. |
| 2004/0258662 A1 | 12/2004 | Gibbons et al. |
| 2005/0025825 A1 | 2/2005 | Heasley et al. |
| 2005/0032825 A1 | 2/2005 | Metcalf et al. |
| 2005/0038080 A1 | 2/2005 | Boyer et al. |
| 2005/0043233 A1 | 2/2005 | Stefanic et al. |
| 2005/0059678 A1 | 3/2005 | Wissner et al. |
| 2005/0129761 A1 | 6/2005 | Venkata Ramana Rao et al. |
| 2005/0136063 A1 | 6/2005 | Wang et al. |
| 2005/0187184 A1 | 8/2005 | Gibbons, Jr. et al. |
| 2005/0272083 A1 | 12/2005 | Seshagiri |
| 2005/0272758 A1 | 12/2005 | Bayever et al. |
| 2006/0030547 A1 | 2/2006 | Dukart et al. |
| 2006/0035904 A1 | 2/2006 | Gibbons et al. |
| 2006/0058311 A1 | 3/2006 | Munzert et al. |
| 2006/0079515 A1 | 4/2006 | Frost |
| 2006/0084666 A1 | 4/2006 | Harari et al. |
| 2006/0094674 A1 | 5/2006 | Neel et al. |
| 2006/0128793 A1 | 6/2006 | Zask et al. |
| 2006/0147959 A1 | 7/2006 | Bell et al. |
| 2006/0178387 A1 | 8/2006 | Fujimoto et al. |
| 2006/0235046 A1 | 10/2006 | Zacharchuk et al. |
| 2006/0270668 A1 | 11/2006 | Chew et al. |
| 2006/0270669 A1 | 11/2006 | Chew et al. |
| 2007/0014859 A1 | 1/2007 | Shah et al. |
| 2007/0048754 A1* | 3/2007 | Freeman .............. C07K 14/71 435/6.14 |
| 2007/0104721 A1 | 5/2007 | Moore et al. |
| 2007/0105887 A1 | 5/2007 | Moore |
| 2007/0281932 A1 | 12/2007 | Bernier et al. |
| 2008/0096212 A1 | 4/2008 | Bell et al. |
| 2008/0112888 A1 | 5/2008 | Wang |
| 2008/0166359 A1 | 7/2008 | Lamb |
| 2008/0193448 A1 | 8/2008 | Baum |
| 2008/0207615 A1 | 8/2008 | Bell et al. |
| 2008/0234264 A1 | 9/2008 | Bell et al. |
| 2008/0254040 A1 | 10/2008 | Stefanic et al. |
| 2008/0268034 A1 | 10/2008 | Karanth et al. |
| 2008/0286771 A1 | 11/2008 | Hudson et al. |
| 2008/0286785 A1 | 11/2008 | Nishio et al. |
| 2009/0035269 A1 | 2/2009 | Weber |
| 2009/0047278 A1 | 2/2009 | Owa et al. |
| 2009/0060873 A1 | 3/2009 | Sporn et al. |
| 2009/0176827 A1 | 7/2009 | Lu et al. |
| 2009/0203709 A1 | 8/2009 | Steinberg et al. |
| 2009/0246198 A1 | 10/2009 | Dong et al. |
| 2009/0297519 A1 | 12/2009 | Moore et al. |
| 2009/0306101 A1 | 12/2009 | Solca et al. |
| 2009/0312360 A1 | 12/2009 | Zacharchuk |
| 2009/0317456 A1 | 12/2009 | Karrasch et al. |
| 2009/0318480 A1 | 12/2009 | Solca |
| 2009/0325877 A1 | 12/2009 | Grunt et al. |
| 2010/0041904 A1 | 2/2010 | Jiang et al. |
| 2010/0048540 A1 | 2/2010 | Boyle et al. |
| 2010/0048892 A1 | 2/2010 | Anderson et al. |
| 2010/0056777 A1 | 3/2010 | Anderson et al. |
| 2010/0069340 A1 | 3/2010 | Zacharchuk et al. |
| 2010/0081632 A1 | 4/2010 | Oksenberg et al. |
| 2010/0087482 A1 | 4/2010 | Haber et al. |
| 2010/0092490 A1 | 4/2010 | Uenaka et al. |
| 2010/0105031 A1 | 4/2010 | Matsui et al. |
| 2010/0113474 A1 | 5/2010 | Zacharchuk et al. |
| 2010/0120072 A1 | 5/2010 | Lorence et al. |
| 2010/0120768 A1 | 5/2010 | Steinberg et al. |
| 2010/0143340 A1 | 6/2010 | Kolhe et al. |
| 2010/0143350 A1 | 6/2010 | Green et al. |
| 2010/0166744 A1 | 7/2010 | Wong |
| 2010/0189773 A1 | 7/2010 | Mortimore et al. |
| 2010/0226943 A1 | 9/2010 | Brennan et al. |
| 2010/0297118 A1 | 11/2010 | Macdougall et al. |
| 2010/0298760 A1 | 11/2010 | Olle et al. |
| 2010/0310503 A1 | 12/2010 | Li et al. |
| 2011/0014117 A1 | 1/2011 | Wang et al. |
| 2011/0045459 A1 | 2/2011 | Mischel et al. |
| 2011/0052570 A1 | 3/2011 | Klagsbrun et al. |
| 2011/0091421 A1 | 4/2011 | Mann |
| 2011/0091524 A1 | 4/2011 | Wang et al. |
| 2011/0097340 A1 | 4/2011 | Ramachandra et al. |
| 2011/0104256 A1 | 5/2011 | Wang et al. |
| 2011/0111018 A1 | 5/2011 | Asraf et al. |
| 2011/0112180 A1 | 5/2011 | Jiang et al. |
| 2011/0129456 A1 | 6/2011 | Wang et al. |
| 2011/0165257 A1 | 7/2011 | Rao et al. |
| 2012/0071507 A1 | 3/2012 | Berkenblit et al. |
| 2012/0270896 A1 | 10/2012 | Zacharchuk |
| 2012/0308560 A1 | 12/2012 | Moore et al. |
| 2013/0189274 A1 | 7/2013 | Berkenblit et al. |
| 2013/0281488 A1 | 10/2013 | Lu et al. |
| 2013/0316935 A1 | 11/2013 | Bell et al. |
| 2014/0004203 A1 | 1/2014 | Rao et al. |
| 2014/0050721 A1 | 2/2014 | Moore et al. |
| 2014/0171384 A1 | 6/2014 | Zacharchuk et al. |
| 2016/0310482 A1 | 10/2016 | Haber |

FOREIGN PATENT DOCUMENTS

| | | |
|---|---|---|
| EP | 0693285 A2 | 1/1996 |
| EP | 1448531 B1 | 8/2007 |
| EP | 1663978 B1 | 11/2007 |
| EP | 1854463 A1 | 11/2007 |
| EP | 1978106 A1 | 10/2008 |
| EP | 1951274 B1 | 12/2009 |
| EP | 1848414 B1 | 4/2011 |
| EP | 1859793 B1 | 4/2011 |
| EP | 2656844 A1 | 10/2013 |
| JP | 2003-519698 A | 6/2003 |
| JP | 2007-145745 A | 6/2007 |
| WO | WO 1992/22653 A1 | 12/1992 |
| WO | WO 1995/28406 A1 | 10/1995 |
| WO | WO 1996/33978 A1 | 10/1996 |
| WO | WO 1996/33980 A1 | 10/1996 |
| WO | WO 1998/43960 A1 | 10/1998 |
| WO | WO 2000/018761 A1 | 4/2000 |
| WO | WO 2001/023395 A2 | 4/2001 |
| WO | WO 2001/051919 A2 | 7/2001 |
| WO | WO 2002/080975 A1 | 10/2002 |
| WO | WO 2002/098416 A2 | 12/2002 |
| WO | WO 2002/102976 A2 | 12/2002 |
| WO | WO 2003/050090 A1 | 6/2003 |
| WO | WO 2003/103676 A2 | 12/2003 |
| WO | WO 2004/004644 A2 | 1/2004 |
| WO | WO 2004/066919 A2 | 8/2004 |
| WO | WO 2004/078133 A2 | 9/2004 |
| WO | WO 2004/093854 A2 | 11/2004 |
| WO | WO 2004/096224 A2 | 11/2004 |

(56) References Cited

FOREIGN PATENT DOCUMENTS

| | | |
|---|---|---|
| WO | WO 2005/018677 A2 | 3/2005 |
| WO | WO 2005/032513 A2 | 4/2005 |
| WO | WO 2005/034955 A1 | 4/2005 |
| WO | WO 2005/037287 A1 | 4/2005 |
| WO | WO 2005/044091 A2 | 5/2005 |
| WO | WO 2005/049021 A1 | 6/2005 |
| WO | WO 2005/087265 A1 | 9/2005 |
| WO | WO 2005/094357 A2 | 10/2005 |
| WO | WO 2006/044453 A1 | 4/2006 |
| WO | WO 2006/044748 A2 | 4/2006 |
| WO | WO 2006/081985 A1 | 8/2006 |
| WO | WO 2006/084058 A2 | 8/2006 |
| WO | WO 2006/095185 A1 | 9/2006 |
| WO | WO 2006/098978 A1 | 9/2006 |
| WO | WO 2006/113151 A2 | 10/2006 |
| WO | WO 2006/113304 A2 | 10/2006 |
| WO | WO 2006/116514 A2 | 11/2006 |
| WO | WO 2006/120557 A1 | 11/2006 |
| WO | WO 2006/120573 A2 | 11/2006 |
| WO | WO 2006/127205 A2 | 11/2006 |
| WO | WO 2006/127207 A1 | 11/2006 |
| WO | WO 2007/000234 A1 | 1/2007 |
| WO | WO 2007/011619 A2 | 1/2007 |
| WO | WO 2007/056118 A1 | 5/2007 |
| WO | WO 2007/075794 A2 | 7/2007 |
| WO | WO 2007/095038 A2 | 8/2007 |
| WO | WO 2007/116025 A2 | 10/2007 |
| WO | WO 2007/130438 A2 | 11/2007 |
| WO | WO 2007/137187 A2 | 11/2007 |
| WO | WO 2007/139797 A2 | 12/2007 |
| WO | WO 2008/076143 A1 | 6/2008 |
| WO | WO 2008/076278 A2 | 6/2008 |
| WO | WO 2008/089087 A2 | 7/2008 |
| WO | WO 2008/093878 A1 | 8/2008 |
| WO | WO 2008/121467 A2 | 10/2008 |
| WO | WO 2008/127710 A2 | 10/2008 |
| WO | WO 2008/130910 A1 | 10/2008 |
| WO | WO 2009/036099 A1 | 3/2009 |
| WO | WO 2009/042613 A1 | 4/2009 |
| WO | WO 2009/052264 A2 | 4/2009 |
| WO | WO 2009/061349 A1 | 5/2009 |
| WO | WO 2009/105234 A2 | 8/2009 |
| WO | WO 2009/108637 A1 | 9/2009 |
| WO | WO 2009/111073 A2 | 9/2009 |
| WO | WO 2009/121031 A1 | 10/2009 |
| WO | WO 2009/126662 A1 | 10/2009 |
| WO | WO 2009/129545 A1 | 10/2009 |
| WO | WO 2009/129546 A1 | 10/2009 |
| WO | WO 2009/129548 A1 | 10/2009 |
| WO | WO 2009/146216 A2 | 12/2009 |
| WO | WO 2009/146218 A2 | 12/2009 |
| WO | WO 2009/151910 A2 | 12/2009 |
| WO | WO 2010/008744 A2 | 1/2010 |
| WO | WO 2010/011782 A1 | 1/2010 |
| WO | WO 2010/045318 A2 | 4/2010 |
| WO | WO 2010/048477 A2 | 4/2010 |
| WO | WO 2010/054051 A1 | 5/2010 |
| WO | WO 2010/085845 A1 | 8/2010 |
| WO | WO 2010/091140 A1 | 8/2010 |
| WO | WO 2010/098627 A2 | 9/2010 |
| WO | WO 2010/104406 A1 | 9/2010 |
| WO | WO 2010/117633 A1 | 10/2010 |
| WO | WO 2010/120861 A1 | 10/2010 |
| WO | WO 2010/124009 A2 | 10/2010 |
| WO | WO 2010/129053 A2 | 11/2010 |
| WO | WO 2011/002857 A2 | 1/2011 |
| WO | WO 2011/008053 A2 | 1/2011 |
| WO | WO 2011/008054 A2 | 1/2011 |
| WO | WO 2011/025267 A2 | 3/2011 |
| WO | WO 2011/025269 A2 | 3/2011 |
| WO | WO 2011/025271 A2 | 3/2011 |
| WO | WO 2011/025720 A1 | 3/2011 |
| WO | WO 2011/038467 A1 | 4/2011 |
| WO | WO 2011/056741 A2 | 5/2011 |
| WO | WO 2011/060206 A2 | 5/2011 |
| WO | WO 2011/069962 A1 | 6/2011 |
| WO | WO 2011/070499 A1 | 6/2011 |

OTHER PUBLICATIONS

Fry et al. (Proc. Natl. Acad. Sci. USA Sep. 1998, 95:12022-12027).*
Tsou et al. (J. Med. Chem. 2001 44:2719-2734).*
Smaill et al. (J. Med. Chem 1999 42:1803-1815).*
Pao et al. (PLoS Medicine Feb. 22, 2005, 2 (3)(e73): 225-235) (Year: 2005).*
Smaill et al. (J. Med. Chem. 2001 44: 429-440) (Year: 2001).*
"Trastuzumab." Wikipedia: Wikipedia: The Free Encyclopedia. Wikimedia Foundation, Inc. Retrieved from the Internet Aug. 14, 2009. URL:http://en.wikipedia.org/wiki/Herceptin.
"Vinorelbin." *Wikipedia: The Free Encyclopedia*. Wikimedia Foundation, Inc. Retrieved from the Internet on Jan. 28, 2013. URL:http://en.wikipedia.org/wiki/Vinorelbine.
Abbas et al., "A Drug Interaction Study to Evaluate the Effect of Ketoconazole on the Pharmacokinetics (PK) of Neratinib in Healthy Subjects," Clin. Pharmacol. Therapeutics 85:s44 (2009).
Abbas et al., "Evaluation of Neratinib (HKI-272) and Paclitaxel Pharmacokinetics (PK) in Asian and Caucasian Patients with Erbb2+ Breast Cancer: a Phase 1/2 Study of Neratinib in Combination with Paclitaxel," Ann. Oncol. 21:101 (2010).
Abbas et al., "Pharmacokinetics of Oral Neratinib During Co-Administration of Ketoconazole in Healthy Subjects," Br. J. Clin. Pharmacol. 71(4):522-527 (2011).
Abbas-Borhan et al., "A Clinical Study to Characterize the Occurrence of Mild-To-Moderate Diarrhea After Administration of Neratinib Either Once Daily or Twice Daily for 14 Days," EJC Suppl. 8:143 (2010).
Abbas-Borhan et al., "An Open-Label Study to Assess the Mass Balance and Metabolic Disposition of an Orally Administered Single Dose of 14C-Labeled Neratinib, an Irreversible pan-EibB inhibitor, in Healthy Subjects," Drug Metab. Rev. 42:S1, 216 Abstr. p. 330 (2010).
Abrams et al., "Preclinical evaluation of the tyrosine kinase inhibitor SU11248 as a single agent and in combination with "standard of care" therapeutic agents for the treatment of breast cancer," Mol. Cancer Ther. 2(10):1011-1021 (2003).
Abramson and Arteaga, "New Strategies in HER2-Overexpressing Breast Cancer: Many Combinations of Targeted Drugs Available," Clin. Cancer Res. 17:952-958 (2011).
Adelaide et al., "Integrated Profiling of Basal and Luminal Breast Cancers," Cancer Res. 67(24):11565-11575 (2007).
Al-Dasooqi et al., "HER2 Targeted Therapies for Cancer and the Gastrointestinal Tract," Curr. Drug Targets 10(6):537-542 (2009).
Ali et al., "Mutational Spectra of PTEN/MMAC1 Gene: a Tumor Suppressor with Lipid Phosphatase Activity," J. Natl. Cancer Inst. 91(22):1922-1932 (1999).
Allegra et al., "American Society of Clinical Oncology Provisional Clinical Opinion: Testing for KRAS Gene Mutations in Patients With Metastatic Colorectal Carcinoma to Predict Response to Anti-Epidermal Growth Factor Receptor Monoclonal Antibody Therapy," J. Clin. Oncol. 27(12):2091-2096 (2009).
Allen et al., "Potential benefits of the irreversible pan-erbB inhibitor, CI-1033, in the treatment of breast cancer," Semin. Oncol. 29(3 Suppl 11):11-21 (2002).
Al-Muhammed et al., "In-Vivo Studies on Dexamethasone Sodium Phosphate Liposomes," J. Microencapsul. 13(3):293-306 (1996).
Alvarez et al., "Emerging Targeted Therapies for Breast Cancer," J. Clin. Oncol. 28(20):3366-3379 (2010).
Alvarez, "Present and Future Evolution of Advanced Breast Cancer Therapy," Breast Cancer Res. 12(Suppl 2):S1 (2010).
Amslinger, "The tunable functionality of alpha,beta-unsaturated carbonyl compounds enables their differential application in biological systems," ChemMedChem. 5(3):351-356 (2010).
Andre and Diniz, "Targeted regimes without cytotoxics—are they ready for prime time?" EJC Suppl. 7:49 Abst. 191 (2009).
Andre et al., "Everolimus for women with trastuzumab-resistant, HER2-positive, advanced breast cancer (BOLERO-3): a randomised,

(56) References Cited

OTHER PUBLICATIONS double-blind, placebo-controlled phase 3 trial," Lancet Oncol. 15(6):580-591 (2014) (Epub Apr. 14, 2014).
Anonymous, "Trastuzumab", Wikipedia, Retrieved from the Internet on Nov. 21, 2014. URL:http://en.wikipedia.org/wiki/Trastuzumab?oldid=634842165.
Anonymous: "Meeting Archives of Chemotherapy Foundation Symposium XXIV, Nov. 7-10, 2007", The Chemotherapy Foundation, Nov. 8, 2007, Retrieved from the Internet on Jan. 13, 2010: URL:http://www.chemotherapyfoundationsymposium.org/meeting_archives/meetingarchives_tcf2007_main.html.
Anonymous: "Anticancer Agent—neratinib", Manufacturing Chemist, Dec. 2010/Jan. 2011, p. 27.
Arteaga, "ErbB-targeted therapeutic approaches in human cancer," Exp. Cell. Res. 284(1):122-130 (2003).
Avizienyte et al., "Comparison of the EGFR resistance mutation profiles generated by EGFR-targeted tyrosine kinase inhibitors and the impact of drug combinations," Biochem. J. 415(2):197-206 (2008).
Awada and Piccart-Gebhart, "Management of HER-2/Neu-Positive Metastatic Breast Cancer," Eur. J. Cancer (Suppl. 6):2-9 (2008).
Awada et al., "Safety and Efficacy of Neratinib (HKI-272) in Combination with Vinorelbine in ErbB2+ Metastatic Breast Cancer," Cancer Res. 69:24(Suppl 3) Abstr. 5095 (2009).
Awada et al., "Safety and Efficacy of Neratinib (HKI-272) in Combination with Vinorelbine in ErbB2+ Metastatic Breast Cancer (MBC)," Ann. Oncol. 21(Suppl. 4):iv62-iv63 Abstr. 145P (2010).
Awada et al., "Safety and efficacy of neratinib (HKI-272) plus vinorelbine in the treatment of patients with ErbB2-positive metastatic breast cancer pretreated with anti-HER2 therapy," Ann. Oncol. 24(1):109-116 (2013) (Epub Sep. 11, 2012).
Azria et al., "[Radiotherapy and inhibitors of epidermal growth factor receptor: preclinical findings and preliminary clinical trials]," Bull Cancer 90 Spec No. S202-S212 (2003). (Abstract only).
Badache and Goncalves, "The ErbB2 signaling network as a target for breast cancer therapy," J. Mammary Gland Biol. Neoplasia 11(1):13-25 (2006).
Barton et al., "Predictive molecular markers of response to epidermal growth factor receptor(EGFR) family-targeted therapies," Curr. Cancer Drug Targets 10(8):799-812 (2010).
Baselga and Swain, "Novel anticancer targets: revisiting ERBB2 and discovering ERBB3," Nat. Rev. Cancer 9(7):463-475 (2009) (Epub Jun. 18, 2009).
Baselga et al., "Phase I safety, pharmacokinetic, and pharmacodynamic trial of ZD1839, a selective oral epidermal growth factor receptor tyrosine kinase inhibitor, in patients with five selected solid tumor types," J. Clin. Onc. 20(21):4292-4302 (2002).
Baselga, "Is there a role for the irreversible epidermal growth factor receptor inhibitor EKB-569 in the treatment of cancer? A mutation-driven question," J. Clin. Oncol. 24(15):2225-2226 (2006).
Baselga, "Novel agents in the era of targeted therapy: what have we learned and how has our practice changed?" Ann. Oncol. 19(Suppl 7):vii281-vii288 (2008).
Baselga, "Treatment of HER2-Overexpressing Breast Cancer," Ann. Oncol. (Suppl 7):vii36-vii40 (2010).
Bayes et al., "Gateways to clinical trials," Methods Find. Exp. Clin. Pharmacol. 28(9):657-678 (2006).
Bedard et al., "Beyond trastuzumab: overcoming resistance to targeted HER-2 therapy in breast cancer," Curr. Cancer Drug Targets 9(2):148-162 (2009).
Bedard et al., "Stemming resistance to HER-2 targeted therapy," J. Mammary Gland Biol. Neoplasia 14(1):55-66 (2009) (Epub Mar. 4, 2009).
Belani, "The role of irreversible EGFR inhibitors in the treatment of non-small cell lung cancer: overcoming resistance to reversible EGFR inhibitors," Cancer Invest. 28(4):413-423 (2010).
Bell and Haber, "A blood-based test for epidermal growth factor receptor mutations in lung cancer," Clin. Cancer Res. 12(13):3875-3877 (2006).

Berns et al., "A functional genetic approach identifies the PI3K pathway as a major determinant of trastuzumab resistance in breast cancer," Cancer Cell 12(4):395-402 (2007).
Berz and Wanebo, "Targeting the growth factors and angiogenesis pathways: small molecules in solid tumors," J. Surg. Oncol. 103(6):574-586 (2011).
Besse et al., "Neratinib (HKI-272), an irreversible pan-ErbB receptor tyrosine kinase inhibitor: preliminary results of a phase 2 trial in patients with advanced non-small cell lung cancer," Eur. J. Cancer (Suppl.):23 Abstr. 203 (2008).
Besse et al., "Targeted therapies in lung cancer," Ann. Oncol. 18(Suppl. 9):ix135-ix142 (2007).
Bettendorf et al., "Chromosomal imbalances, loss of heterozygosity, and immunohistochemical expression of TP53, RB1, and PTEN in intraductal cancer, intraepithelial neoplasia, and invasive adenocarcinoma of the prostate," Genes Chromosomes Cancer 47(7):565-572 (2008).
Bischoff and Ignatov, "The Role of Targeted Agents in the Treatment of Metastatic Breast Cancer," Breast Care (Basel) 5(3):134-141 (2010) (Epub Jun. 16, 2010).
Blanco-Aparicio et al., "PTEN, More Than the AKT Pathway," Carcinogenesis 28(7):1379-1386 (2007) (Epub Mar. 6, 2007).
Blanke, "Gefitinib in colorectal cancer: if wishes were horses," J. Clin. Oncol. 23(24):5446-5449 (2005).
Blencke et al., "Mutation of threonine 766 in the epidermal growth factor receptor reveals a hotspot for resistance formation against selective tyrosine kinase inhibitors," J. Biol. Chem. 278(17):15435-15440 (2003) (Epub Feb. 19, 2003).
Board et al., "Multiplexed assays for detection of mutations in PIK3CA," Clin. Chem 54(4):757-760 (2008).
Bonanno et al., "Mechanisms of acquired resistance to epidermal growth factor receptor tyrosine kinase inhibitors and new therapeutic perspectives in non small cell lung cancer," Curr. Drug Targets 12(6):922-933 (2011).
Boschelli et al., "Bosutinib: a review of preclinical studies in chronic myelogenous leukaemia," Eur. J. Cancer. 46(10):1781-1789 (2010).
Boschelli, "4-Anilino-3-quinolinecarbonitriles: An Emerging Class of Kinase Inhibitors—An Update," Med. Chem Rev. Online 1:457-463 (2004).
Bose and Ozer, "Neratinib: an oral, irreversible dual EGFR/HER2 inhibitor for breast and non-small cell lung cancer," Expert Opin. Investig. Drugs 18(11):1735-1751 (2009).
Bose et al., "Allelic loss of chromosome 10q23 is associated with tumor progression in breast carcinomas," Oncogene 17(1):123-127 (1998).
Bose et al., "Reduced expression of PTEN correlates with breast cancer progression," Hum. Pathol. 33(4):405-409 (2002).
Boyce et al., "Requirement of pp60c-src expression for osteoclasts to form ruffled borders and resorb bone in mice," J. Clin. Invest. 90(4):1622-1627 (1992).
Boyd et al., "Lapatanib: Oncolytic Dual EFGR and erbB-2 Inhibitor," Drugs Future 30(12):1225-1239 (2005).
Brackstone et al., "Canadian initiatives for locally advanced breast cancer research and treatment: inaugural meeting of the Canadian Consortium for LABC," Curr. Oncol. 18(3):139-144 (2011).
Bridges, "Current Progress Towards the Development of Tyrosine Kinase Inhibitors as Anticancer Agents," Expert Opin. Emerg. Drugs. 3:279-292 (1998).
Brittain, Harry G. (Eds), "Polymorphism in Pharmaceutical Solids", Chapters 1 and 5, Marcel Dekker, Inc., New York (1999).
Brook et al., "Management of transitional cell carcinoma by targeting the epidermal growth factor receptor," Therapy 3(3):407-416 (2006).
Browne et al., "HER-2 Signaling and Inhibition in Breast Cancer," Curr. Cancer Drug Targets 9(3):419-438 (2009).
Broxterman and Georgopapadakou, "Anticancer therapeutics: a surge of new developments increasingly target tumor and stroma," Drug Resist. Updat. 10(4-5):182-193 (2007) (Epub Sep. 12, 2007).
Buerger et al., "Allelic length of a CA dinucleotide repeat in the egfr gene correlates with the frequency of amplifications of this sequence—first results of an inter-ethnic breast cancer study," J. Pathol. 203(1):545-550 (2004).

(56) References Cited

OTHER PUBLICATIONS

Bullard Dunn et al., "Evolving Therapies and FAK Inhibitors for the Treatment of Cancer," Anticancer Agents Med. Chem. 10(10):722-734 (2010).
Burnstein et al., "Gastrointestinal and Cardiovascular Safety Profiles of Neratinib Monotherapy in Patients with Advanced Erbb2-Positive Breast Cancer," Cancer Res. 69:Abst 5096 (2009).
Burstein et al., "HKI-272, an irreversible pan erbB receptor tyrosine kinase inhibitor: preliminary phase 2 results in patients with advanced breast cancer," Breast Cancer Res. Treat. 106:S268 Abstr. 6061 (2007).
Burstein et al., "Neratinib (HKI-272), an irreversible pan ErbB receptor tyrosine kinase inhibitor: phase 2 results in patients with advanced HER2+ breast cancer," Cancer Res. 69(2 Suppl.) Abstr. 37 (2009).
Burstein et al., "Neratinib, an irreversible ErbB receptor tyrosine kinase inhibitor, in patients with advanced ErbB2-positive breast cancer," J. Clin. Oncol. 28(8):1301-1307 (2010).
Burstein, "The Distinctive Nature of HER2-Positive Breast Cancers," N. Engl. J. Med. 353(16):1652-1654 (2005).
Byrn et al., "Pharmaceutical solids: a strategic approach to regulatory considerations," Pharm. Res. 12(7):945-954 (1995).
Callahan and Hurwitz, "Human epidermal growth factor receptor-2-positive breast cancer: Current management of early, advanced, and recurrent disease," Curr. Opin. Obstet. Gynecol. 23(1):37-43 (2011).
Camp et al., "Molecular mechanisms of resistance to therapies targeting the epidermal growth factor receptor," Clin. Cancer Res. 11(1):397-405 (2005).
Campas et al., "BIBW-2992. Dual EGFR/HER2 Inhibitor Oncolytic;Tovok™," Drugs Future 33(8):649-654 (2008).
Campbel et al., "Gefitinib for the Treatment of Non-Small-Cell Lung Cancer," Expert Opin. Pharmacother. 11(8):1343-1357 (2010).
Cao et al., "Epidermal Growth Factor Receptor as a Target for Anti-Cancer Agent Design," Anticancer Agents Med. Chem. 10(6):491-503 (2010).
Cappuzzo et al., "Gefitinib in pretreated non-small-cell lung cancer (NSCLC): analysis of efficacy and correlation with HER2 and epidermal growth factor receptor expression in locally advanced or metastatic NSCLC," J. Clin. Oncol. 21(14):2658-2663 (2003).
Cappuzzo et al., "Surrogate predictive biomarkers for response to anti-EGFR agents: state of the art and challenges," Int. J. Biol. Markers 22(1 Suppl 4):S10-S23 (2007).
Cardoso et al., "Locally Recurrent or Metastatic Breast Cancer: ESMO Clinical Practice Guidelines for Diagnosis, Treatment and Follow-Up," Ann. Oncol. 21(5):v15-v19 (2010).
Carney et al., "HER-2/neu diagnostics in breast cancer," Breast Cancer Res. 9(3):207 (2007).
Carter et al., "Small-Molecule Inhibitors of the Human Epidermal Receptor Family," Expert Opin. Investig. Drugs 18(12):1829-1842 (2009).
Cascone et al., "Epidermal Growth Factor Receptor Inhibitors in Non-Small-Cell Lung Cancer," Expert Opin. Drug Discov. 2(3):335-348 (2007).
Centre de Lutte Contre le Cancer Georges-Francois Leclerc (Fumoleau P. Study chair): "Lapatinib and Vinorelbine in Treating Women With HER2-Overexpressing Locally Advanced or Metastatic Breast Cancer" Clinical Trials Aug. 6, 2007 Retrieved from the Internet: URL:http://clinicaltrials.gov/ct2/show/NCT00513058?term=lapatinib+and+vinorelbine&rank=1 [retrieved on Jan. 13, 2010].
Chan and Giaccia, "Harnessing Synthetic Lethal Interactions in Anticancer Drug Discovery," Nat. Rev. Drug Discov. 10(5):351-364 (2011).
Chan, "A review of the use of trastuzumab (Herceptin®) plus vinorelbine in metastatic breast cancer," Ann. Oncol.18(7):1152-1158 (2007) (Epub Jan. 29, 2007) Review.
Chandrasekaran et al., "Reversible Covalent Binding of Neratinib to Human Serum Albumin in Vitro," Drug Metab. Lett. 4(4):220-227 (2010).

Chen et al., "Epidermal growth factor receptor inhibitors: current status and future directions," Curr. Probl. Cancer 33(4):245-294 (2009).
Chenoweth, "Can single-patient investigational new drug studies hurry slow trains to the fast track?" Drug Discov. Today 11(5-6):185-186 (2006).
Cheung and Paterson, "American Chemical Society—226th National Meeting. Pain and Oncology," Idrugs 6(10):935-936 (2003).
Chew, H. K. et al., EGFR Inhibition with Lapatinib in Combination with Vinorelbine: A Phase I Study, Chemotherapy Foundation Symposium XXV, Chemotherapy Foundation, 2007, [Retrieved on Aug. 30, H-25 (2013)], obtained from the Internet, URL, http://chemotherapyfoundationsymposium.org/CMS/2007-archives-main.
Chew, Helen K., MD (University of California, Davis): "Lapatinib and Vinorelbine in Treating Patients With Advanced Solid Tumors" ClinicalTrials, Oct. 18, 2006, Retrieved from the Internet: URL:http//clinicaltrials.gov/ct2/show/NCT00389922?term=lapatinib+and+vinorelnine&rank=2 [retrieved on Jan. 13, 2010].
Chien and Rugo, "The Cardiac Safety of Trastuzumab in the Treatment of Breast Cancer," Expert Opin. Drug Saf. 9(2):335-346 (2010).
Chirieac and Dacic, "Targeted Therapies in Lung Cancer," Surg. Pathol. Clin. 3(1):71-82 (2010).
Chmielecki et al. Selection for the EGFR T790M gatekeeper resistance mutation may vary among different small molecule EGFR TKIs [abstract]. In: Proceedings of the 101st Annual Meeting of the American Association for Cancer Research; Apr. 17-21, 2010; Washington, DC. Philadelphia (PA): AACR; Cancer Res 2010;70(8 Suppl):Abstract nr 1774.
Cho et al., "Structure of the extracellular region of HER2 alone and in complex with the Herceptin Fab," Nature 421(6924):756-760 (2003).
Chonn et al., "Recent Advances in Liposomal Drug-Delivery Systems," Curr. Opin. Biotechnol. 6(6):698-708 (1995).
Choong et al., "Gefitinib response of erlotinib-refractory lung cancer involving meninges—role of EGFR mutation," Nat. Clin. Pract. Oncol. 3(1):50-57 (2006).
Chow et al., "Safety and efficacy of neratinib (HKI-272) in combination with paclitaxel in ErbB2+ metastatic breast cancer," Cancer Res. (Meeting Abstracts) 69:S5081 (2009).
Chow et al., "Safety and efficacy of neratinib (HKI-272) in combination with paclitaxel in patients with solid tumors," J. Clin. Oncol. (Meeting Abstracts) 27(15S):3557 (2009).
Chow et al., "Safety and efficacy of neratinib (HKI-272) in combination with paclitaxel in ERBB2+ metastatic breast cancer (MBC)," Ann. Oncol. 21(Suppl 4):iv62 Abstr. 144P (2010).
Cicenas, "The Potential Role of the EGFR/ERBB2 Heterodimer in Breast Cancer," Expert Opin. Ther. Patents 17(6):607-616 (2007).
Clouser et al., "Biomarker Targets and Novel Therapeutics," Cancer Treat. Res. 149:85-105 (2009).
Cobleigh et al., "Multinational study of the efficacy and safety of humanized anti-HER2 monoclonal antibody in women who have HER2-overexpressing metastatic breast cancer that has progressed after chemotherapy for metastatic disease," J. Clin. Oncol. 17(9):2639-2648 (1999).
Cohen et al., "United States Food and Drug Administration Drug Approval summary. Gefitinib (ZD1839; Iressa) tablets," Clin. Cancer Res. 10(4):1212-1218 (2004).
Coldren et al., "Baseline gene expression predicts sensitivity to gefitinib in non-small cell lung cancer cell lines," Mol. Cancer Res. 4(8):521-528 (2006).
Collins et al., "Lapatinib: a competitor or companion to trastuzumab?" Cancer Treat. Rev. 35(7):574-581 (2009).
Colombo et al., "HER2 targeting as a two-sided strategy for breast cancer diagnosis and treatment: Outlook and recent implications in nanomedical approaches," Pharmacol. Res. 62(2):150-165 (2010) (Epub Feb. 1, 2010).
Conte et al., "Evolving nonendocrine therapeutic options for metastatic breast cancer: how adjuvant chemotherapy influences treatment," Clin. Breast Cancer 7(11):841-849 (2007).
Cooper and Cohen, "Mechanisms of resistance to EGFR inhibitors in head and neck cancer," Head Neck 31(8):1086-1094 (2009).

(56) References Cited

OTHER PUBLICATIONS

Correspondence from Chilean associate regarding a First Office Action issued in corresponding Chilean Patent Application No. 2961-2006 dated 2009-2010.

Correspondence from Israeli associate regarding a First Office Action issued in corresponding Israeli Patent Application No. 190805 dated 2010.

Correspondence from Peruvian associate regarding an Opposition filed against corresponding Peruvian Patent Application No. 001 342-2006/QIN dated 2007.

Cortes-Funes et al., "Neratinib, An Irreversible Pan Erb Receptor Tyrosine Kinase Inhibitor Active for Advanced HER2+ Breast Cancer," Breast Cancer Res. 11 Suppl 1:S19 (2009).

Coughlin et al., "Approaches and limitations of phosphatidylinositol-3-kinase pathway activation status as a predictive biomarker in the clinical development of targeted therapy," Breast Cancer Res. Treat. 124(1):1-11 (2010) (Epub Aug. 28, 2010).

Cox, "Regression Models and Life Tables (With Discussion)," Journal of the Royal Statistical Society. Series B (Methodological), vol. 34, No. 2. (1972), pp. 187-220.

Da Cunha Santos et al., "EGFR Mutations and Lung Cancer," Ann. Rev. Pathol. 6:49-69 (2011).

Damia and D'Incalci, "Contemporary pre-clinical development of anticancer agents—what are the optimal preclinical models?" Eur. J. Cancer 45(16):2768-2781 (2009) (Epub Sep. 15, 2009).

Dancey, "Epidermal growth factor receptor inhibitors in non-small cell lung cancer," Drugs 67(8):1125-1138 (2007).

Dang et al.,"The safety of dose-dense doxorubicin and cyclophosphamide followed by paclitaxel with trastuzumab in HER-2/neu overexpressed/amplified breast cancer," J. Clin. Oncol. 26(8):1216-1222 (2008).

Daniele and Sapino, "Anti-HER2 treatment and breast cancer: state of the art, recent patents, and new strategies," Recent Pat. Anticancer Drug Discov. 4(1):9-18 (2009).

Davidian, M. (2006) Introduction to statistical population modeling and analysis for pharmacokinetic data. Invited white paper for the International Workshop on Uncertainty and Variability in Physiologically Based Pharmacokinetic (PBPK) Models. Retrieved from the Internet: URL:http://www.epa.gov/ncct/uvpkm/files/Calibration_PreMeeting_Draft.pdf (89 pages) [Retrieved on Jan. 29, 2014].

Davidson, "HER2-Targeted Therapies: How Far We've Come—And Where We're Headed," Oncology (Williston Park) 25(5):425-426 (2011).

Davoli et al., "Progression and Treatment of HER2-Positive Breast Cancer," Cancer Chemother. Pharmacol. 65(4):611-623 (2010) (Epub Dec. 20, 2009).

De Bono and Rowinsky, "The ErbB receptor family: a therapeutic target for cancer," Trends Mol. Med. 8(4 Suppl):S19-S26 (2002).

De Luca and Normanno, "Predictive biomarkers to tyrosine kinase inhibitors for the epidermal growth factor receptor in non-small-cell lung cancer," Curr. Drug Targets 11(7):851-864 (2010).

De Maio et al., "Vinorelbine plus 3-weekly trastuzumab in metastatic breast cancer: a single-centre phase 2 trial," BMC Cancer. 7:50 (2007).

De Seranno and Meuwissen, "Progress and Applications of Mouse Models for Human Lung Cancer," Eur. Respir. J. 5(2):426-443 (2010).

Dempke and Heinemann, "Resistance to EGF-R (erbB-1) and VEGF-R modulating agents," Eur. J. Cancer 45(7):1117-1128 (2009) (Epub Jan. 3, 2009).

Depowski et al., "Loss of expression of the PTEN gene protein product is associated with poor outcome in breast cancer," Mod. Pathol. 14(7):672-676 (2001).

Di Cosimo and Baselga, "Management of breast cancer with targeted agents: importance of heterogeneity. [corrected]." Nat. Rev. Clin. Oncol. 7(3):139-147 (2010) (Epub Feb. 2, 2010).

Di Cosimo and Baselga, "Targeted Therapies in Breast Cancer: Where Are We Now?" Eur. J. Cancer 44(18):2781-2790 (2008) (Epub Nov. 14, 2008).

Di Maio et al., "New drugs in advanced non-small-cell lung cancer: searching for the correct clinical development," Expert Opin. Investig. Drugs 19(12):1503-1514 (2010) (Epub Nov. 4, 2010).

Dickler, "Updates on Therapeutic Approaches in HER2-Positive Disease," Clin. Adv. Hematol. Oncol. 8(2):105-107 (2010).

Dinh et al., "Trastuzumab for early breast cancer: current status and future directions," Clin. Adv. Hematol. Oncol. 5(9):707-717 (2007).

Dirix et al., "Neratinib Monotherapy in Patients with Advanced ERBB2-Positive Breast Cancer: Gastrointestinal and Cardiovascular Safety Profiles," Ann. Oncol. 21(Suppl 4):iv61-iv62 Abstr. 141P (2010).

Discafani et al., "Irreversible inhibition of epidermal growth factor receptor tyrosine kinase with in vivo activity by N-[4-[(3-bromophenyl)amino]-6-quinazolinyl]-2-butynamide (CL-387,785)," Biochem. Pharmacol. 57(8):917-925 (1999).

Doebele et al., "New strategies to overcome limitations of reversible EGFR tyrosine kinase inhibitor therapy in non-small cell lung cancer," Lung Cancer 69(1):1-12 (2010) (Epub Jan. 25, 2010).

Dorland's Illustrated Medical Dictionary. 31st ed. Philadelphia: Saunders Elsevier; c2007. Carcinoma; pp. 295-297.

Dowsett and Dunbier, "Emerging Biomarkers and New Understanding of Traditional Markers in Personalized Therapy for Breast Cancer," Clin. Cancer Res. 14(24):8019-8026 (2008).

Druker et al., "Efficacy and Safety of a Specific Inhibitor of the BCR-ABL Tyrosine Kinase in Chronic Myeloid Leukemia," N. Engl. J. Med. 344(14):1031-1037 (2001).

Eck and Yun, "Structural and Mechanistic Underpinnings of the Differential Drug Sensitivity of EGFR Mutations in Non-Small Cell Lung Cancer," Biochim. Biophys. Acta 1804(3):559-566 (2010).

Egloff and Grandis, "Targeting epidermal growth factor receptor and SRC pathways in head and neck cancer," Semin. Oncol. 35(3):286-297 (2008).

Eichhorn et al., "Phosphatidylinositol 3-kinase hyperactivation results in lapatinib resistance that is reversed by the mTOR/phosphatidylinositol 3-kinase inhibitor NVP-BEZ235," Cancer Res. 68(22):9221-9230 (2008).

Einhorn et al., "Summary Report 7th Annual Targeted Therapies of the Treatment of Lung Cancer," J. Thorac. Oncol. 3(5):545-555 (2008).

Einhorn, "Perspective on the Development of New Agents in Thoracic Cancers," Lung Cancer 50 Suppl 1:S27-S28 (2005).

Ellis and Crowder, "PIKing" the winner for phosphatidylinositol 3-kinase inhibitors in ErbB2-positive breast cancer: let's not "PTENed" it's easy! Clin. Cancer Res. 13(19):5661-5662 (2007).

Engelman and Settleman, "Acquired Resistance to Tyrosine Kinase Inhibitors During Cancer Therapy," Curr. Opin. Genet. Dev. 18(1):73-79 (2008) (Epub Mar. 5, 2008).

Engelman, "Targeting PI3K Signalling in Cancer: Opportunities, Challenges and Limitations," Nat. Rev. Cancer 9(8):550-562 (2009).

Engleman and Jänne, "Mechanisms of acquired resistance to epidermal growth factor receptor tyrosine kinase inhibitors in non-small cell lung cancer," Clin. Cancer Res. 14(10):2895-2899 (2008).

English Translation of an Opposition filed against corresponding Ecuador Patent Application No. SP-08-8423 dated 2008.

Ercan et al., "Amplification of EGFR T790M causes resistance to an irreversible EGFR inhibitor," Oncogene. 29(16):2346-2356 (2010) (Epub Feb. 1, 2010).

Erjala et al., "Concomitant chemoirradiation with vinorelbine and gefitinib induces additive effect in head and neck squamous cell carcinoma cell lines in vitro," Radiother. Oncol. 85(1):138-145 (2007).

Esteva et al., "Molecular predictors of response to trastuzumab and lapatinib in breast cancer," Nat. Rev. Clin. Oncol. 7(2):98-107 (2010) (Epub Dec. 22, 2009).

Ettinger et al., "Antiemesis," J. Natl. Compr. Canc. Netw. 10(4):456-485 (2012).

Eyles et al., "Oral delivery and fate of poly(lactic acid) microsphere-encapsulated interferon in rats," J. Pharm. Pharmacol. 49(7):669-674 (1997).

Farley and Birrer, "Novel Therapeutic Targets," Cancer Treat. Res.149:63-84 (2009).

Felip et al., "Emerging Drugs for Non-Small-Cell Lung Cancer," Expert Opin. Emerg. Drugs 12(3):449-460 (2007).

(56) References Cited

OTHER PUBLICATIONS

Ferron et al., "Oral bioavailability of pantoprazole suspended in sodium bicarbonate solution," Am. J. Health Syst. Pharm. 60(13):1324-1329 (2003).
Ferté et al., "Molecular circuits of solid tumors: prognostic and predictive tools for bedside use," Nat. Rev. Clin. Oncol. 7(7):367-380 (2010) (Epub Jun. 15, 2010).
Firoozinia et al., "PIK3CA gene amplification and PI3K p110α protein expression in breast carcinoma," Int. J. Med. Sci. 11(6):620-625 (2014).
Fitch et al., "Genetics of dark skin in mice," Genes Dev. 17(2):214-228 (2003).
Fleming et al., "Nitrile-containing pharmaceuticals: efficacious roles of the nitrile pharmacophore," J. Med. Chem. 53(22)7902-7917 (2010) (Epub Aug. 30, 2010).
Fleming et al., "Phase II trial of temsirolimus in patients with metastatic breast cancer," Breast Cancer Res. Treat. 136(2):355-363 (2012) (Epub Jan. 13, 2012).
Folkman, "Angiogenesis in cancer, vascular, rheumatoid and other disease," Nat. Med. 1(1):27-31 (1995).
Frederick et al., "Epithelial to mesenchymal transition predicts gefitinib resistance in cell lines of head and neck squamous cell carcinoma and non-small cell lung carcinoma," Mol. Cancer Ther. 6(6):1683-1691 (2007) (Epub May 31, 2007).
Früh, "The search for improved systemic therapy of non-small cell lung cancer—what are today's options?" Lung Cancer 72(3):265-270 (2011) (Epub Apr. 14, 2011).
Fry, "Inhibition of the epidermal growth factor receptor family of tyrosine kinases as an approach to cancer chemotherapy: progression from reversible to irreversible inhibitors," Pharmacol. Ther. 82(2-3):207-218 (1999).
Fukuoka et al., "Multi-institutional randomized phase II trial of gefitinib for previously treated patients with advanced non-small-cell lung cancer (The IDEAL 1 Trial) [corrected]," J. Clin. Oncol. 21(12):2237-2246 (2003) (Epub May 14, 2003).
Gadji et al., "EGF receptor inhibitors in the treatment of glioblastoma multiform: old clinical allies and newly emerging therapeutic concepts," Eur. J. Pharmacol. 625(1-3):23-30 (2009) (Epub Oct. 18, 2009).
Gajria and Chandarlapaty, "HER2-amplified breast cancer: mechanisms of trastuzumab resistance and novel targeted therapies," Expert Rev. Anticancer Ther. 11(2):263-275 (2011).
Gajria et al., "Tolerability and Efficacy of Targeting Both mTOR and HER2 Signaling in Trastuzumab-Refractory HER2+ Metastatic Breast Cancer," San Antonio Breast cancer Symposium. Abstract P5-18-04 (2010).
Gao et al., "Controlled Release of a Contraceptive Steroid From Biodegradable and Injectable Gel Formulations: in Vitro Evaluation," Pharm. Res. 12:857-863 (1995).
Garcia et al., "Promoter Methylation of the PTEN Gene is a Common Molecular Change in Breast Cancer," Genes Chromosomes Cancer 41(2):117-127 (2004).
Garrett and Arteaga, "Resistance to HER2-directed antibodies and tyrosine kinase inhibitors: mechanisms and clinical implications," Cancer Biol. Ther. 11(9):793-800 (2011) (Epub May 1, 2011).
Gatzemeier, "Second-Generation EGFR Inhibitors and Combinations," J. Thorac Oncol. 4(9): S121 (2009).
Gazdar, "Activating and Resistance Mutations of EGFR in Non-Small-Cell Lung Cancer: Role in Clinical Response to EGFR Tyrosine Kinase Inhibitors," Oncogene 28:S24-S31 (2009).
Genentech, Herceptin®—Product Literature, www.Genetech.com, Sep. 1998 Revised (Jun. 2014), pp. 1-35.
Gennaro (Ed.), Remington's Pharmaceutical Sciences, 17th Edition, Alfonso R. Gennaro, Mack Publishing Company, Easton, PA (1985).
Geuna et al., "Hitting multiple targets in HER2-positive breast cancer: proof of principle or therapeutic opportunity?" Expert Opin. Pharmacother. 12(4):549-565 (2011) (Epub Jan. 6, 2011).
Geyer et al., "Lapatinib plus capecitabine for HER2-positive advanced breast cancer," N. Engl. J. Med. 355(26):2733-2743 (2006).

Ghayad and Cohen, "Inhibitors of the PI3K/Akt/mTOR pathway: new hope for breast cancer patients," Recent Pat. Anticancer Drug Discov. 5(1):29-57 (2010).
Giaccone et al., "Gefitinib in combination with gemcitabine and cisplatin in advanced non-small-cell lung cancer: a phase III trial—INTACT 1," J. Clin. Oncol. 22(5):777-784 (2004).
Giamas et al., "Kinases as Targets in the Treatment of Solid Tumors," Cell. Signal. 22(7):984-1002 (2010) (Epub Jan. 21, 2010).
Gilmer et al., "Impact of common epidermal growth factor receptor and HER2 variants on receptor activity and inhibition by lapatinib," Cancer Res. 68(2):571-579 (2008).
Glaxosmithkline, TYKERB Prescription Label, 2010, pp. 1-25.
Glück, "Chemotherapy Regimens in Metastatic Breast Cancer," Clin. Adv. Hematol. Oncol. 9(1):47-48 (2011).
Godin-Heymann et al., "Oncogenic activity of epidermal growth factor receptor kinase mutant alleles is enhanced by the T790M drug resistance mutation," Cancer Res. 67(15):7319-7326 (2007).
Godin-Heymann et al., "The T790M "gatekeeper" mutation in EGFR mediates resistance to low concentrations of an irreversible EGFR inhibitor," Mol. Cancer Ther. 7(4):874-879 (2008).
Goldhirsch et al., "2 years versus 1 year of adjuvant trastuzumab for HER2-positive breast cancer (HERA): an open-label, randomised control trail," Lancet 382:1021-1028 (2013).
Good, "A Comparison of Contact Angle Interpretations," J. Colloid Interface Sci. 44(1):63-71 (1973).
Govindan, "A review of epidermal growth factor receptor/HER2 inhibitors in the treatment of patients with non-small-cell lung cancer," Clin. Lung Cancer 11(1):8-12 (2010).
Greenberger et al., "EKB-569: a New Irreversible Inhibitor of Epidermal Growth Factor Receptor Tyrosine Kinase for the Treatment of Cancer," Clin. Cancer Res. 6(Suppl):4544s Abstr. 388 (2000).
Greulich et al., "Oncogenic Transformation by Inhibitor-Sensitive and -Resistant EGFR Mutants," PLOS Medicine 2(11) E313:1167-1176 (2005).
Gridelli et al., "Erlotinib in the Treatment of Non-small Cell Lung Cancer: Current Status and Future Developments," Anticancer Res. 30:1301-1310 (2010).
Grimm et al., "Diagnostic and Therapeutic Use of Membrane Proteins in Cancer Cells," Curr. Med. Chem. 18(2):176-190 (2011).
Guarneri et al., "Anti-HER2 neoadjuvant and adjuvant therapies in HER2 positive breast cancer," Cancer Treat. Rev. 36 Suppl 3:S62-S66 (2010).
Guertin et al., "Ablation in mice of the mTORC components raptor, rictor, or mLST8 reveals that mTORC2 is required for signaling to Akt-FOXO and PKCalpha, but not S6K1," Dev. Cell. 11(6):859-871 (2006).
Gullick et al., "Expression of epidermal growth factor receptors on human cervical, ovarian, and vulval carcinomas," Cancer Res. 46(1):285-292 (1986).
Hager et al., "PTEN expression in renal cell carcinoma and oncocytoma and prognosis," Pathology 39(5):482-485 (2007) (Abstract Only).
Hammerman et al., "Resistance to Epidermal Growth Factor Receptor Tyrosine Kinase Inhibitors in Non-Small Cell Lung Cancer," Clin. Cancer Res. 15(24):7502-7509 (2009).
Harris et al., "c-erbB-2 in serum of patients with breast cancer," Int. J. Biol. Markers 14(1):8-15 (1999).
Hasselblatt, "Ependymal Tumors," Recent Results Cancer Res. 171:51-66 (2009).
Hawkins and Grunberg, "Chemotherapy-Induced Nausea and Vomiting: Challenges and Opportunities for Improved Patient Outcomes," Clin. J. Oncol. Nurs. 13(1):54-64 (2009).
Hegedus et al., "Interaction of ABC multidrug transporters with anticancer protein kinase inhibitors: substrates and/or inhibitors?" Curr. Cancer Drug Targets 9(3):252-272 (2009).
Heigener and Reck, "Mutations in the epidermal growth factor receptor gene in non-small cell lung cancer: Impact on treatment beyond gefitinib and erlotinib," Adv. Ther. 28(2):126-133 (2011) (Epub Dec. 16, 2010).
Heigener, "Non-Small Cell Lung Cancer in Never-Smokers: a New Disease Entity?" Onkologie 34(4):202-207 (2011) (EpubMar. 18, 2011).

(56) References Cited

OTHER PUBLICATIONS

Heist et al., "A phase II study of oxaliplatin, pemetrexed, and bevacizumab in previously treated advanced non-small cell lung cancer," J. Thorac. Oncol. 3(10):1153-1158 (2008).
Herbst et al., "Gefitinib in Combination with Paclitaxel and Carboplatin in Advanced Non-Small-Cell Lung Cancer: a Phase III Trial—INTACT 2," J. Clin. Oncol. 22(5):785-794 (2004).
Herbst et al., "Selective oral epidermal growth factor receptor tyrosine kinase inhibitor ZD1839 is generally well-tolerated and has activity in non-small-cell lung cancer and other solid tumors: results of a phase I trial," J. Clin. Oncol. 20(18):3815-3825 (2002).
Heymach et al., "Epidermal growth factor receptor inhibitors in development for the treatment of non-small cell lung cancer," Clin. Cancer Res. 12(14 Pt 2):4441s-4445s (2006).
Higa et al., "Biological considerations and clinical applications of new HER2-targeted agents," Expert Rev. Anticancer Ther. 10(9):1497-1509 (2010).
Ho and Laskin, "EGFR-directed therapies to treat non-small-cell lung cancer," Expert Opin. Investig. Drugs 18(8):1133-1145 (2009).
Holbro and Hynes, "ErbB receptors: directing key signaling networks throughout life," Annu. Rev. Pharmacol. Toxicol. 44:195-217 (2004).
Holodov and Yakovlev, Clinical Pharmacokinetics, Moscow, Medicine, (1985), pp. 83-98, 134-138, 160, 378-380 (English translation not available).
Hookes and Lakeram, "American Chemical Society—235th National Meeting. Part 2: EGFR kinase inhibitors and β3-lactamases under investigation by Wyeth" Idrugs 11(6):391-393 (2008).
Horn and Sandler, "Epidermal growth factor receptor inhibitors and antiangiogenic agents for the treatment of non-small cell lung cancer," Clin. Cancer Res. 15(16):5040-5048 (2009) (Epub Aug. 11, 2009).
Hou and Kumamoto, "Flavonoids as protein kinase inhibitors for cancer chemoprevention: direct binding and molecular modeling," Antioxid. Redox Signal. 13(5):691-719 (2010).
Huang et al., "Up-regulation of miR-21 by HER2/neu signaling promotes cell invasion," J. Biol. Chem. 284(27):18515-18524 (2009) (Epub May 6, 2009).
Hubalek et al., "Resistance to HER2-targeted therapy: mechanisms of trastuzumab resistance and possible strategies to overcome unresponsiveness to treatment," Wien. Med. Wochenschr. 160(19-20):506-512 (2010) (Epub Oct. 26, 2010).
Huber et al., "Pharmacokinetics of pantoprazole in man," Int. J. Clin. Pharmacol. Ther. 34(5):185-194 (1996).
Hug et al., "A single-dose, crossover, placebo- and moxifloxacin-controlled study to assess the effects of neratinib (HKI-272) on cardiac repolarization in healthy adult subjects," Clin. Cancer Res. 16(15):4016-4023 (2010) (Epub Jul. 20, 2010).
Hung and Lau, "Basic Science of HER-2/neu: a review," Semin. Oncol. 26(4 Suppl 12):51-59 (1999).
Hungarian Intellectual Property Office Search Report for Hungarian Patent Application No. 201002712-6 (dated Aug. 4, 2011).
Hynes and Lane, "ERBB Receptors and Cancer: the Complexity of Targeted Inhibitors," Nat. Rev. Cancer 5(5):341-354 (2005).
Ich Expert Working Group: "Impurities in New Drug Substances Q3A (R2)," International Conference on Harmonisation of Technical Requirements for Registration of Pharmaceuticals for Human Use (Online) 2006.
Ikediobi, "Somatic Pharmacogenomics in Cancer," Pharmacogenomics J. 8(5):305-314 (2008) (Epub Aug. 5, 2008).
Ikezoe et al., "Effect of SU11248 on gastrointestinal stromal tumor-T1 cells: enhancement of growth inhibition via inhibition of 3-kinase/Akt/mammalian target of rapamycin signaling," Cancer Sci. 97(9):945-951 (2006).
Ikezoe et al., "The Anti-Tumor Effects of SU11248, a Class III Receptor Tyrosine Kinase Inhibitor, Against a Variety of Human Hematological Malignancies," Blood (ASH Annual Meeting Abstracts) 106: Abstract 2795 (2005).
Ilango et al., "Investigation of Colon Specificity of Novel Polysaccharide-Okra Mucilage-Film Coated with Enteric Materials," Int. J. Pharma. Bio. Sci. 3(2):52-62 (2012).
Iliadis et al., "APIS: a software for model identification, simulation and dosage regimen calculations in clinical and experimental pharmacokinetics," Computer Methods Programs Biomed. 38(4):227-239 (1992).
Intellectual Property Office of Singapore Examination Report for Singapore Patent Application No. 2013046099 (dated Jan. 21, 2016).
Intellectual Property Office of Singapore Written Opinion for Singapore Patent Application No. 2013046099 (dated Jun. 4, 2015).
International Preliminary Report on Patentability Chapter 1 for International Application No. PCT/US2009/047643 dated Dec. 18, 2010.
International Search Report for International Application No. PCT/US2008/080130, dated Apr. 5, 2009.
International Search Report for International Patent Application No. PCT/US2009/047643, dated Jan. 28, 2010.
Isakoff and Baselga, "Trastuzumab-DM1: building a chemotherapy-free road in the treatment of human epidermal growth factor receptor 2-positive breast cancer," J. Clin. Oncol. 29(4):351-354 (2011) (Epub Dec. 20, 2010).
Ito et al., "A Phase 1 Study of Neratinib (HKI-272) in Combination with Paclitaxel in Japanese Patients with Solid Tumors," Ann. Oncol. 21 (Suppl 8):viii103 Abstr. 298P (2010).
Ito et al., "Tolerability and safety of oral neratinib (HKI-272) in Japanese patients with advanced solid tumors," J. Clin. Oncol. 27:(suppl; abstr. e14505) (2009).
Jackisch, "Challenges in the treatment of ErbB2 (HER2)-positive breast cancer," EJC Suppl. 6(5):7-14 (2008).
Jahanzeb et al., "Phase II trial of weekly vinorelbine and trastuzumab as first-line therapy in patients with HER2+ metastatic breast cancer," Oncologist 7(5):410-417 (2002).
Jallal et al., "A Src/Abl kinase inhibitor, SKI-606, blocks breast cancer invasion, growth, and metastasis in vitro and in vivo," Cancer Res. 67(4):1580-1588 (2007).
Janczuk and Bialopiotrowicz, "Surface Free-Energy Components of Liquids and Low Energy Solids and Contact Angles," J. Colloid Interface Sci. 127(1):189-204 (1989).
Jänne et al., "Phase I dose-escalation study of the pan-HER inhibitor, PF299804, in patients with advanced malignant solid tumors," Clin. Cancer Res. 17(5):1131-1139 (2011) (Epub Jan. 10, 2011).
Jänne, "Challenges of detecting EGFR T790M in gefitinib/erlotinib-resistant tumours," Lung Cancer 60 Suppl 2:S3-S9 (2008).
Japanese Official Action for Corresponding Japanese Patent Application No. 2010-258729, dated Apr. 12, 2013.
Japanese Official Action dated Sep. 17, 2013, for Japanese Patent Application No. 2011-289220.
Jasper, "The Surface Tension of Pure Liquid Compounds," J. Phys. Chem. Ref. Data 1:841 (1972).
Jelliffe et al., "Adaptive control of drug dosage regimens: basic foundations, relevant issues, and clinical examples," Int. J. Biomed. Comput. 36(1-2):1-23 (1994).
Ji et al., "Epidermal growth factor receptor variant III mutations in lung tumorigenesis and sensitivity to tyrosine kinase inhibitors," Proc. Natl. Acad. Sci. U.S.A. 103(20):7817-7822 (2006) (Epub May 3, 2006).
Ji et al., "The impact of human EGFR kinase domain mutations on lung tumorigenesis and in vivo sensitivity to EGFR-targeted therapies," Cancer Cell. 9(6):485-495 (2006) (Epub May 25, 2006).
Jimeno and Hidalgo, "Pharmacogenomics of epidermal growth factor receptor (EGFR) tyrosine kinase inhibitors," Biochim. Biophys. Acta 1766(2):217-229 (2006) (Epub Sep. 12, 2006).
Johnson et al., "Cisplatin and Its Analogues," Cancer Principles & Practice of Oncology, 6th Edition, Ed. Devita, V.T., Hellman, S., Rosenberg, S.A, Lippincott Williams & Wilkins Philadelphia, 2001, p. 376-388.
Johnson et al., "Impact of EGFR mutations on treatment of non-small cell lung cancer," Cancer Chemother. Pharmacol. 58(Suppl1): s5-s9 (2006).

(56) References Cited

OTHER PUBLICATIONS

Johnson et al., "Strategies for discovering and derisking covalent, irreversible enzyme inhibitors," Future Med. Chem. 2(6):949-964 (2010).
Johnson, "Biomarkers of Lung Cancer Response to EGFR-TKI," EJC Suppl. 5(8):14-15 Abstr. S23 (2007).
Johnson, "Protein kinase inhibitors: contributions from structure to clinical compounds," Q. Rev. Biophys. 42(1):1-40 (2009) (Epub Mar. 19, 2009).
Jones and Buzdar, "Evolving Novel Anti-HER2 Strategies," Lancet Oncol. 10(12):1179-1187 (2009).
Jones, "Adaptive trials receive boost," Nat. Rev. Drug Discov. 9(5):345-348 (2010) (Epub Apr. 23, 2010).
Jones, "HER4 intracellular domain (4ICD) activity in the developing mammary gland and breast cancer," J. Mammary Gland Biol. Neoplasia 13(2):247-258 (2008) (Epub May 13, 2008).
Jorissen et al., "Epidermal growth factor receptor: mechanisms of activation and signalling," Exp. Cell. Res. 284(1):31-53 (2003).
Joshi and Kucherlapati, "Pharmacogenomics of lung cancer: with a view to address EGFR-targeted therapies," Pharmacogenomics 8(9):1211-1220 (2007).
Kamath and Buolamwini, "Targeting EGFR and HER-2 receptor tyrosine kinases for cancer drug discovery and development," Med. Res. Rev. 26(5):569-594 (2006).
Kane, "Cancer Therapies Targeted to the Epidermal Growth Factor Receptor and Its Family Members," Expert Opin. Ther. Pat. 16(2):147-164 (2006).
Kaplan and Meier, "Nonparametric Estimation From Incomplete Observations," J. Am. Stat. Assoc. 53:457-481 (1958).
Katakami et al., "LUX-Lung 4: a phase II trial of afatinib in patients with advanced non-small-cell lung cancer who progressed during prior treatment with erlotinib, gefitinib, or both," J. Clin. Oncol. 31(27):3335-3341 (2013) (Epub Jul. 1, 2013).
Katzel et al., "Recent advances of novel targeted therapy in non-small cell lung cancer," J Hematol. Oncool. 2:2 (2009).
Kennedy et al., "Novel Agents in the Management of Lung Cancer," Curr. Med. Chem. 17(35):4291-4325 (2010).
Kim et al., "Chasing targets for EGFR tyrosine kinase inhibitors in non-small-cell lung cancer: Asian perspectives," Expert Rev. Mol. Diagn.7(6):821-836 (2007).
Kim et al., "The role of HER-2 oncoprotein in drug-sensitivity in breast cancer (Review)," Oncol. Rep. 9(1):3-9 (2002).
Klein and Levitzki, "Targeting the EGFR and the PKB Pathway in Cancer," Curr. Opin. Cell. Biol. 21(2):185-193 (2009) (Epub Feb. 11, 2009).
Klüter et al., "Characterization of irreversible kinase inhibitors by directly detecting covalent bond formation: a tool for dissecting kinase drug resistance," ChemBioChem 11(18):2557-2566 (2010).
Kobayashi et al., "EGFR mutation and resistance of non-small-cell lung cancer to gefitinib," N. Engl. J. Med. 352(8):786-792 (2005).
Kotteas et al., "Targeted therapy for nonsmall cell lung cancer: focusing on angiogenesis, the epidermal growth factor receptor and multikinase inhibitors," Anticancer Drugs 21(2):151-168 (2010).
Kris et al., "Efficacy of gefitinib, an inhibitor of the epidermal growth factor receptor tyrosine kinase, in symptomatic patients with non-small cell lung cancer: a randomized trial," JAMA 290(16):2149-2158 (2003).
Krop, "Managing Trastuzumab-resistant Breast Cancer," Clin. Adv. Hematol. Oncol. 7(2):108-110 (2009).
Kulke et al., "Capecitabine Plus Erlotinib in Gemcitabine-Refractory Advanced Pancreatic Cancer," J. Clin. Oncol. 25(30):4787-4792 (2007).
Kuznar, "New Small Molecule Added to Trastuzumab Improves Survival in Metastatic Disease," Am. Health Drug Benefits 2(5):27 (2009).
Kwak et al., "Irreversible inhibitors of the EGF receptor may circumvent acquired resistance to gefitinib," Proc. Natl. Acad. Sci. U.S.A. 102(21):7665-7670 (2005) (Epub May 16, 2005).

La Motta et al., "Computational studies of epidermal growth factor receptor: docking reliability, three-dimensional quantitative structure-activity relationship analysis, and virtual screening studies," J. Med. Chem. 52(4):964-975 (2009).
Laack et al., "Lessons learnt from gefitinib and erlotinib: Key insights into small-molecule EGFR-targeted kinase inhibitors in non-small cell lung cancer," Lung Cancer 69(3):259-264 (2010) (Epub Jun. 19, 2010).
Lam and Mok, "Targeted Therapy: An Evolving World of Lung Cancer," Respirology 16(1):13-21 (2011) (Epub Aug. 16, 2010).
Langdon et al., "Pertuzumab—Humanized anti-HER2 monoclonal antibody HER dimerization inhibitor oncolytic," Drugs Future 33(2):123-130 (2008).
Langer and Soria, "The role of anti-epidermal growth factor receptor and anti-vascular endothelial growth factor therapies in the treatment of non-small-cell lung cancer," Clin. Lung Cancer 11(2):82-90 (2010).
Langlois et al., "Application of a modification of the Polonovski reaction to the synthesis of vinblastine-type alkaloids," J. Am. Chem. Soc. 98(22):7017-7024 (1976).
Lapatinib and Vinorelbine in Treating Patients with Advanced Solid Tumors, clinicaltrials.gov, [Online], U.S. National Institutes of Health, May 26, 2008, [Retrieved on Aug. 30, H-25 (2013)], obtained from the Internet, URL, http://clinicaltrials.gov/archive/NCT00389922/2008_05_26.
Lapatinib and Vinorelbine in Treating Women With HER2-Overexpressing Locally Advanced or Metastatic Breast Cancer, http://clinicaltrials.gov, [Online], U.S. National Institutes of Health, May 26, 2008, [Retrieved on Aug. 30, H-25 (2013)], obtained from the Internet, URL, http://clinicaltrials.gov/archive/NCT00513058/2008_05_26.
Lee et al., "Lung Cancer in Never Smokers: Change of a Mindset in the Molecular Era," Lung Cancer 72(1):9-15 (2011) (Epub Jan. 26, 2011).
Lee et al., "Phase II Study of Vinorelbine Plus Trastuzumab in HER2 Overexpressing Metastatic Breast Cancer Pretreated with Anthracyclines and Taxanes," J. Breast Cancer 14(2):140-146 (2011).
Leone and Dudek, "Enzyme replacement therapy for Gaucher's disease in patient treated for non-small cell lung cancer," Anticancer Res. 28(6B):3937-3939 (2008).
Levitzki and Mishani, "Tyrphostins and other tyrosine kinase inhibitors," Annu Rev. Biochem. 75:93-109 (2006).
Li and Perez-Soler, "Skin toxicities associated with epidermal growth factor receptor inhibitors," Target. Oncol. 4(2):107-119 (2009) (Epub May 19, 2009).
Li and Sun, "PTEN/MMAC1/TEP1 suppresses the tumorigenicity and induces G1 cell cycle arrest in human glioblastoma cells," Proc. Natl. Acad. Sci. U.S.A. 95(26):15406-15411 (1998).
Li and Sun, "TEP1, encoded by a candidate tumor suppressor locus, is a novel protein tyrosine phosphatase regulated by transforming growth factor β," Cancer Res. 57(11):2124-2129 (1997).
Li et al., "BIBW2992, an irreversible EGFR/HER2 inhibitor highly effective in preclinical lung cancer models," Oncogene 27(34):4702-4711 (2008) (Epub Apr. 14, 2008).
Li et al., "Bronchial and peripheral murine lung carcinomas induced by T790M-L858R mutant EGFR respond to HKI-272 and rapamycin combination therapy," Cancer Cell 12(1):81-93 (2007).
Li et al., "PTEN, a putative protein tyrosine phosphatase gene mutated in human brain, breast, and prostate cancer," Science 275(5308):1943-1947 (1997).
Ligibel and Winer, "Trastuzumab/chemotherapy combinations in metastatic breast cancer," Semin. Oncol. 29(3 Suppl 11):38-43 (2002).
Limentani et al., "Safety and Efficacy of Neratinib (HKI-272) in Combination with Vinorelbine in Patients with Solid Tumors," J. Clin. Oncol. (Meeting Abstracts) 27(15S):e14554 (2009).
Lin and Winer, "Chemotherapy agents in human epidermal growth factor receptor 2-positive breast cancer: time to step out of the limelight," J. Clin. Oncol. 29(3):251-253 (2011) (Epub Dec. 13, 2010).

(56) References Cited

OTHER PUBLICATIONS

Lin and Yang, "Epidermal growth factor receptor tyrosine kinase inhibitors in elderly or poor performance status patients with advanced non-small cell lung cancer," Target. Oncol. 4(1):37-44 (2009) (Epub Jan. 20, 2009).

Linardou et al., "Somatic EGFR mutations and efficacy of tyrosine kinase inhibitors in NSCLC," Nat. Rev. Clin. Oncol. 6(6):352-366 (2009).

Little, "Molecular Tests, Targets and Therapies for Cancer," EPC (DIA 43rd Annual Meeting Edition) p. 98 (2007).

Liu et al., "Targeting epidermal growth factor receptor in lung cancer: Perspective from the Asia-Pacific region," Asia-Pac. J. Clin. Oncol. 2:22-31 (2006).

Locker et al., "ASCO 2006 update of recommendations for the use of tumor markers in gastrointestinal cancer," J. Clin. Oncol. 24(33):5313-5327 (2006) (Epub Oct. 23, 2006).

Loew et al., "The epidermal growth factor receptor as a therapeutic target in glioblastoma multiforme and other malignant neoplasms," Anticancer Agents Med. Chem. 9(6):703-715 (2009).

Loke, "Drug-drug interactions—bridging the gulf between the bench and the bedside?" Br. J. Clin. Pharmacol. 71(4):485-486 (2011).

LoPiccolo et al., "Targeting the PI3K/Akt/mTOR pathway: effective combinations and clinical considerations," Drug Resist. Updat. 11(1-2):32-50 (2008) (Epub Dec. 31, 2007).

Loriot et al., "Drug insight: gastrointestinal and hepatic adverse effects of molecular-targeted agents in cancer therapy," Nat. Clin. Pract. Oncol. 5(5):268-278 (2008) (Epub Mar. 18, 2008).

Loriot et al., "Pemetrexed-induced pneumonitis: a case report," Clin. Lung Cancer 10(5):364-366 (2009).

Lorusso and Eder, "Therapeutic potential of novel selective-spectrum kinase inhibitors in oncology," Expert Opin. Investig. Drugs 17(7):1013-1028 (2008).

Lou et al., "Progress in Target Therapy for Breast Cancer," J. Oncology 15(9):788-795 (2009). (English Abstract).

Lu and Ku, "Preformulation stability study of the EGFR inhibitor HKI-272 (Neratinib) and mechanism of degradation," Drug Dev. Ind. Pharm. 1-7 (2011).

Lu et al., "The PTEN/MMAC1/TEP tumor suppressor gene decreases cell growth and induces apoptosis and anoikis in breast cancer cells," Oncogene 18(50):7034-7045 (1999).

Luetteke et al., "The mouse waved-2 phenotype results from a point mutation in the EGF receptor tyrosine kinase," Genes Dev. 8(4):399-413 (1994).

Lynch et al., "Activating mutations in the epidermal growth factor receptor underlying responsiveness of non-small-cell lung cancer to gefitinib," N. Engl. J. Med. 350(21):2129-2139 (2004) (Epub Apr. 29, 2004).

Lynch et al., "Novel Agents in the Treatment of Lung Cancer: Fourth Cambridge Conference," Clin. Cancer Res. 13(15 Suppl.):4583s-4588s (2007).

Lynch et al., "Summary statement novel agents in the treatment of lung cancer: Fifth Cambridge Conference assessing opportunities for combination therapy," J. Thorac. Oncol. 3(6 Suppl 2): S107-S112 (2008).

Lynch, "Molecular Staging of NSCLC: 2006," EJC (Suppl 4):24-25 Abstr. S55 (2006).

Ma et al., "PIK3CA as an oncogene in cervical cancer," Oncogene 19(23):2739-2744 (2000).

Macrinici and Romond, "Clinical updates on EGFR/HER targeted agents in early-stage breast cancer," Clin. Breast Cancer 10 Suppl 1:E38-E46 (2010).

Maehama et al., "A sensitive assay for phosphoinositide phosphatases," Anal. Biochem. 279(2):248-250 (2000).

Maehama et al., "PTEN and myotubularin: novel phosphoinositide phosphatases," Annu. Rev. Biochem. 70:247-279 (2001).

Maehama, "PTEN: its deregulation and tumorigenesis," Biol. Pharm. Bull. 30(9):1624-1627 (2007).

Mallon et al., "Antitumor efficacy of PKI-587, a highly potent dual PI3K/mTOR kinase inhibitor," Clin. Cancer Res. 17(10):3193-3203 (2011) (Epub Feb. 15, 2011).

Man et al., "New and established targets for the treatment of breast cancer," Adv. Breast Cancer 7(3):10-13 (2010).

Mangeney et al., "5'-Nor anhydrovinblastine : Prototype of a new class of vinblastine derivatives," Tetrahedron 35(18):2175-2179 (1979).

Mantel and Haenszel, "Statistical aspects of the analysis of data from retrospective studies of disease," J. Natl. Cancer Inst. 22(4):719-748 (1959).

Martinez-Garcia et al., "Tyrosine Kinase Inhibitors in Breast Cancer: Present Status and Perspectives," Cancer Chemother. Rev. 186-194 (2010).

Mattsson and Clowes, "Current concepts in restenosis following balloon angioplasty," Trends Cardiovasc. Med. 5(5):200-204 (1995).

Mauriz and Gonzalez-Gallego, "Antiangiogenic drugs: current knowledge and new approaches to cancer therapy," J. Pharm. Sci. 97(10):4129-4154 (2008).

Mayer, "Treatment of HER2-positive metastatic breast cancer following initial progression," Clin. Breast Cancer 9 Suppl 2:S50-S57 (2009).

McDermott et al., "Acquired resistance of non-small cell lung cancer cells to MET kinase inhibition is mediated by a switch to epidermal growth factor receptor dependency," Cancer Res. 70(4):1625-1634 (2010) (Epub Feb. 2, 2010).

McDermott et al., "High-throughput lung cancer cell line screening for genotype-correlated sensitivity to an EGFR kinase inhibitor," Methods Enzymol. 438:331-341 (2008).

McDermott et al., "Identification of genotype-correlated sensitivity to selective kinase inhibitors by using high-throughput tumor cell line profiling," Proc. Natl. Acad. Sci. U.S.A. 104(50):19936-19941 (2007) (Epub Dec. 6, 2007).

Mcneil et al., "Two targets, one drug for new EGFR inhibitors," J. Natl. Cancer Inst. 98(16):1102-1103 (2006).

Mehta and Osipo, "Trastuzumab resistance: role for Notch signaling," ScientificWorldJournal 9:1438-1448 (2009).

Mendelsohn and Baselga, "The EGF receptor family as targets for cancer therapy," Oncogene 19(56):6550-6565 (2000).

Mendoza, "Targeted therapies in the treatment of advanced non-small-cell lung cancer: update," Klin.Onkol. 22(4):131-138 (2009).

Meng et al., "MicroRNA-21 regulates expression of the PTEN tumor suppressor gene in human hepatocellular cancer," Gastroenterology 133(2):647-658 (2007) (Epub May 21, 2007).

Metro and Cappuzzo, "New targeted therapies for non-small-cell lung cancer," Therapy 6(3):335-350 (2009).

Metzger-Filho et al., "Management of metastatic HER2-positive breast cancer progression after adjuvant trastuzumab therapy—current evidence and future trends," Expert Opin. Investig. Drugs 19 Suppl 1:S31-S39 (2010).

Metzger-Filho et al., "Molecular targeted therapy in prevalent tumors: learning from the past and future perspectives," Current Clin. Pharmacol. 5(3):166-177 (2010).

Meyerhardt et al., "Phase II study of capecitabine, oxaliplatin, and erlotinib in previously treated patients with metastastic colorectal cancer," J. Clin. Oncol. 24(12):1892-1897 (2006).

Minami et al., "The major lung cancer-derived mutants of ERBB2 are oncogenic and are associated with sensitivity to the irreversible EGFR/ERBB2 inhibitor HKI-272," Oncogene 26(34):5023-5027 (2007) (Epub Feb. 19, 2007).

Minkovsky and Berezov, "BIBW-2992, a dual receptor tyrosine kinase inhibitor for the treatment of solid tumors," Curr. Opin. Investig. Drugs 9(12):1336-1346 (2008).

Mitsudomi et al., "Biological and clinical implications of EGFR mutations in lung cancer," Int. J. Clin. Oncol. 11(3):190-198 (2006).

Moasser, "Targeting the function of the HER2 oncogene in human cancer therapeutics," Oncogene 26(46):6577-6592 (2007) (Epub May 7, 2007).

Morabito et al., "Methodological Issues of Clinical Research with EGFR Inhibitors," Curr. Cancer. Ther. Rev. 3(4):292-302 (2007).

Moreno-Aspitia and Perez, "Treatment options for breast cancer resistant to anthracycline and taxane," Mayo Clin. Proc. 84(6):533-545 (2009).

(56) References Cited

OTHER PUBLICATIONS

Morozova et al., "System-level analysis of neuroblastoma tumor-initiating cells implicates AURKB as a novel drug target for neuroblastoma," Clin. Cancer Res. 16(18):4572-4582 (2010) (Epub Jul. 22, 2010).
Morris and Hudis, "Personalizing therapy for metastatic breast cancer," Expert Rev. Anticancer. Ther. 9(9):1223-1226 (2009).
Morrow et al., "Recent advances in systemic therapy: Advances in systemic therapy for HER2-positive metastatic breast cancer," Breast Cancer Res. 11(4):207 (2009) (Epub Jul. 15, 2009).
Mukai, "Targeted therapy in breast cancer: current status and future directions," Jpn. J. Clin. Oncol. 40(8):711-716 (2010) (Epub Apr. 8, 2010).
Mukai, "Treatment strategy for HER2-positive breast cancer," Int. J. Clin. Oncol. 15(4):335-340 (2010) (Epub Jul. 15, 2010).
Mukherji and Spicer, "Second-generation epidermal growth factor tyrosine kinase inhibitors in non-small cell lung cancer," Expert Opin. Investig. Drugs 18(3):293-301 (2009).
Mullard, "2010 in Reflection," Nat. Rev. Drug Discov. 10:7-9 (2011).
Munagala et al., "Promising molecular targeted therapies in breast cancer," Indian J Pharmacol. 43(3):236-245 (2011).
Mundhenke et al., "Significance of Tyrosine Kinase Inhibitors in the Treatment of Metastatic Breast Cancer," Breast Care (Basel) 4(6):373-378 (2009) (Epub Nov. 16, 2009).
Murphy and Fornier, "HER2-positive breast cancer: beyond trastuzumab," Oncology (Williston Park) 24(5):410-415 (2010).
Muthuswamy, "Trastuzumab resistance: all roads lead to SRC," Nat. Med. 17(4):416-418 (2011).
Nagata et al., "PTEN activation contributes to tumor inhibition by trastuzumab, and loss of PTEN predicts trastuzumab resistance in patients," Cancer Cell vol. 6(2):117-127 (2004).
Nahta and O'Regan, "Evolving strategies for overcoming resistance to HER2-directed therapy: targeting the PI3K/Akt/mTOR pathway," Clin. Breast Cancer 10 Suppl 3:S72-S78 (2010).
Nakagawa et al., "Combined therapy with mutant-selective EGFR inhibitor and Met kinase inhibitor for overcoming erlotinib resistance in EGFR-mutant lung cancer," 11(10):2149-2157 (2012) (Epub Jul. 25, 2012).
Natoli et al., "Tyrosine kinase inhibitors," Curr. Cancer Drug Targets 10(5):462-483 (2010).
Nguyen et al., "Acquired resistance to epidermal growth factor receptor tyrosine kinase inhibitors in non-small-cell lung cancers dependent on the epidermal growth factor receptor pathway," Clin. Lung Cancer 10(4):281-289 (2009).
Nicholson et al., "EGFR and cancer prognosis," Eur. J. Cancer 37 Suppl 4:S9-S15 (2001).
Nielsen et al., "HER2-targeted therapy in breast cancer. Monoclonal antibodies and tyrosine kinase inhibitors," Cancer Treat Rev. 35(2):121-136 (2009) (Epub Nov. 12, 2008).
Nitz, "Perspectives: Other ErbB2-Targeted Therapies," Breast Care (Basel) 5(s1):25-27 (2010) (Epub Apr. 26, 2010).
Nolè et al., "Dose-finding and pharmacokinetic study of an all-oral combination regimen of oral vinorelbine and capecitabine for patients with metastatic breast cancer," Ann. Oncol. 17(2):322-329 (2006) (Epub Nov. 22, 2005).
O'Brien et al., "Activated phosphoinositide 3-kinase/AKT signaling confers resistance to trastuzumab but not lapatinib," Mol. Cancer Ther. 9(6):1489-1502 (2010) (Epub May 25, 2010).
Ocaña and Amir, "Irreversible pan-ErbB tyrosine kinase inhibitors and breast cancer: current status and future directions," Cancer Treat. Rev. 35(8):685-691 (2009) (Epub Sep. 4, 2009).
Ocaña and Pandiella, "Identifying breast cancer druggable oncogenic alterations: lessons learned and future targeted options," Clin. Cancer Res. 14(4):961-970 (2008).
Ocaña et al., "New Targeted Therapies in Head and Neck Cancer," Cancer Chemo. Rev. 4:35-43 (2009).
Ocaña et al., "Novel tyrosine kinase inhibitors in the treatment of cancer," Curr. Drug Targets 10(6):575-576 (2009).
Ocaña et al., "Preclinical development of molecular-targeted agents for cancer," Nat. Rev. Clin. Oncol. 8:200-209 (2011).
Office Action dated May 26, 2010 issued in corresponding European Patent Application No. 06836862.0.
Office Action dated Oct. 28, 2013 issued in corresponding Japanese Patent Application No. 2012-179873.
Office Action issued in corresponding Pakistan Patent Application No. 1456/2006 dated 2007.
Official Action and Search Report with English Translation, dated Jun. 18, 2013, for corresponding Chinese Application No. 201210328133.2.
Official Action from corresponding Japanese Application JP 2012-279650, dated Apr. 22, 2014 [along with an English Translation, received Jul. 16, 2014].
Oh et al., "Detection of epidermal growth factor receptor in the serum of patients with cervical carcinoma," Clin. Cancer Res. 6(12):4760-4763 (2000).
O'Hare et al., "Bcr-Abl kinase domain mutations and the unsettled problem of Bcr-AblT315I: looking into the future of controlling drug resistance in chronic myeloid leukemia," Clin. Lymphoma Myeloma 7 Suppl 3:S120-S130 (2007).
Okumura et al., "Induction of Noxa Sensitizes Human Colorectal Cancer Cells Expressing Mc1-1 to the Small-Molecule Bcl-2/Bcl-$x_L$ Inhibitor, ABT-737," Clin. Cancer Res. 14(24):8132-8142 (2008).
Omuro et al., "Lessons learned in the development of targeted therapy for malignant gliomas," Mol. Cancer Ther. 6(7):1909-1919 (2007).
O'Neil et al., (ed.). The Merck Index—An Encyclopedia of Chemicals, Drugs, and Biologicals. 13th Edition, Whitehouse Station, NJ: Merck and Co., Inc., 2001., p. 1454-1455.
Oshima, "Crystallization of Polymorphs and Pseudo-Polymorphs and Its Control," Pharm. Stage 6(10):48-53 (2007). [English Translation Not Available].
Ostro and Cullis, "Use of liposomes as injectable-drug delivery systems," Am. J. Hosp. Pharm. 46(8):1576-1587 (1989).
Ouchi et al., "Antitumor activity of erlotinib in combination with capecitabine in human tumor xenograft models," Cancer Chemother. Pharmacol. 57(5):693-702 (2006).
Pal et al., "Targeted therapies for non-small cell lung cancer: an evolving landscape," Mol. Cancer Ther. 9(7):1931-1944 (2010) (Epub Jun. 22, 2010).
Pallis et al., "Targeted therapies in the treatment of advanced/metastatic NSCLC," Eur. J. Cancer 45(14):2473-2487 (2009).
Pantuck et al., "Prognostic relevance of the mTOR pathway in renal cell carcinoma: implications for molecular patient selection for targeted therapy," Cancer 109(11):2257-2267 (2007).
Pao and Chmielecki, "Rational, biologically based treatment of EGFR-mutant non-small-cell lung cancer," Nat. Rev. Cancer 10(11):760-774 (2010) (Epub Oct. 22, 2010).
Pao, "Defining clinically relevant molecular subsets of lung cancer," Cancer Chemother. Pharmacol. 58(Suppl 1):s11-515 (2006).
Papaldo et al., "A phase II study on metastatic breast cancer patients treated with weekly vinorelbine with or without trastuzumab according to HER2 expression: changing the natural history of HER2-positive disease," Ann. Oncol. 17(4):630-636 (2006) (Epub Jan. 12, 2006).
Paridaens et al., "Neratinib (HKI-272), an irreversible pan-ErbB receptor tyrosine kinase inhibitor: Phase 2 results in patients with ErbB2+ advanced breast cancer," Ann. Oncol. 20(Suppl 2):ii61-ii62 Abstr. 186P (2009).
Parkin and Fernández, "Use of statistics to assess the global burden of breast cancer," Breast J. 12(Suppl 1):S70-S80 (2006).
Pegram et al., "Expert roundtable: emerging questions in ErbB2-positive breast cancer; Feb. 22, 2007," Clin. Breast Cancer 8(Suppl 3):S131-S141 (2008).
Pegram et al., "The molecular and cellular biology of HER2/neu gene amplification/overexpression and the clinical development of herceptin (trastuzumab) therapy for breast cancer," Cancer Treat. Res. 103:57-75 (2000).
Perez et al., "Updated Results of the Combined Analysis of NCCTG N9831 and NSABP B-31 Adjuvant Chemotherapy With/Without Trastuzumab in Patients with HER2-Positive Breast Cancer," J. Clin. Oncol. ASCO Annual Meeting Proc. 25(18S):512 (2007).

(56) References Cited

OTHER PUBLICATIONS

Pérez-Soler, "Individualized therapy in non-small-cell lung cancer: future versus current clinical practice," Oncogene 28(Suppl 1):S38-S45 (2009).
Pérez-Tenorio et al., "PIK3CA mutations and PTEN loss correlate with similar prognostic factors and are not mutually exclusive in breast cancer," Clin. Cancer Res. 13(12):3577-3584 (2007).
Perren et al., "Immunohistochemical evidence of loss of PTEN expression in primary ductal adenocarcinomas of the breast," Am. J. Pathol. 155(4):1253-1260 (1999).
Petter et al., "A novel small-molecule drug platform to silence cancer targets-application to the panErbB kinases," In: Proceedings of the 100th Annual Meeting of the American Association for Cancer Research; Apr. 18-22, 2009; Denver, CO. Abstr. 3746 (2009).
Pfister et al., "American Society of Clinical Oncology Clinical Practice Guideline for the Use of Larynx-Preservation Strategies in the Treatment of Laryngeal Cancer," J. Clin. Oncol. 24(22):3693-3704 (2006) (Epub Jul. 10, 2006).
Piccart et al., "Beyond trastuzumab: new anti-HER2 agents," Breast 20(Suppl 1):S1-52 Abstr. S02 (2011).
Piccart, "Circumventing de novo and acquired resistance to trastuzumab: new hope for the care of ErbB2-positive breast cancer," Clin. Breast Cancer 8(Suppl 3):S100-S113 (2008).
Plati et al., "Dysregulation of apoptotic signaling in cancer: molecular mechanisms and therapeutic opportunities," J. Cell. Biochem. 104(4):1124-1149 (2008).
Plosker and Keam, "Trastuzumab: a review of its use in the management of HER2-positive metastatic and early-stage breast cancer," Drugs 66(4):449-475 (2006).
Ponz-Sarvisé et al., "Epidermal growth factor receptor inhibitors in colorectal cancer treatment: what's new?" World J. Gastroenterol. 13(44):5877-5887 (2007).
Potashman and Duggan, "Covalent modifiers: an orthogonal approach to drug design," J. Med. Chem. 52(5):1231-1246 (2009).
Rabindran et al., "Antitumor activity of HKI-272, an orally active, irreversible inhibitor of the HER-2 tyrosine kinase," Cancer Res. 64(11):3958-3965 (2004).
Rabindran, "Antitumor activity of HER-2 inhibitors," Cancer Lett. 227(1):9-23 (2005) (Epub Dec. 15, 2004).
Raines and Ross, "Multiple growth factors are associated with lesions of atherosclerosis: specificity or redundancy?" Bioessays 18(4):271-282 (1996).
Rampaul et al., "Clinical value of epidermal growth factor receptor expression in primary breast cancer," Adv. Anat. Pathol. 12(5):271-273 (2005).
Rana and Swaby, "Targeted Therapies for HER2 Breast Cancer: A View of the Landscape," Curr. Breast Cancer Rep. 3:55-62 (2011).
Ranganathan and Muneer, "Highlights from: The 24th Annual Meeting of the American Association for Cancer Research; Los Angeles, CA; Apr. 14-18, 2007," Clin. Lung Cancer 8(6):359-363 (2007).
Rao, "Recent developments of collagen-based materials for medical applications and drug delivery systems," J. Biomater. Sci. Polym. Ed. 7(7):623-645 (1995).
Ray et al., "Lung cancer therapeutics that target signaling pathways: an update," Expert Rev. Respir. Med. 4(5):631-645 (2010).
Ray et al., "The role of EGFR inhibition in the treatment of non-small cell lung cancer," Oncologist 14(11):1116-1130 (2009) (Epub Nov. 5, 2009).
Redon et al., "A simple specific pattern of chromosomal aberrations at early stages of head and neck squamous cell carcinomas: PIK3CA but not p63 gene as a likely target of 3q26-qter gains," Cancer Res. 61(10):4122-4129 (2001).
Reid et al., "Dual inhibition of ErbB1 (EGFR/HER1) and ErbB2 (HER2/neu)," Eur. J. Cancer 43(3):481-489 (2007) (Epub Jan. 8, 2007).
Response filed by Applicant dated Apr. 30, 2009 to Office Action dated Jul. 18, 2008, in corresponding European Patent Application No. 06836862.0.
Rewcastle et al., "Synthesis of 4-(phenylamino)pyrimidine derivatives as ATP-competitive protein kinase inhibitors with potential for cancer chemotherapy," Curr. Org. Chem. 4(7):679-706 (2000).
Rexer et al., "Overcoming resistance to tyrosine kinase inhibitors: lessons learned from cancer cells treated with EGFR antagonists," Cell Cycle 8(1):18-22 (2009) (Epub Jan. 30, 2009).
Rich et al., "Phase II trial of gefitinib in recurrent glioblastoma," J. Clin. Oncol. 22(1):133-142 (2004) (Epub Nov. 24, 2003).
Riely et al., "Update on epidermal growth factor receptor mutations in non-small cell lung cancer," Clin. Cancer Res. 12(24):7232-7241 (2006).
Riely, "Second-generation epidermal growth factor receptor tyrosine kinase inhibitors in non-small cell lung cancer," J. Thorac. Oncol. 3(6 Suppl 2): S146-S149 (2008).
Rosell et al., "Age-related genetic abnormalities: the Achilles' heel for customizing therapy in elderly lung cancer patients," Personalized Medicine 4(1):59-72 (2007).
Rosell et al., "Screening for epidermal growth factor receptor mutations in lung cancer," N. Engl. J. Med. 361(10):958-967 (2009) (Epub Aug. 19, 2009).
Rosell et al., "Treatment of non-small-cell lung cancer and pharmacogenomics: where we are and where we are going," Curr. Opin. Oncol. 18(2):135-143 (2006).
Rosen et al., "Targeting signal transduction pathways in metastatic breast cancer: a comprehensive review," Oncologist 15(3):216-235 (2010) (Epub Mar. 3, 2010).
Ross et al., "The HER-2 receptor and breast cancer: ten years of targeted anti-HER-2 therapy and personalized medicine," Oncologist 14:320-368 (2009).
Rotella, "Medicinal Chemistry—XXth International Symposium. Lead finding strategies and kinase selectivity," IDrugs 11(11):774-778 (2008).
Roukos, "Trastuzumab and beyond: sequencing cancer genomes and predicting molecular networks," Pharmacogenomics J. 11(2):81-92 (2011) (Epub Oct. 26, 2010).
Roy and Perez, "Beyond trastuzumab: small molecule tyrosine kinase inhibitors in Her-2-positive breast cancer," Oncologist 14(11):1061-1069 (2009) (Epub Nov. 3, 2009).
Rubin et al., "10q23.3 loss of heterozygosity is higher in lymph node-positive (pT2-3,N+) versus lymph node-negative (pT2-3,N0) prostate cancer," Hum. Pathol. 31(4):504-508 (2000).
Rudloff and Samuels, "A growing family: adding mutated Erbb4 as a novel cancer target," Cell Cycle. 9(8):1487-1503 (2010) (Epub Apr. 15, 2010).
Saal et al., "PIK3CA mutations correlate with hormone receptors, node metastasis, and ERBB2, and are mutually exclusive with PTEN loss in human breast carcinoma," Cancer Res. 65(7):2554-2559 (2005).
Sakamoto et al., "Su-11248 Sugen," Curr. Opin. Investig. Drugs 5(12):1329-1339 (2004).
Salvesen et al., "Integrated genomic profiling of endometrial carcinoma associates aggressive tumors with indicators of PI3 kinase activation," Proc. Natl. Acad. Sci. U.S.A. 106(12):4834-4839. (2009) (Epub Mar. 4, 2009).
Samuels and Ericson, "Oncogenic PI3K and its role in cancer," Curr. Opin. Oncol. 18(1):77-82 (2006).
Sanchez-Martin and Pandiella, "Differential action of ErbB kinase inhibitors on receptor oligomerization," EJC Suppl. 8:107 Abstr. 337 (2010).
Santarpia et al., "Tyrosine kinase inhibitors for non-small-cell lung cancer: finding patients who will be responsive," Expert Rev. Respir. Med. (3):413-424 (2011).
Sartore-Bianchi et al., "Rationale and clinical results of multi-target treatments in oncology," Int. J. Biol. Markers 22(1 Suppl 4):S77-S87 (2007).
Sathornsumetee et al., "Malignant glioma drug discovery—targeting protein kinases," Expert Opin. Drug Discov. 2(1):1-17 (2007).
Sattler et al., "EGFR-targeted therapeutics: focus on SCCHN and NSCLC," ScientificWorldJournal 8:909-919 (2008).
Saura et al., "Safety of Neratinib (HKI-272) in Combination with Capecitabine in Patients with Solid Tumors: A Phase 1/2 Study," Cancer Res. 69(24 Suppl) Abstr. 5108 (2009).

(56) References Cited

OTHER PUBLICATIONS

Saura et al., "The safety of Neratinib (HKI-272) in Combination with Capecitabine in Patients with Solid Tumors: A Phase 1/2 Study," Ann. Oncol. 21(Suppl 4):iv63 Abstr. 147P (2010).
Saura et al., (Dec. 2011). Safety and Efficacy of Neratinib in Combination with Capecitabine in Patients with ErbB2-Positive Breast Cancer. Poster presented at the 2011 CTRC-AACR San Antonio Breast Cancer Symposium, San Antonio, Texas.
Scaltriti et al., "Expression of p95HER2, a truncated form of the HER2 receptor, and response to anti-HER2 therapies in breast cancer," J. Natl. Cancer Inst. 99(8):628-638 (2007).
Schiller et al., "Comparison of four chemotherapy regimens for advanced non-small-cell lung cancer," N. Engl. J. Med. 346(2):92-98 (2002).
Scott and Salgia, "Biomarkers in lung cancer: from early detection to novel therapeutics and decision making," Biomark. Med. 2(6):577-586 (2008).
Sebastian et al., "The complexity of targeting EGFR signalling in cancer: from expression to turnover," Biochim. Biophys. Acta. 1766(1):120-139 (2006) (Epub Jun. 23, 2006).
Sequist and Dziadziuszko, "Update on epidermal growth factor receptor inhibitor development in lung cancer," J. Thorac. Oncol. 1(7):740-743 (2006).
Sequist, "Second-generation epidermal growth factor receptor tyrosine kinase inhibitors in non-small cell lung cancer," Oncologist 12(3):325-330 (2007).
Settleman and Kurie, "Drugging the bad "AKT-TOR" to overcome TKI-resistant lung cancer," Cancer Cell 12(1):6-8 (2007).
Seyhan et al., "A genome-wide RNAi screen identifies novel targets of neratinib sensitivity leading to neratinib and paclitaxel combination drug treatments," Mol. Biosyst. 7(6):1974-1989 (2011) (Epub Apr. 12, 2011).
Sharma and Jayanth, "Neratinib, an irreversible erbB receptor tyrosine Kinase inhibitor, in patients with advanced erbB2-positive breast cancer," [commentary] Adv. Breast Cancer 7(1):21 (2010).
Sharma and Settleman, "Oncogene addiction: setting the stage for molecularly targeted cancer therapy," Genes Dev. 21(24):3214-3231 (2007).
Sharma et al., "Epidermal growth factor receptor mutations in lung cancer," Nat. Rev. Cancer7(3):169-181 (2007).
Sharma et al., "Receptor tyrosine kinase inhibitors as potent weapons in war against cancers," Curr. Pharm. Des. 15(7):758-776 (2009).
Shaw et al., "Pharmacological Inhibition of Restenosis: Learning From Experience," Trends Pharmacol. Sci. 16(12):401-404 (1995).
Shawver et al., "Receptor Tyrosine Kinases as Targets for Inhibition of Angiogenesis," Drug Discov. Today 2(2):50-63 (1997).
Shayesteh et al., "PIK3CA is implicated as an oncogene in ovarian cancer," Nat. Genet. 21(1):99-102 (1999).
Shimamura and Shapiro, "Heat shock protein 90 inhibition in lung cancer," J. Thorac. Oncol. 3(6 Suppl 2): S152-S159 (2008).
Shimamura et al., "Hsp90 inhibition suppresses mutant EGFR-T790M signaling and overcomes kinase inhibitor resistance," Cancer Res. 68(14):5827-5838 (2008).
Shimamura et al., "on-small-cell lung cancer and Ba/F3 transformed cells harboring the ERBB2 G776insV_G/C mutation are sensitive to the dual-specific epidermal growth factor receptor and ERBB2 inhibitor HKI-272," Cancer Res. 66(13):6487-6491 (2006).
Sibilia et al., "The epidermal growth factor receptor: from development to tumorigenesis," Differentiation 75(9):770-787 (2007).
Sigal, "Basic science for the clinician 48: tyrosine kinases in disease: the potential for inhibitors in the treatment of immunologic diseases," J. Clin. Rheumatol. 14(1):45-48 (2008).
Simon et al., "By 1023/SK&F 96022: biochemistry of a novel (H++K+)-ATPase inhibitor," Biochem Pharmacol. 39(11):1799-1806 (1990).
Singh et al., "Targeted covalent drugs of the kinase family," Curr. Opin. Chem. Biol. 14(4):475-480 (2010) (Epub Jul. 6, 2010).
Singh et al., "The resurgence of covalent drugs," Nat. Rev. Drug Discov. 10(4):307-317 (2011).
Slamon et al., "BCIRG 006: 2nd interim analysis phase III randomized trial comparing doxorubicin and cyclophosphamide followed by docetaxel (AC-T) with doxorubicin and cyclophosphamide followed by docetaxel and trastuzumab (AC-TH) with docetaxel, carboplatin and trastuzumab (TCH) in Her2neu positive early breast cancer patients," In: *San Antonio Breast Cancer Symposium*; 2006 [abstract 52].
Slamon et al., "Human breast cancer: correlation of relapse and survival with amplification of the HER-2/neu oncogene," Science 235(4785):177-182 (1987).
Smith et al. "2006 update of recommendations for the use of white blood cell growth factors: an evidence-based clinical practice guideline," J. Clin. Oncol. 24(19):3187-3205 (2006) (Epub May 8, 2006).
Smith et al., "2-year follow-up of trastuzumab after adjuvant chemotherapy in HER2-positive breast cancer: a randomised controlled trial." Lancet 369(9555):29-36 (2007).
Smith, "Goals of Treatment of Patients with Metastatic Breast Cancer," Semin. Oncol. 33:S2-S5 (2006).
Solca et al., "Beyond Trastuzumab. Second-Generation Targeted Therapies for HER-2-Positive Breast Cancer," Drugs for HER-2-positive Breast Cancer, Milestones in Drug Therapy, 2011 p. 91-107 (2011).
Specht and Gralow, "Neoadjuvant chemotherapy for locally advanced breast cancer," Semin. Radiat. Oncol. 9(4):222-228 (2009).
Spector et al., "Small Molecule HER-2 Tyrosine Kinase Inhibitors," Breast Cancer Res. 9(2):205 (2007).
Spector, "Treatment of metastatic ErbB2-positive breast cancer: options after progression on trastuzumab," Clin. Breast Cancer 8 Suppl 3:S94-S99 (2008).
Spicer and Rudman, "EGFR inhibitors in non-small cell lung cancer (NSCLC): the emerging role of the dual irreversible EGFR/HER2 inhibitor BIBW 2992," Target Oncol. 5(4):245-255 (2010) (Epub Jun. 24, 2010).
Srivastava et al., "Synthesis and structure-activity relationships of potent antitumor active quinoline and naphthyridine derivatives," Anticancer Agents Med. Chem. 7(6):685-709 (2007).
Staroslawska et al. (Dec. 2010). Safety and Efficacy of Neratinib (HKI-272) Plus Vinorelbine in the Treatment of Patients With ErbB2+ Metastatic Breast Cancer Pretreated With Anti-Her2 Therapy. Poster presented at teh 33rd Annual San Antonio Breast Cancer Symposium, San Antonio, Texas.
State Intellectual Property Office of the People's Republic of China Search Report for Chinese Patent Application No. 201210069340.0 (dated Dec. 11, 2015).
State Intellectual Property Office of the People's Republic of China Office Action for Chinese Patent Application No. 201210069340.0 (dated Dec. 21, 2015).
Stebbing et al., "Lemur tyrosine kinase-3 (LMTK3) in cancer and evolution," Oncotarget 2(6):428-429 (2011).
Steck et al., "Identification of a candidate tumour suppressor gene, MMAC1, at chromosome 10q23.3 that is mutated in multiple advanced cancers," Nat. Genet. 15(4):356-362 (1997).
Steins et al., "Targeting the epidermal growth factor receptor in non-small cell lung cancer," Onkologie 33(12):704-709 (2010) (Epub Nov. 26, 2010).
Stemke-Hale et al., "An integrative genomic and proteomic analysis of PIK3CA, PTEN, and AKT mutations in breast cancer," Cancer Res. 68(15):6084-6091 (2008).
Stockler et al., "Chemotherapy for advanced breast cancer—how long should it continue?" Breast Cancer Res. Treat. 81(Suppl. 1):S49-S52 (2003).
Stokoe et al., "Dual role of phosphatidylinositol-3,4,5-trisphosphate in the activation of protein kinase B," Science 277(5325):567-570 (1997).
Sugiyama, "Drug Transporters: Roles in New Drug Discovery and Development," Drug Metab. Rev. 42(S1):1-323 (2010).
Suzuki et al., "Combination of trastuzumab and vinorelbine in metastatic breast cancer," Jpn. J. Clin. Oncol. 33(10):514-517 (2003).
Swaby et al., "Neratinib in combination with trastuzumab for the treatment of advanced breast cancer: A phase I/II study," J. Clin. Oncol. 27:15s(suppl; abstr 1004) (2009).

(56) References Cited

OTHER PUBLICATIONS

Tagliabue et al., "HER2 as a target for breast cancer therapy," Expert Opin. Biol. Ther. 10(5):711-724 (2010).
Takada, "API Form Screening and Selection in Drug Discovery Stage," Pharm Stage 6(10):20-25 (2007). [English Translation Not Available].
Tejpar et al., "Phase 1/2a study of EKB-569, an irreversible inhibitor of epidermal growth factor receptor, in combination with 5-fluorouracil, leucovorin, and oxaliplatin (FOLFOX-4) in patients with advanced colorectal cancer (CRC)," J. Clin. Oncol. 22(14S):264s Abstr. 3579 (2004).
Test Procedures and Acceptance Criteria for New Drug Substances and New Drug Products; Pharmaceutical Affairs Bureau Notification No. 568; 2001 [English Translation Not Available].
Therasse et al., "New guidelines to evaluate the response to treatment in solid tumors. European Organization for Research and Treatment of Cancer, National Cancer Institute of the United States, National Cancer Institute of Canada," J. Natl. Cancer Inst. 92(3):205-216 (2000).
Tjin Tham Sjin et al., "Design of a novel covalent EGFR mutant-selective inhibitor," EJC Suppl. 8(7):31 Abstr. 73 (2010).
Toffoli et al., "Pharmacology of epidermal growth factor inhibitors," Int. J. Biol. Markers 22(1 Suppl 4):S24-S39 (2007).
Tolaney and Krop, "Mechanisms of trastuzumab resistance in breast cancer," Anticancer Agents Med. Chem. 9(3):348-355 (2009).
Tolaney et al., "HER2-Positive Breast Cancer," JCOM 14(7):395-403 (2007).
Tomillero and Moral, "Gateways to Clinical Trials," Methods Find. Exp. Clin. Pharmacol. 31(3): 183-226 (2009).
Tomillero and Moral, "Gateways to Clinical Trials," Methods Find. Exp. Clin. Pharmacol. 31(10):661-700 (2009).
Tookman and Roylance, "New Drugs for Breast Cancer," Br. Med. Bull. 96:111-129 (2010) (Epub Sep. 23, 2010).
Torres and Harris, "Polycystic kidney disease: genes, proteins, animal models, disease mechanisms and therapeutic opportunities," J. Intern. Med. 261(1):17-31 (2007).
Traxler, "Tyrosine kinase inhibitors in cancer treatment (Part II)," Exp. Opin. Ther. Patents 8(12):1599-1625 (1998).
Tsou et al., "Optimization of 6,7-Disubstituted-4-(Arylamino)Quinoline-3-Carbonitriles as Orally Active, Irreversible Inhibitors of Human Epidermal Growth Factor Receptor-2 Kinase Activity," J. Med. Chem. 48(4):1107-1131 (2005).
Tsou, "American Chemical Society—226th National Meeting. Novel Substituted 4-Anilinoquinoline-3-carbonitriles as orally active, irreversible binding inhibitors of HER-2 Kinase," (abstr. 14) 2003.
Twelves et al., "Erlotinib in combination with capecitabine and docetaxel in patients with metastatic breast cancer: a dose-escalation study," Eur. J. Cancer 44(3):419-426 (2008) (Epub Jan. 30, 2008).
Ullrich et al., "Human epidermal growth factor receptor cDNA sequence and aberrant expression of the amplified gene in A431 epidermoid carcinoma cells," Nature 309(5967):418-425 (1984).
Untch, "Targeted Therapy for Early and Locally Advanced Breast Cancer," Breast Care (Basel) 5(3):144-152 (2010) (Epub Jun. 16, 2010).
Upeslacis, Janis, Meeting At Mcgill University, Canada, Evolution of Kinase Inhibitors At Wyeth, Oct. 16, 2002.
Van Arnum, "Evaluating late-stage pipelines and potential: will 2011 be a more promising year for new molecular entities? A review of Big Pharma's late-stage pipeline shows what might lie ahead." Pharmaceutical Technology 35.2 (2011): 52+. Expanded Academic ASAP. Web. Jul. 18, 2011.
Van Schaeybroeck et al., "Epidermal growth factor receptor activity determines response of colorectal cancer cells to gefitinib alone and in combination with chemotherapy," Clin. Cancer Res. 11(20):7480-7489 (2005).
Vasudevan et al., "AKT-independent signaling downstream of oncogenic PIK3CA mutations in human cancer," Cancer Cell 16(1):21-32 (2009).
Vazquez et al., "HER2-Positive Breast Cancer: Analysis of Efficacy in Different Groups," Cancer Chemother. Rev. 4(4):224-240 (2009).
Vengerovsky, "Farmacologicheskaya nesovmestimost," Bulleten' sibirskoi medicini 3:49-56 (2003). (English translation of Abstract provided).
Vincent et al., "Anticancer efficacy of the irreversible EGFr tyrosine kinase inhibitor PD 0169414 against human tumor xenografts," Cancer Chemother. Pharmacol. 45(3):231-238 (2000).
Vivanco and Mellinghoff, "Epidermal growth factor receptor inhibitors in oncology," Curr. Opin. Oncol. 22(6):573-578 (2010).
Von Eyben, "Epidermal growth factor receptor inhibition and non-small cell lung cancer," Crit. Rev. Clin. Lab. Sci. 43(4):291-323 (2006).
Vora et al., "Novel Therapeutics in Breast Cancer—Looking to the Future," Update on Cancer Therapeutics 3:189-205 (2009).
Wagner and Kaufmann, "Prospects for the Use of ATR Inhibitors to Treat Cancer," Pharmaceuticals 3:1311-1334 (2010).
Walko and Lindley, "Capecitabine: a review," Clin. Ther. 27(1):23-44 (2005).
Wang et al., "Characterization of HKI-272 covalent binding to human serum albumin," Drug Metab. Dispos. 38(7):1083-1093 (2010) (Epub Apr. 16, 2010).
Ware et al., "A mechanism of resistance to gefitinib mediated by cellular reprogramming and the acquisition of an FGF2-FGFR1 autocrine growth loop," Oncogenesis 2:e39 (2013).
Weber, "Toward a molecular classification of cancer," Toxicology Dec. 5, 2010;278(2):195-198 (2010) (Epub Oct. 24, 2009).
Wen and Drappatz, "Novel therapies for meningiomas," Expert Rev. Neurother. 6(10):1447-1464 (2006).
Wheatley-Price and Shepherd, "Epidermal growth factor receptor inhibitors in the treatment of lung cancer: reality and hopes," Curr. Opin. Oncol. 20(2):162-175 (2008).
Whenham et al., "HER2-positive breast cancer: from trastuzumab to innovatory anti-HER2 strategies," Clin. Breast Cancer 8(1):38-49 (2008).
Wickham, "Evolving treatment paradigms for chemotherapy-induced nausea and vomiting," Cancer Control 19(2 Suppl):3-9 (2012).
Widakowich et al., "HER-2 positive breast cancer: what else beyond trastuzumab-based therapy?" Anticancer Agents Med. Chem. 8(5):488-496 (2008).
Widakowich et al., "Molecular targeted therapies in breast cancer: where are we now?" Int. J. Biochem. Cell. Biol. 2007;39(7-8):1375-1387 (2007) (Epub May 4, 2007).
Wissner and Mansour, "The development of HKI-272 and related compounds for the treatment of cancer," Arch. Pharm. (Weinheim) 341(8):465-477 (2008).
Wissner et al., "Dual irreversible kinase inhibitors. quinazoline-based inhibitors incorporating two independent reactive centers with each targeting different cysteine residues in the kinase domains of EGFR and VEGFR-2," Bioorg. Med. Chem. 15(11):3635-4368 (2007) (Epub Mar. 23, 2007).
Woenckhaus et al., "Prognostic value of PIK3CA and phosphorylated AKT expression in ovarian cancer," Virchows Arch. 450(4):387-395 (2007) (Epub Feb. 15, 2007).
Wondrak, "Redox-directed cancer therapeutics: molecular mechanisms and opportunities," Antioxid. Redox Signal. 11(12):3013-3069 (2009).
Wong et al., "A phase I study with neratinib (HKI-272), an irreversible pan ErbB receptor tyrosine kinase inhibitor, in patients with solid tumors," Clin. Cancer Res. 15(7):2552-2558 (2009) (Epub Mar. 24, 2009).
Wong et al., "HKI-272, an irreversible pan ErbB receptor tyrosine kinase inhibitory: Preliminary phase 1 results in patients with solid tumors," J. Clin. Oncol. 24(18S):125s Abstr. 3018 (2006).
Wong, "HKI-272 in non small cell lung cancer," Clin. Cancer Res. 13(15 Pt 2):4593s-4596s (2007).
Wong, "Searching for a magic bullet in NSCLC: the role of epidermal growth factor receptor mutations and tyrosine kinase inhibitors," Lung Cancer 60(Suppl 2):S10-S18 (2008).
World Health Organization (2008). *Fact Sheet—Cancer*, No. 297, 2008. Retrieved from http://www.who.int/mediacentre/factsheets/fs297/en/.

(56) References Cited

OTHER PUBLICATIONS

World Health Organization (2008). *World Health Statistics*, 2008. Retrieved from http://www.who.int/gho/publications/world_health_statistics/EN_WHS08_Full.pdf?ua=1.
Written Opinion of the International Searching Authority for International Application No. PCT/US2009/047643 dated Dec. 17, 2010.
Wu et al., "Design and synthesis of tetrahydropyridothieno[2,3-d]pyrimidine scaffold based epidermal growth factor receptor (EGFR) kinase inhibitors: the role of side chain chirality and Michael acceptor group for maximal potency," J. Med. Chem. 53(20):7316-7326 (2010).
Wu et al., "Somatic mutation and gain of copy number of PIK3CA in human breast cancer," Breast Cancer Res. 7(5):R609-R616 (2005) (Epub May 31, 2005).
Wu et al., "TAK-285, a Novel HER2/EGFR Inhibitor, Penetrates the CNS in Rats with an Intact Blood Brain Barrier (BBB),"Cancer Res. 69(24 Suppl): Abstr. 5098 (2009).
Wu et al., "Uncommon mutation, but common amplifications, of the PIK3CA gene in thyroid tumors," J. Clin. Endocrinol. Metab. 90(8):4688-4693 (2005) (Epub May 31, 2005).
Wykosky et al., "Therapeutic targeting of epidermal growth factor receptor in human cancer: successes and limitations," Chin. J. Cancer 30(1):5-12 (2011).
Xia et al., "Truncated ErbB2 receptor (p95ErbB2) is regulated by heregulin through heterodimer formation with ErbB3 yet remains sensitive to the dual EGFR/ErbB2 kinase inhibitor GW572016," Oncogene 23(3):646-653 (2004).
Xu et al., "Acquired resistance of lung adenocarcinoma to EGFR-tyrosine kinase inhibitors gefitinib and erlotinib," Cancer Biol. Ther. 9(8):572-582 (2010) (Epub Apr. 26, 2010).
Yamano, "Approach to Crystal Polymorph in Process Research of New Drug," Journal of Synthetic Organic Chemistry, Japan, 65(9):907-913 (2007). [English Translation Not Available].
Yang et al., "MicroRNA expression profiling in human ovarian cancer: miR-214 induces cell survival and cisplatin resistance by targeting PTEN," Cancer Res. 68(2):425-433 (2008).
Yano et al., "HGF-MET in Resistance to EGFR Tyrosine Kinase Inhibitors in Lung Cancer," Curr. Signal Transduct. Ther. 6(2):228-233 (2011).
Yim et al., "Rak functions as a tumor suppressor by regulating PTEN protein stability and function," Cancer Cell 15(4):304-314 (2009).
Yoshida et al., "Targeting epidermal growth factor receptor: central signaling kinase in lung cancer," Biochem. Pharmacol. 80(5):613-623 (2010) (Epub May 24, 2010).
Yoshimura et al., "EKB-569, a new irreversible epidermal growth factor receptor tyrosine kinase inhibitor, with clinical activity in patients with non-small cell lung cancer with acquired resistance to gefitinib," Lung Cancer 51(3):363-368 (2006) (Epub Dec. 20, 2005).
Yuan and Cantley, "PI3K pathway alterations in cancer: variations on a theme," Oncogene 27(41):5497-5510 (2008).
Yun et al., "The T790M mutation in EGFR kinase causes drug resistance by increasing the affinity for ATP," Proc. Natl. Acad. Sci. U.S.A. 105(6):2070-2075 (2008) (Epub Jan. 28, 2008).
Yuza et al., "Allele-dependent variation in the relative cellular potency of distinct EGFR inhibitors," Cancer Biol. Ther. 6(5):661-667 (2007) (Epub Feb. 13, 2007).
Zaczek et al., "The diverse signaling network of EGFR, HER2, HER3 and HER4 tyrosine kinase receptors and the consequences for therapeutic approaches," Histol. Histopathol. 20(3):1005-1015 (2005).
Zagrekova et al., "Drug Treatment of Breast Cancer," Rossijskij Medicinskij Zhurnal 14:605 (2002). (English Translation Not Available).
Zahnow, "ErbB receptors and their ligands in the breast," Expert Rev. Mol. Med. 8(23):1-21 (2006).
Zhang et al., Xenograft Models of Breast Cancer: the Link between Characteristics of Biomarker Expression and the Anti-tumor Effect of the Representative Therapies [abstract]. In: Proceedings of the 101st Annual Meeting of the American Association for Cancer Research; Apr. 17-21, 2010; Washington, DC. Philadelphia (PA): AACR; Cancer Res 2010;70(8 Suppl):Abstract nr 647.
Zhang et al., "Advances in preclinical small molecules for the treatment of NSCLC," Expert Opin. Ther. Pat. 19(6):731-751 (2009).
Zhang et al., "Targeting cancer with small molecule kinase inhibitors," Nature 9:28-39 (2009).
Zhao et al., "Nemtinib Reverses ATP-Binding Cassette B1-Mediaed Chemotherapeutic Drug Resistance in Vitro, in Vivo, and Ex-Vivo," Mol. Pharmacal. 82: 47-58 (2012).
Zhou et al., "Activation of the PTEN/Mtor/STAT3 Pathway in Breast Cancer Stem-Like Cells is Required for Viability and Maintenance," Proc. Natl. Acad. Sci. U.S.A. 104:16158-16163 (2007).
Zhou et al., "EGFR Intron I Polymorphism in Asian Populations and Its Correlation with EGFR Gene Expression and Amplification in Breast Tumor Tissues," Cancer Biol. Ther. 5(11):1445-1449 (2006).
Zhou et al., "Novel Mutant-Selective EGFR Kinase Inhibitors Against EGFR T790M," Nature 462(7276):1070-1074 (2009).
Official Action dated Apr. 9, 2010 in parent U.S. Appl. No. 11/883,474.
Official Action dated Sep. 14, 2010 in parent U.S. Appl. No. 11/883,474.
Official Action dated Sep. 27, 2013 in parent U.S. Appl. No. 11/883,474.
Official Action dated May 2, 2014 in parent U.S. Appl. No. 11/883,474.
Official Action dated Sep. 29, 2014 in parent U.S. Appl. No. 11/883,474.
Official Action dated May 21, 2015 in parent U.S. Appl. No. 11/883,474.
Official Action dated Dec. 9, 2015 in parent U.S. Appl. No. 11/883,474.
Official Action dated May 9, 2016 in parent U.S. Appl. No. 11/883,474.
Anzensei shiken gaidorain (Guidelines for safety testing), Pharmaceutical Affairs Bureau Notification No. 0603001, Jun. 3, 2003; Notification Date: Oct. 19, 2017. (English translation attached).
AstraZeneca Press Release, "TAGRISSO™ (osimertinib) (AZD9291) approved by the US FDA as treatment for patients with EGFR T790M mutation-positive metastatic non-small cell lung cancer," published Nov. 13, 2015. [Obtained from the Internet on Mar. 7, 2017].
Blackwell et al., "Randomized study of Lapatinib alone or in combination with trastuzumab in women with EthB2-positive, trastuzumab-refractory metastatic breast cancer," J. Clin. Oncol. 28(7):1124-1130 (2010).
Carmi et al., "Clinical perspectives for irreversible tyrosine kinase inhibitors in cancer," Biochem. Pharmacol. 84(11):1388-1399 (2012) (Epub Aug. 4, 2012).
Chan et al., "Neratinib after trastuzumab-based adjuvant therapy in patients with HER2-positive breast cancer (ExteNET): a multicentre, randomised, double-blind, placebo-controlled, phase 3 trial," 17(3):367-377 (2016) (Epub Feb. 10, 2016).
Chan, "Targeting the mammalian target of rapamycin (mTOR): a new approach to treating cancer," Br. J. Cancer. 91(8):1420-1424 (2004).
Chew et al., "Phase II study of lapatinib in combination with vinorelbine, as first or second-line therapy in women with HER2 overexpressing metastatic breast cancer," SpringerPlus 3:108 (2014).
Ciardiello et al., "The role of EGFR inhibitors in nonsmall cell lung cancer," Curr. Opin. Oncol. 16(2):130-135 (2004).
Cross et al., "AZD9291, an irreversible EGFR TKI, overcomes T790M-mediated resistance to EGFR inhibitors in lung cancer," Cancer Discov. 4(9):1046-1061 (2014) (Epub Jun. 3, 2014).
Cybulska-Stopa et al., "Evaluation of vinorelbine-based chemotherapy as the second or further-line treatment in patients with metastatic breast cancer," Wspalczesna Onkol. 17(1):78-82 (2013).
Davies et al., "OSI-774 and vinorelbine in advanced solid tumors (with emphasis on non-small cell lung cancer, NSCLC): A phase I study," Proc. Am. Soc. Clin. Oncol. 22: 2003 (abstr 996). 2003 ASCO Annual Meeting.
Degardin et al., "Vinorelbine (navelbine) as a salvage treatment for advanced breast cancer," Ann. Oncol. 5(5):423-426 (1994).

(56) References Cited

OTHER PUBLICATIONS

Depierre et al., "Vinorelbine versus vinorelbine plus cisplatin in advanced non-small cell lung cancer: a randomized trial," Ann. Oncol. 5(1):37-42 (1994).
Emea: Committee for Medicinal Products for Human Use (CHMP). Guideline on the Evaluation of Anticancer Medicinal Products in Man. London, Dec. 14, 2005.
Gandhi et al., "Phase I Study of Neratinib in Combination With Temsirolimus in Patients With Human Epidermal Growth Factor Receptor 2-Dependent and Other Solid Tumors," J. Clin. Oncol. 32(2):68-75 (2014) (Epub Dec. 9, 2013).
Hegde et al., "Delineation of molecular mechanisms of sensitivity to lapatinib in breast cancer cell lines using global gene expression profiles," Mol. Cancer Ther. 6(5):1629-1640 (2007).
Herbst, "Review of epidermal growth factor receptor biology," Int. J. Radiat. Oncol. Biol. Phys.59(2 Suppl):21-26 (2004).
Ich Expert Working Group: "Impurities in New Drug Substances Q3A (R), International Conference on Harmonisation of Technical Requirements for Registration of Pharmaceuticals for Human Use" (Online) 2006, URL: http://www.ich.org/fileadmin/Public_Web_Site/ICH_Products/Guidelines/Quality/Q3B_R2/Step4/Q3B_R2_Guideline.pdf.
Laheru et al., "A phase I study of EKB-569, an irreversible inhibitor of epidermal growth factor receptor, in combination with capecitabine in patients with advanced colorectal cancer: Preliminary report," Clin. Cancer Res. 9: 6091s-6092s; Abstr. 93 (2003).
Miller et al., "Afatinib versus placebo for patients with advanced, metastatic non-small-cell lung cancer after failure of erlotinib, gefitinib, or both, and one or two lines of chemotherapy (LUX-Lung 1): a phase 2b/3 randomised trial ," Lancet Oncol. 13:528-538 (2012).
Modjtahedi et al., "A comprehensive review of the preclinical efficacy profile of the ErbB family blocker afatinib in cancer," Naunyn Schmiedebergs Arch. Pharmacol. Jun, 2014;387(6):505-521 (2014) (Epub Mar. 19, 2014).
Mondesire et al., "Targeting mammalian target of rapamycin synergistically enhances chemotherapy-induced cytotoxicity in breast cancer cells," Clin. Cancer Res. 10(20):7031-7042 (2004).
Normanno et al., "Epidermal Growth Factor Receptor Tyrosine Kinase Inhibitors (EGFR-TKIs): Simple Drugs With a Complex Mechanism of Action?" J. Cell. Physiol. 194:13-19 (2002).
Pegram et al., "Rational Combinations of Trastuzumab with Chemotherapeutic Drugs Used in the Treatment of Breast Cancer," J. Natl. Cancer Inst. 96(10):739-749 (2004).
"Progress of Research on Therapeutic Drugs and Molecular Pharmacology", edited by Zhou Hong et al., Sichuan University Press, published in Mar. 2004, pp. 46-47. (English translation attached).
Qiu et al., "Mechanism of Activation and Inhibition of the HER4/ErbB4 Kinase," Structure 16(3):460-467 (2008).
Schedule of Presentations—Chemotherapy Foundation Symposium XXV—Nov. 6, 2007.
Scholl et al., "Targeting HER2 in other tumor types," Ann. Oncol. 12(Suppl. 1):S81-S87 (2001).
Tan et al., "The International Association for the Study of Lung Cancer Consensus Statement on Optimizing Management of EGFR Mutation-Positive Non-Small Cell Lung Cancer: Status in 2016," J. Thorac. Oncol. 11(7):946-963 (2016).
U.S. National Institutes of Health, "View of NCT00389922 on May 26, 2008".
U.S. National Institutes of Health, "View of NCT00513058 on May 26, 2008".
U.S. National Institutes of Health, "View of NCT00706030 on Jun. 26, 2008".
Wikipedia, "Neoplasm" [retrieved from internet on Sep. 12, 2016] URL:http://en.wikipedia.org/wiki/Neoplasm published Aug. 17, 2016.
Wyeth: "Study Evaluating HKI-272 in Combination With Vinorelbine in Subjects With Solid Tumors and Metastatic Breast Cancer," ClinicalTrials, Jun. 25, 2008. Retrieved from the Internet: URL: http://clinicaltrials.gov/ct2/show/NCT00706030?term=vinorelbine+hki-272&rank=1 [retrieved on Jan. 13, 2010].
Wyeth: "Study evaluating Neratinib in Combination With Vinorelbine in Subjects With Advanced or Metastatic Solid Tumors," ClinicalTrials, Aug. 5, 2009. Retrieved from the Internet: URL: http://clinicaltrials.gov/ct2/show/NCT/00958724?term=vinorelbine+hki-272&rank=2 [retrieved on Jan. 13, 2010].
Yap et al., "Targeting the PI3K-AKT-mTOR pathway: progress, pitfalls, and promises," Curr. Opin. Pharmacol. 8:393-412 (2008).
Extended European Search Report dated Nov. 17, 2016 for European Application No. EP 16193659.6.
United States Patent and Trademark Office Final Office Action for U.S. Appl. No. 12/534,895, dated May 2, 2013 (20 pages).
United States Patent and Trademark Office Final Office Action for U.S. Appl. No. 12/940,797, dated Mar. 29, 2012 (11 pages).
United States Patent and Trademark Office Non-Final Office Action for U.S. Appl. No. 12/534,895, dated Nov. 1, 2011 (23 pages).
United States Patent and Trademark Office Non-Final Office Action for U.S. Appl. No. 12/940,797, dated Sep. 30, 2011 (15 pages).
United States Patent and Trademark Office Non-Final Office Action for U.S. Appl. No. 12/940,797, dated Sep. 13, 2012 (20 pages).
United States Patent and Trademark Office Notice of Allowance for U.S. Appl. No. 12/534,895, dated Sep. 12, 2013 (6 pages).
United States Patent and Trademark Office Notice of Allowance for U.S. Appl. No. 12/940,797, dated May 3, 2013 (12 pages).
Written Opinion of the International Searching Authority for International Application No. PCT/US2010/054934 dated May 10, 2011.
Written Opinion of the International Searching Authority for International Application No. PCT/US2011/020080 dated Feb. 28, 2011.
Campos et al., "A phase 2, single agent study of CI-1033 administered at two doses in ovarian cancer patients who failed platinum therapy," J. Clin. Oncol. (ASCO Annual Meeting Proceedings) 22(14S):5054 (2004).
Casado et al., "A phase I/IIA pharmacokinetic (PK) and serial skin and tumor pharmacodynamic (PD) study of the EGFR irreversible tyrosine kinase inhibitor EKB-569 in combination with 5-fluorouracil (5FU), leucovorin (LV) and irinotecan (CPT-11) (FOLFIRI regimen) in patients (pts) with advanced colorectal cancer (ACC)," J. Clin. Oncol., 2004 ASCO Annual Meeting Proceedings (Post-Meeting Edition). vol. 22, No. 14S (Jul. 15 Supplement), 2004:3543.
Clovis Oncology, Inc. publication on Rociletinib: "Study to Evaluate Safety, Pharmacokinetics, and Efficacy of Rociletinib (CO-1686) in Previously Treated Mutant Epidermal Growth Factor Receptor (EGFR) in Non-Small Cell Lung Cancer (NSCLC) Patients." ClinicalTrials.gov Identifier: NCT01526928; verified Feb. 2015 by Clovis Oncology, Inc.
Comments by the President of the European Patent Office re: Case G 1/12—Invitation to comment under Article 9 of the Rules of Procedure of the Enlarged Board of Appeal dated Jun. 25, 2012 (9 pages).
Costa et al., "The impact of EGFR T790M mutations and BIM mRNA expression on outcome in patients with EGFR-mutant NSCLC treated with erlotinib or chemotherapy in the randomized phase III EURTAC trial," Clin. Cancer Res. 20:2001-2010 (2014).
Declaration by Dr. Leena Gandhi, MD, PhD., dated Feb. 13, 2015 (6 pages).
Declaration by Thomas C. Harding, Ph.D., executed on Oct. 1, 2014 (15 pages).
Desai et al., "EGFR pharmacogenomics: the story continues to mutate and evolve," Am. J. Pharmacogenomics 5(2):137-139 (2005).
Dowell et al., "Chasing mutations in the epidermal growth factor in lung cancer," N. Engl. J. Med. 352(8):830-832 (2005).
Dua et al., "EGFR over-expression and activation in high HER2, ER negative breast cancer cell line induces trastuzumab resistance," Breast Cancer Res. Treat. 122(3):685-697 (2010) (Epub Oct. 27, 2009).
Hidalgo et al., "Phase 1 trial of EKB-569, an irreversible inhibitor of the epidermal growth factor receptor (EGFR), in patients with advanced solid tumors," ASCO Annual Meeting Proceedings, 21:17a; Abstr. 65 (2002).
Irwin et al., "Small Molecule ErbB Inhibitors Decrease Proliferative Signaling and Promote Apoptosis in Philadelphia Chromosome-Positive Acute Lymphoblastic Leukemia" PLoS One 8(8): e70608 (2013).

(56) References Cited

OTHER PUBLICATIONS

Kobayashi et al. "Gefitinib resistance caused by a secondary mutation of the epidermal growth factor receptor," Proc. Amer. Assoc. Cancer Res. 46:620; Abstr. 2637 (2005).

Morgan et al., "Preliminary report of a phase 1 study of EKB-569, an irreversible inhibitor of the epidermal growth factor receptor (EGFR), given in combination with gemcitabine to patients with advanced pancreatic cancer," ASCO Annual Meeting Proceedings, 22(Abstr. 788):197 (2003).

Nagasawa et al., "Novel HER2 selective tyrosine kinase inhibitor, TAK-165, inhibits bladder, kidney and androgen-independent prostate cancer in vitro and in vivo," Int. J. Urol. 13(5):587-592 (May 2006).

Nemunaitis et al., "Phase 1 clinical and pharmacokinetics evaluation of oral CI-1033 in patients with refractory cancer," Clin. Cancer Res. 11(10):3846-3853 (2005).

Pao et al., "KRAS Mutations and Primary Resistance of Lung Adenocarcinomas to Gefitinib or Erlotinib," PLoS Med. 2(1):e17 (2005) (Epub Jan. 25, 2005).

Salazar et al., "Preliminary report of a phase I/IIA open-label study of EKB-569 in combination with 5-fluorouracil, leucovorin. irinotecan in patients with advanced colorectal cancer," Clin. Cancer Res. 9(16):60995-61005; Abstr. 125 (2003).

Schuler et al., "An interim analysis of the LUX-Lung 5 trial: Afatinib monotherapy in metastatic NSCLC following progressionon chemotherapy and erlotinib/gefitinib," J. Clin. Oncol. (ASCO Annual Meeting Abstracts) 2012;(Suppl):7557.

Schuler et al., "Continuation of afatinib beyond progression: Results of a randomized, open-label, phase III trial of afatinib plus paclitaxel (P) versus investigator's choice chemotherapy (CT) in patients (pts) with metastatic non-small cell lung cancer (NSCLC) progressed on erlotinib/gefitinib (E/G) and afatinib-Lux-Lung 5 (LL5)," J. Clin. Oncol. 32:5s, 2014 (suppl; abstr. 8019).

Sequist et al., "Neratinib, an Irreversible Pan-ErbB Receptor Tyrosine Kinase Inhibitor: Results of a Phase II Trial in Patients With Advanced Non-Small-Cell Lung Cancer," J. Clin. Oncol. 28(18):3076-3083 (2010) (Epub May 17, 2010).

Su et al., "Pretreatment epidermal growth factor receptor (EGFR) T790M mutation predicts shorter EGFR tyrosine kinase inhibitor response duration in patients with non-small-cell lung cancer," J. Clin. Oncol. 30(4):433-440 (2012) (Epub Jan. 3, 2012).

\* cited by examiner

```
CCCGGCGCAGCGCGGCCGCAGCAGCCTCCGCCCCCCGCACGGTGTGAGCGCCCGACGCGG  -185
............................................................

CCGAGGCGGCCGGAGTCCCGAGCTAGCCCCGGCGGCCGCCGCCGCCCAGACCGGACGACA  -125
............................................................

GGCCACCTCGTCGGCGTCCGCCCGAGTCCCCGCCTCGCCGCCAACGCCACAACCACCGCG  -65
............................................................

CACGGCCCCCTGACTCCGTCCAGTATTGATCGGGAGAGCCGGAGCGAGCTCTTCGGGGAG  -5
............................................................

CAGCGATGCGACCCTCCGGGACGGCCGGGGCAGCGCTCCTGGCGCTGCTGGCTGCGCTCT  55
.....-M--R--P--S--G--T--A--G--A--A--L--L--A--L--L--A--A--L--  18

GCCCGGCGAGTCGGGCTCTGGAGGAAAAGAAAGTTTGCCAAGGCACGAGTAACAAGCTCA  115
C--P--A--S--R--A--L--E--E--K--K--V--C--Q--G--T--S--N--K--L--  38

CGCAGTTGGGCACTTTTGAAGATCATTTTCTCAGCCTCCAGAGGATGTTCAATAACTGTG  175
T--Q--L--G--T--F--E--D--H--F--L--S--L--Q--R--M--F--N--N--C--  58

AGGTGGTCCTTGGGAATTTGGAAATTACCTATGTGCAGAGGAATTATGATCTTTCCTTCT  235
E--V--V--L--G--N--L--E--I--T--Y--V--Q--R--N--Y--D--L--S--F--  78

TAAAGACCATCCAGGAGGTGGCTGGTTATGTCCTCATTGCCCTCAACACAGTGGAGCGAA  295
L--K--T--I--Q--E--V--A--G--Y--V--L--I--A--L--N--T--V--E--R--  98

TTCCTTTGGAAAACCTGCAGATCATCAGAGGAAATATGTACTACGAAAATTCCTATGCCT  355
I--P--L--E--N--L--Q--I--I--R--G--N--M--Y--Y--E--N--S--Y--A--  118

TAGCAGTCTTATCTAACTATGATGCAAATAAAACCGGACTGAAGGAGCTGCCCATGAGAA  415
L--A--V--L--S--N--Y--D--A--N--K--T--G--L--K--E--L--P--M--R--  138

ATTTACAGGAAATCCTGCATGGCGCCGTGCGGTTCAGCAACAACCCTGCCCTGTGCAACG  475
N--L--Q--E--I--L--H--G--A--V--R--F--S--N--N--P--A--L--C--N--  158

TGGAGAGCATCCAGTGGCGGGACATAGTCAGCAGTGACTTTCTCAGCAACATGTCGATGG  535
V--E--S--I--Q--W--R--D--I--V--S--S--D--F--L--S--N--M--S--M--  178

ACTTCCAGAACCACCTGGGCAGCTGCCAAAAGTGTGATCCAAGCTGTCCCAATGGGAGCT  595
D--F--Q--N--H--L--G--S--C--Q--K--C--D--P--S--C--P--N--G--S--  198

GCTGGGGTGCAGGAGAGGAGAACTGCCAGAAACTGACCAAAATCATCTGTGCCCAGCAGT  655
C--W--G--A--G--E--E--N--C--Q--K--L--T--K--I--I--C--A--Q--Q--  218

GCTCCGGGCGCTGCCGTGGCAAGTCCCCCAGTGACTGCTGCCACAACCAGTGTGCTGCAG  715
C--S--G--R--C--R--G--K--S--P--S--D--C--C--H--N--Q--C--A--A--  238

GCTGCACAGGCCCCCGGGAGAGCGACTGCCTGGTCTGCCGCAAATTCCGAGACGAAGCCA  775
G--C--T--G--P--R--E--S--D--C--L--V--C--R--K--F--R--D--E--A--  258

CGTGCAAGGACACCTGCCCCCCACTCATGCTCTACAACCCCACCACGTACCAGATGGATG  835
T--C--K--D--T--C--P--P--L--M--L--Y--N--P--T--T--Y--Q--M--D--  278

TGAACCCCGAGGGCAAATACAGCTTTGGTGCCACCTGCGTGAAGAAGTGTCCCCGTAATT  895
V--N--P--E--G--K--Y--S--F--G--A--T--C--V--K--K--C--P--R--N--  298
```

*FIG. 5*

```
ATGTGGTGACAGATCACGGCTCGTGCGTCCGAGCCTGTGGGGCCGACAGCTATGAGATGG  955
 Y--V--V--T--D--H--G--S--C--V--R--A--C--G--A--D--S--Y--E--M--  318

AGGAAGACGGCGTCCGCAAGTGTAAGAAGTGCGAAGGGCCTTGCCGCAAAGTGTGTAACG 1015
 E--E--D--G--V--R--K--C--K--K--C--E--G--P--C--R--K--V--C--N--  338

GAATAGGTATTGGTGAATTTAAAGACTCACTCTCCATAAATGCTACGAATATTAAACACT 1075
 G--I--G--I--G--E--F--K--D--S--L--S--I--N--A--T--N--I--K--H--  358

TCAAAAACTGCACCTCCATCAGTGGCGATCTCCACATCCTGCCGGTGGCATTTAGGGGTG 1135
 F--K--N--C--T--S--I--S--G--D--L--H--I--L--P--V--A--F--R--G--  378

ACTCCTTCACACATACTCCTCCTCTGGATCCACAGGAACTGGATATTCTGAAAACCGTAA 1195
 D--S--F--T--H--T--P--P--L--D--P--Q--E--L--D--I--L--K--T--V--  398

AGGAAATCACAGGGTTTTTGCTGATTCAGGCTTGGCCTGAAAACAGGACGGACCTCCATG 1255
 K--E--I--T--G--F--L--L--I--Q--A--W--P--E--N--R--T--D--L--H--  418

CCTTTGAGAACCTAGAAATCATACGCGGCAGGACCAAGCAACATGGTCAGTTTTCTCTTG 1315
 A--F--E--N--L--E--I--I--R--G--R--T--K--Q--H--G--Q--F--S--L--  438

CAGTCGTCAGCCTGAACATAACATCCTTGGGATTACGCTCCCTCAAGGAGATAAGTGATG 1375
 A--V--V--S--L--N--I--T--S--L--G--L--R--S--L--K--E--I--S--D--  458

GAGATGTGATAATTTCAGGAAACAAAAATTTGTGCTATGCAAATACAATAAACTGGAAAA 1435
 G--D--V--I--I--S--G--N--K--N--L--C--Y--A--N--T--I--N--W--K--  478

AACTGTTTGGGACCTCCGGTCAGAAAACCAAAATTATAAGCAACAGAGGTGAAAACAGCT 1495
 K--L--F--G--T--S--G--Q--K--T--K--I--I--S--N--R--G--E--N--S--  498

GCAAGGCCACAGGCCAGGTCTGCCATGCCTTGTGCTCCCCCGAGGGCTGCTGGGGCCCGG 1555
 C--K--A--T--G--Q--V--C--H--A--L--C--S--P--E--G--C--W--G--P--  518

AGCCCAGGGACTGCGTCTCTTGCCGGAATGTCAGCCGAGGCAGGGAATGCGTGGACAAGT 1615
 E--P--R--D--C--V--S--C--R--N--V--S--R--G--R--E--C--V--D--K--  538

GCAACCTTCTGGAGGGTGAGCCAAGGGAGTTTGTGGAGAACTCTGAGTGCATACAGTGCC 1675
 C--N--L--L--E--G--E--P--R--E--F--V--E--N--S--E--C--I--Q--C--  558

ACCCAGAGTGCCTGCCTCAGGCCATGAACATCACCTGCACAGGACGGGGACCAGACAACT 1735
 H--P--E--C--L--P--Q--A--M--N--I--T--C--T--G--R--G--P--D--N--  578

GTATCCAGTGTGCCCACTACATTGACGGCCCCCACTGCGTCAAGACCTGCCCGGCAGGAG 1795
 C--I--Q--C--A--H--Y--I--D--G--P--H--C--V--K--T--C--P--A--G--  598

TCATGGGAGAAAACAACACCCTGGTCTGGAAGTACGCAGACGCCGGCCATGTGTGCCACC 1855
 V--M--G--E--N--N--T--L--V--W--K--Y--A--D--A--G--H--V--C--H--  618

TGTGCCATCCAAACTGCACCTACGGATGCACTGGGCCAGGTCTTGAAGGCTGTCCAACGA 1915
 L--C--H--P--N--C--T--Y--G--C--T--G--P--G--L--E--G--C--P--T--  638

ATGGGCCTAAGATCCCGTCCATCGCCACTGGGATGGTGGGGGCCCTCCTCTTGCTGCTGG 1975
 N--G--P--K--I--P--S--I--A--T--G--M--V--G--A--L--L--L--L--L--  658

TGGTGGCCCTGGGGATCGGCCTCTTCATGCGAAGGCGCCACATCGTTCGGAAGCGCACGC 2035
 V--V--A--L--G--I--G--L--F--M--R--R--R--H--I--V--R--K--R--T--  678
```

FIG. 5 (con'd.)

```
TGCGGAGGCTGCTGCAGGAGAGGGAGCTTGTGGAGCCTCTTACACCCAGTGGAGAAGCTC  2095
L--R--R--L--L--Q--E--R--E--L--V--E--P--L--T--P--S--G--E--A--   698

CCAACCAAGCTCTCTTGAGGATCTTGAAGGAAACTGAATTCAAAAAGATCAAAGTGCTGG  2155
P--N--Q--A--L--L--R--I--L--K--E--T--E--F--K--K--I--K--V--L--   718

GCTCCGGTGCGTTCGGCACGGTGTATAAGGGACTCTGGATCCCAGAAGGTGAGAAAGTTA  2215
G--S--G--A--F--G--T--V--Y--K--G--L--W--I--P--E--G--E--K--V--   738

AAATTCCCGTCGCTATCAAGGAATTAAGAGAAGCAACATCTCCGAAAGCCAACAAGGAAA  2275
K--I--P--V--A--I--K--E--L--R--E--A--T--S--P--K--A--N--K--E--   758

TCCTCGATGAAGCCTACGTGATGGCCAGCGTGGACAACCCCCACGTGTGCCGCCTGCTGG  2335
I--L--D--E--A--Y--V--M--A--S--V--D--N--P--H--V--C--R--L--L--   778

GCATCTGCCTCACCTCCACCGTGCAGCTCATCACGCAGCTCATGCCCTTCGGCTGCCTCC  2395
G--I--C--L--T--S--T--V--Q--L--I--T--Q--L--M--P--F--G--C--L--   798

TGGACTATGTCCGGGAACACAAAGACAATATTGGCTCCCAGTACCTGCTCAACTGGTGTG  2455
L--D--Y--V--R--E--H--K--D--N--I--G--S--Q--Y--L--L--N--W--C--   818

TGCAGATCGCAAAGGGCATGAACTACTTGGAGGACCGTCGCTTGGTGCACCGCGACCTGG  2515
V--Q--I--A--K--G--M--N--Y--L--E--D--R--R--L--V--H--R--D--L--   838

CAGCCAGGAACGTACTGGTGAAAACACCGCAGCATGTCAAGATCACAGATTTTGGGCTGG  2575
A--A--R--N--V--L--V--K--T--P--Q--H--V--K--I--T--D--F--G--L--   858

CCAAACTGCTGGGTGCGGAAGAGAAAGAATACCATGCAGAAGGAGGCAAAGTGCCTATCA  2635
A--K--L--L--G--A--E--E--K--E--Y--H--A--E--G--G--K--V--P--I--   878

AGTGGATGGCATTGGAATCAATTTTACACAGAATCTATACCCACCAGAGTGATGTCTGGA  2695
K--W--M--A--L--E--S--I--L--H--R--I--Y--T--H--Q--S--D--V--W--   898

GCTACGGGGTGACTGTTTGGGAGTTGATGACCTTTGGATCCAAGCCATATGACGGAATCC  2755
S--Y--G--V--T--V--W--E--L--M--T--F--G--S--K--P--Y--D--G--I--   918

CTGCCAGCGAGATCTCCTCCATCCTGGAGAAAGGAGAACGCCTCCCTCAGCCACCCATAT  2815
P--A--S--E--I--S--S--I--L--E--K--G--E--R--L--P--Q--P--P--I--   938

GTACCATCGATGTCTACATGATCATGGTCAAGTGCTGGATGATAGACGCAGATAGTCGCC  2875
C--T--I--D--V--Y--M--I--M--V--K--C--W--M--I--D--A--D--S--R--   958

CAAAGTTCCGTGAGTTGATCATCGAATTCTCCAAAATGGCCCGAGACCCCCAGCGCTACC  2935
P--K--F--R--E--L--I--I--E--F--S--K--M--A--R--D--P--Q--R--Y--   978

TTGTCATTCAGGGGGATGAAAGAATGCATTTGCCAAGTCCTACAGACTCCAACTTCTACC  2995
L--V--I--Q--G--D--E--R--M--H--L--P--S--P--T--D--S--N--F--Y--   998

GTGCCCTGATGGATGAAGAAGACATGGACGACGTGGTGGATGCCGACGAGTACCTCATCC  3055
R--A--L--M--D--E--E--D--M--D--D--V--V--D--A--D--E--Y--L--I--  1018

CACAGCAGGGCTTCTTCAGCAGCCCCTCCACGTCACGGACTCCCCTCCTGAGCTCTCTGA  3115
P--Q--Q--G--F--F--S--S--P--S--T--S--R--T--P--L--L--S--S--L--  1038

GTGCAACCAGCAACAATTCCACCGTGGCTTGCATTGATAGAAATGGGCTGCAAAGCTGTC  3175
S--A--T--S--N--N--S--T--V--A--C--I--D--R--N--G--L--Q--S--C--  1058
```

*FIG. 5 (con'd.)*

```
CCATCAAGGAAGACAGCTTCTTGCAGCGATACAGCTCAGACCCCACAGGCGCCTTGACTG 3235
P--I--K--E--D--S--F--L--Q--R--Y--S--S--D--P--T--G--A--L--T-- 1078

AGGACAGCATAGACGACACCTTCCTCCCAGTGCCTGAATACATAAACCAGTCCGTTCCCA 3295
E--D--S--I--D--D--T--F--L--P--V--P--E--Y--I--N--Q--S--V--P-- 1098

AAAGGCCCGCTGGCTCTGTGCAGAATCCTGTCTATCACAATCAGCCTCTGAACCCCGCGC 3355
K--R--P--A--G--S--V--Q--N--P--V--Y--H--N--Q--P--L--N--P--A-- 1118

CCAGCAGAGACCCACACTACCAGGACCCCCACAGCACTGCAGTGGGCAACCCCGAGTATC 3415
P--S--R--D--P--H--Y--Q--D--P--H--S--T--A--V--G--N--P--E--Y-- 1138

TCAACACTGTCCAGCCCACCTGTGTCAACAGCACATTCGACAGCCCTGCCCACTGGGCCC 3475
L--N--T--V--Q--P--T--C--V--N--S--T--F--D--S--P--A--H--W--A-- 1158

AGAAAGGCAGCCACCAAATTAGCCTGGACAACCCTGACTACCAGCAGGACTTCTTTCCCA 3535
Q--K--G--S--H--Q--I--S--L--D--N--P--D--Y--Q--Q--D--F--F--P-- 1178

AGGAAGCCAAGCCAAATGGCATCTTTAAGGGCTCCACAGCTGAAAATGCAGAATACCTAA 3595
K--E--A--K--P--N--G--I--F--K--G--S--T--A--E--N--A--E--Y--L-- 1198

GGGTCGCGCCACAAAGCAGTGAATTTATTGGAGCATGA 3633 (SEQ ID NO 2)
R--V--A--P--Q--S--S--E--F--I--G--A--*- 1210 (SEQ ID NO 1)
```

*FIG. 5 (con'd.)*

METHOD FOR TREATING GEFITINIB RESISTANT CANCER

CROSS REFERENCE TO RELATED APPLICATION

This application is a continuation of U.S. patent application Ser. No. 11/883,474, filed on Jul. 31, 2007 and having a 35 U.S.C. § 371(c) date of Aug. 5, 2008, which is the National Phase application of International Application No. PCT/US2006/003717, filed Feb. 2, 2006, which designates the United States and was published in English, and claims the priority benefit under 35 U.S.C. § 119(e) of U.S. provisional Patent Application No. 60/649,483, filed Feb. 3, 2005, and U.S. provisional Patent Application No. 60/671,989, filed Apr. 15, 2005. These applications, in their entirety, are incorporated herein by reference.

SEQUENCE LISTING

This application incorporates by reference in its entirety the Computer Readable Form (CRF) of a Sequence Listing in ASCII text format submitted via EFS-Web. The Sequence Listing text file submitted via EFS-Web, entitled 13120-023-999_SUB_SEQ_LISTING.txt, was created on Oct. 9, 2019, and is 27,630 bytes in size.

BACKGROUND

Epithelial cell cancers, for example, prostate cancer, breast cancer, colon cancer, lung cancer, pancreatic cancer, ovarian cancer, cancer of the spleen, testicular cancer, cancer of the thymus, etc., are diseases characterized by abnormal, accelerated growth of epithelial cells. This accelerated growth initially causes a tumor to form. Eventually, metastasis to different organ sites can also occur. Although progress has been made in the diagnosis and treatment of various cancers, these diseases still result in significant mortality.

Lung cancer remains the leading cause of cancer death in industrialized countries. Cancers that begin in the lungs are divided into two major types, non-small cell lung cancer and small cell lung cancer, depending on how the cells appear under a microscope. Non-small cell lung cancer (squamous cell carcinoma, adenocarcinoma, and large cell carcinoma) generally spreads to other organs more slowly than does small cell lung cancer. About 75 percent of lung cancer cases are categorized as non-small cell lung cancer (e.g., adenocarcinomas), and the other 25 percent are small cell lung cancer. Non-small cell lung cancer (NSCLC) is the leading cause of cancer deaths in the United States, Japan and Western Europe. For patients with advanced disease, chemotherapy provides a modest benefit in survival, but at the cost of significant toxicity, underscoring the need for therapeutic agents that are specifically targeted to the critical genetic lesions that direct tumor growth (Schiller J H et al., N Engl J Med, 346: 92-98, 2002).

Epidermal growth factor receptor (EGFR) is a 170 kilodalton (kDa) membrane-bound protein expressed on the surface of epithelial cells. EGFR is a member of the growth factor receptor family of protein tyrosine kinases, a class of cell cycle regulatory molecules. (W. J. Gullick et al., 1986, Cancer Res., 46:285-292). EGFR is activated when its ligand (either EGF or TGF-α) binds to the extracellular domain, resulting in autophosphorylation of the receptor's intracellular tyrosine kinase domain (S. Cohen et al., 1980, J. Biol. Chem., 255:4834-4842; A. B. Schreiber at al., 1983, J. Biol. Chem., 258:846-853).

EGFR is the protein product of a growth promoting oncogene, erbB or ErbB1, that is but one member of a family, i.e., the ERBB family of protooncogenes, believed to play pivotal roles in the development and progression of many human cancers. In particular, increased expression of EGFR has been observed in breast, bladder, lung, head, neck and stomach cancer as well as glioblastomas. The ERBB family of oncogenes encodes four, structurally-related transmembrane receptors, namely, EGFR, HER-2/neu (erbB2), HER-3 (erbB3) and HER-4 (erbB4). Clinically, ERBB oncogene amplification and/or receptor overexpression in tumors have been reported to correlate with disease recurrence and poor patient prognosis, as well as with responsiveness in therapy. (L. Harris et al., 1999, Int. J. Biol. Markers, 14:8-15; and J. Mendelsohn and J. Baselga, 2000, Oncogene, 19:6550-6565).

EGFR is composed of three principal domains, namely, the extracellular domain (ECD), which is glycosylated and contains the ligand-binding pocket with two cysteine-rich regions; a short transmembrane domain, and an intracellular domain that has intrinsic tyrosine kinase activity. The transmembrane region joins the ligand-binding domain to the intracellular domain. Amino acid and DNA sequence analysis, as well as studies of nonglycosylated forms of EGFR, indicate that the protein backbone of EGFR has a mass of 132 kDa, with 1186 amino acid residues (A. L. Ullrich et al., 1984, Nature, 309:418-425; J. Downward et al., 1984, Nature, 307:521-527; C. R. Carlin et al., 1986, Mol. Cell. Biol., 6:257-264; and F. L. V. Mayes and M. D. Waterfield, 1984, The EMBO J., 3:531-537).

The binding of EGF or TGF-α to EGFR activates a signal transduction pathway and results in cell proliferation. The dimerization, conformational changes and internalization of EGFR molecules function to transmit intracellular signals leading to cell growth regulation (G. Carpenter and S. Cohen, 1979, Ann. Rev. Biochem., 48:193-216). Genetic alterations that affect the regulation of growth factor receptor function, or lead to overexpression of receptor and/or ligand, result in cell proliferation. In addition, EGFR has been determined to play a role in cell differentiation, enhancement of cell motility, protein secretion, neovascularization, invasion, metastasis and resistance of cancer cells to chemotherapeutic agents and radiation. (M.-J. Oh et al., 2000, Clin. Cancer Res., 6:4760-4763).

A variety of inhibitors of EGFR have been identified, including a number already undergoing clinical trials for treatment of various cancers. For a recent summary, see de Bono, J. S. and Rowinsky, E. K. (2002), "The ErbB Receptor Family: A Therapeutic Target For Cancer", *Trends in Molecular Medicine*, 8, 519-26.

A promising set of targets for therapeutic intervention in the treatment of cancer includes the members of the HER-kinase axis. They are frequently upregulated in solid epithelial tumors of, by way of example, the prostate, lung and breast, and are also upregulated in glioblastoma tumors. Epidermal growth factor receptor (EGFR) is a member of the HER-kinase axis, and has been the target of choice for the development of several different cancer therapies. EGFR tyrosine kinase inhibitors (EGFR-TKIs) are among these therapies, since the reversible phosphorylation of tyrosine residues is required for activation of the EGFR pathway. In other words, EGFR-TKIs block a cell surface receptor responsible for triggering and/or maintaining the cell signaling pathway that induces tumor cell growth and division. Specifically, it is believed that these inhibitors interfere with the EGFR kinase domain, referred to as HER-1. Among the more promising EGFR-TKIs are three series of compounds: quinazolines, pyridopyrimidines and pyrrolopyrimidines.

Two of the more advanced compounds in clinical development include Gefitinib (compound ZD1839 developed by AstraZeneca UK Ltd.; available under the tradename IRESSA; hereinafter "IRESSA") and Erlotinib (compound OSI-774 developed by Genentech, Inc. and OSI Pharmaceuticals, Inc.; available under the tradename TARCEVA; hereinafter "TARCEVA"); both have generated encouraging clinical results. Conventional cancer treatment with both IRESSA and TARCEVA involves the daily, oral administration of no more than 500 mg of the respective compounds. In May, 2003, IRESSA became the first of these products to reach the United States market, when it was approved for the treatment of advanced non-small cell lung cancer patients.

IRESSA is an orally active quinazoline that functions by directly inhibiting tyrosine kinase phosphorylation on the EGFR molecule. It competes for the adenosine triphosphate (ATP) binding site, leading to suppression of the HER-kinase axis. The exact mechanism of the IRESSA response is not completely understood, however, studies suggest that the presence of EGFR is a necessary prerequisite for its action.

A significant limitation in using these compounds is that recipients thereof may develop a resistance to their therapeutic effects after they initially respond to therapy, or they may not respond to EGFR-TKIs to any measurable degree at all. The response rate to EGFR-TKIs varies between different ethnic groups. At the low end of EGFR-TKI responders, in some populations, only 10-15 percent of advanced non-small cell lung cancer patients respond to EGFR kinase inhibitors. Thus, a better understanding of the molecular mechanisms underlying sensitivity to IRESSA and TARCEVA would be extremely beneficial in targeting therapy to those individuals whom are most likely to benefit from such therapy.

There is a significant need in the art for a satisfactory treatment of cancer, and specifically epithelial cell cancers such as lung, ovarian, breast, brain, colon and prostate cancers, which incorporates the benefits of TKI therapy and overcoming the non-responsiveness exhibited by patients. Such a treatment could have a dramatic impact on the health of individuals, and especially older individuals, among whom cancer is especially common.

SUMMARY

The inventors of the present invention have surprisingly discovered that irreversible EGFR inhibitors are effective in the treatment of cancer in subjects who are no longer responding to gefitinib and/or erlotinib therapies. Thus, in one embodiment, the present invention provides a method for the treatment of gefitinib and/or erlotinib resistant cancer. In this embodiment, progression of cancer in a subject is monitored at a time point after the subject has initiated gefitinib and/or erlotinib treatment. Progression of the cancer is indicative of cancer that is resistant to gefitinib and/or erlotinib treatment and the subject is administered a pharmaceutical composition comprising an irreversible epidermal growth factor receptor (EGFR) inhibitor.

In preferred embodiments, the irreversible EGFR inhibitor EKB-569, HKI-272 or HKI-357. Alternatively, the irreversible EGFR inhibitor may be any compound which binds to cysteine 773 of EGFR (SEQ ID NO: 1).

The progression of cancer may be monitored by methods well known to those of skill in the art. For example, the progression may be monitored by way of visual inspection of the cancer, such as, by means of X-ray, CT scan or MRI. Alternatively, the progression may be monitored by way of tumor biomarker detection.

In one embodiment, the patient is monitored at various time points throughout the treatment of the cancer. For example, the progression of a cancer may be monitored by analyzing the progression of cancer at a second time point and comparing this analysis to an analysis at a first time point. The first time point may be before or after initiation of gefitinib and/or erlotinib treatment and the second time point is after the first. An increased growth of the cancer indicates progression of the cancer.

In one embodiment, the progression of cancer is monitored by analyzing the size of the cancer. In one embodiment, the size of the cancer is analyzed via visual inspection of the cancer by means of X-ray, CT scan or MRI. In one embodiment, the size of the cancer is monitored by way of tumor biomarker detection.

In one embodiment, the cancer is epithelial cell cancer. In one embodiment, the cancer is gastrointestinal cancer, prostate cancer, ovarian cancer, breast cancer, head and neck cancer, esophageal cancer, lung cancer, non-small cell lung cancer, cancer of the nervous system, kidney cancer, retina cancer, skin cancer, liver cancer, pancreatic cancer, genital-urinary cancer and bladder cancer.

In one embodiment, the size of the cancer is monitored at additional time points, and the additional time points are after the second time point.

In one embodiment, the later time point is at least 2 months after the preceding time point. In one embodiment, the later time point is at least 6 months after preceding time point. In one embodiment, the later time point is at least 10 months after preceding time point. In one embodiment, the later time point is at least one year after preceding time point.

In another embodiment, the present invention provides a method of treating cancer, comprising administering to a subject having a mutation in EGFR, namely, a substitution of a methionine for a threonine at position 790 (T790M) of SEQ ID. No. 1, a pharmaceutical composition comprising an irreversible EGFR inhibitor. The T790M mutation confers resistance to gefitinib and/or erlotinib treatment.

BRIEF DESCRIPTION OF THE FIGURES

FIG. 1A shows sequence analysis for Case 1. The T790M mutation in EGFR is present in a recurrent liver lesion after the development of clinical gefitinib resistance. (Left) The mutation was not detected in the primary lung lesion at the time of diagnosis. (Right) Both the primary lung tumor and the recurrent liver lesion harbor the L858R gefitinib-sensitizing mutation. Of note, the L858R mutation is present in the expected ratio for a heterozygous mutation in both primary and recurrent lesions, whereas T790M is detectable at low levels compared with the wild-type allele. A polymorphism (G/A) is shown in the same tracing to demonstrate equivalent representation of the two alleles in the uncloned PCR product (SEQ ID NOS 3 & 4 disclosed respectively, in order of appearance). FIG. 1B shows sequence analysis for Case 2. The T790M mutation is present within a small minority of gefitinib-resistant cells. (Left) The T790M mutation was undetectable either in the lung primary tumor or in eight recurrent liver lesions from this case by sequencing uncloned PCR products. Heterozygosity at an adjacent polymorphism (G/A) confirms amplification of both EGFR alleles from these specimens. The heterozygous gefitinib-sensitizing mutation, L861Q, was detected at the expected ratio within the primary lung tumor as well as each of the eight recurrent liver lesions (SEQ ID NOS 3 & 5 disclosed respectively, in order of appearance).

FIG. 2A shows inhibition by tyrosine kinase inhibitors of proliferation of bronchoalveolar cancer cell lines with wild-type EGFR (NCI-H1666), the activating delE746-A750 mutation in EGFR (NCI-H1650), or two representative gefitinib-resistant subclones of NCI-H1650 (G7 and C11). The effect of the reversible inhibitor gefitinib is compared with that of the irreversible inhibitor HKI-357. Comparable results were observed with the other irreversible inhibitors. Cell numbers were measured by crystal violet staining, after culture in 5% FCS, with 100 ng/ml EGFR, at 72 h after exposure to indicated drug concentrations. Each data point represents the mean of four samples. FIG. 2B shows the chemical structure of gefitinib, a reversible inhibitor of EGFR; EKB-569, an irreversible inhibitor of EGFR; and HKI-272 and HKI-357, two irreversible dual inhibitors of EGFR and ERBB2. FIG. 2C shows generation of drug-resistant NCI-H1650 cells after treatment with varying concentrations of gefitinib or the irreversible ERBB inhibitor EKB-569. Colonies were stained after 12 days in culture in the presence of inhibitors.

FIG. 3A shows cell viability after siRNA-mediated knockdown of EGFR and ERBB2 in bronchoalveolar cell lines with wild-type EGFR (NCI-H1666), compared with cells with the activating delE746-A750 mutation in EGFR (NCI-H1650) and two gefitinib-resistant derivatives (G7 and C11). Viable cells were counted 72 h after treatment with double-stranded RNA and are shown as a fraction relative to cells treated with nonspecific siRNA, with standard deviations based on triplicate samples. FIG. 3B shows inhibition of EGFR autophosphorylation (Y1068) and phosphorylation of downstream effectors AKT and MAPK (ERK) in cells treated with increasing concentrations of gefitinib or the irreversible inhibitor HKI-357, followed by a 2-h pulse with EGF. The parental cell line NCI-H1650 is compared with a representative gefitinib-resistant line, G7. Total AKT and MAPK are shown as controls; tubulin is used as loading control for total EGFR levels, which are at the lower limit of detection in these cells. FIG. 3C shows altered EGFR internalization in gefitinib-resistant NCI-H1650 (G7) cells, compared with the sensitive NCI-H1650 parental cell line. Rhodamine-tagged EGF is used to label EGFR at 5 and 20 rain, after addition of ligand. The increased internalization of EGFR in NCI-H1650 (G7) cells is most evident at 20 min. (Zeiss microscope, ×63 magnification). FIG. 3D shows immunoblotting of internalized EGFR from NCI-H1650 parental cells and the resistant derivative G7 after pulse labeling of cell surface proteins by biotinylation and chase over 20 min. The increased intracellular EGFR in NCI-H1650 (07) cells is compared with the unaltered transferrin receptor (TR) internalization.

FIG. 4A shows comparison of gefitinib and two irreversible inhibitors, HK-357 and HK-272, in their ability to suppress EGFR autophosphorylation (Y1068) and phosphorylation of downstream effectors AKT and MAPK (ERK) in the NCI-H1975 bronchoalveolar cell line, harboring both a sensitizing mutation (L858R) and the resistance-associated mutation (T790M). Total EGFR, AKT, and MAPK are shown as loading controls. FIG. 4B shows suppression of proliferation in NCI-H1975 cells harboring the L858R and T790M mutations by the three irreversible ERBB family inhibitors, compared with gefitinib.

FIG. 5 shows the nucleotide sequence (SEQ ID NO: 2) and the amino acid sequence (SEQ ID NO: 1) of EGFR.

DETAILED DESCRIPTION

Gefitinib and Erlotinib Resistant Cancers

Figure 1A:
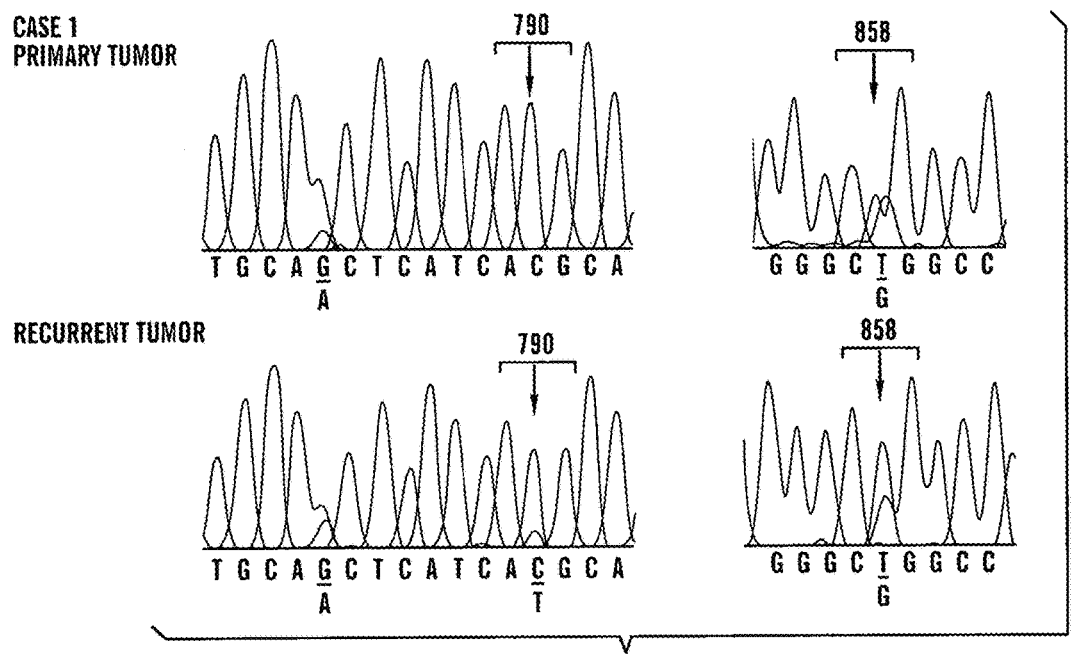
FIGS. 1A-1B show EGFR sequence analysis in recurrent metastatic lesions from two NSCLC patients with acquired gefitinib resistance.

Gefitinib (compound ZD1839 developed by AstraZencca UK Ltd.; available under the tradename IRESSA) and erlotinib (compound OSI-774 developed by Genentech, Inc. and OSI Pharmaceuticals, Inc.; available under the trade name TARCEVA) induce dramatic clinical responses in cases of non-small cell lung cancers (NSCLCs) harboring activating mutations in the EGF receptor (EGFR) (1-3), which is targeted by these competitive inhibitors of ATP binding (4, 5). The effectiveness of these tyrosine kinase inhibitors may result both from alterations in the ATP cleft associated with these mutations, which lead to enhanced inhibition of the mutant kinase by these drugs, and from biological dependence of these cancer cells on the increased survival signals transduced by the mutant receptors, a phenomenon described as "oncogene addiction" (6, 7).

Although therapeutic responses to both gefitinib and erlotinib can persist for as long as 2-3 years, the mean duration of response in most cases of NSCLC is only 6-S months (8-10). The mechanisms underlying acquired drug resistance are not well understood. By analogy with imatinib (GLBEVEC), which inhibits the BCR-ABL kinase involved in chronic myeloid leukemias (CMLs), the C-KIT kinase implicated in gastrointestinal stromal tumors (GISTs), and the FIP1L1-PDOFR-α kinase in idiopathic hypereosinophilic syndrome (HES), secondary kinase domain mutations can potentially suppress drug binding (11-16). However, recurrent NSCLC is not readily biopsied; hence, only limited clinical specimens are available for analysis. Recently, a single secondary mutation, T790M, within the EGFR kinase domain has been reported in three of six cases with recurrent disease after gefitinib or erlotinib therapy (17, 18). Codon 315 of BCR-ABL, which is analogous to EGFR codon 790, is frequently mutated in imatinib-resistant CML (11, 12), and mutation of the corresponding residue in C-KIT (codon 670) and FIP1L1-PDGFR-α (codon 674) is associated with imatinib-resistant GIST and HES, respectively (15, 16). Early in vitro modeling of resistance to EGFR inhibitors indicated that mutation of codon 790 within the wild-type receptor would similarly suppress inhibition by an EGFR tyrosine kinase inhibitor (19). Recently, transfected EGFR proteins containing activating mutations together with the T790M substitution were shown to exhibit reduced inhibition by gefitinib and erlotinib (17, 18). Although the T790M mutation seems to contribute to acquired resistance in some cases of NSCLC, the mechanisms underlying treatment failure in cases lacking secondary EGFR mutations remain unexplained.

In contrast to the cytoplasmic kinase BCR-ABL, signaling by the membrane-bound EGFR involves a complex pathway of ligand binding, receptor homodimerization, and heterodimerization with ERBB2 and other family members, followed by internalization and recycling of the ligand-bound receptor or ubiquitin-mediated receptor degradation (20). Significant EGF-dependent signaling is thought to occur during the process of internalization, which is also associated with the dissociation of EGFR complexes at the low pH of intracellular vesicles. As such, multiple factors modulate the strength and quality of the signal transduced by the receptor, and alterations in EGFR trafficking have been closely linked with the regulation of EGF-dependent cellular responses (20).

The present invention is based on the discovery that gefitinib resistant cancers can include those wherein the T790M EGFR mutation is only present in a subset of resistant tumor cells and those wherein the T790M mutation is not observed, but increased EGFR internalization is observed. The invention is further based on the discovery that irreversible EGFR inhibitors, which covalently cross-link the receptor, are effective in inhibiting cancers with the T790M mutation and in cancers with altered EGFR trafficking that can make such cancers resistance to treatment with gefitinib and/or erlotinib. Accordingly, the present invention provides a method of treating gefitinib and/or erlotinib resistant cancers comprising administering irreversible EGFR inhibitors.

Method of Treating a Patient

In one embodiment, the invention provides a method for treating gefitinib/erlotinib resistant cancer. The method comprises administering to a patient in need of such treatment an effective amount of certain irreversible EGFR inhibitors, including EKB-569 (4-anilinoquinoline-3-carbonitrile; Greenberger et al., 11$^{th}$ NCI-EORTC-AACR Symposium on New Drugs in Cancer Therapy, Amsterdam, Nov. 7-10, 2000, abstract 388; Wyeth), HKI-357 (a derivative of 4-anilinoquinoline-3-carbonitrile; Tsou et al. J. Med. Chem. 2005, 48: 1107-1131; Wyeth) and/or HKI-272 (a derivative of 4-anilinoquinoline-3-carbonitrile; Rabindran et al., Cancer Res. 2004, 64, 3958-3965; Wyeth). In one preferred embodiment, the invention provides a method comprising administering to a patient in need of such treatment an effective amount of EKB-569. In one preferred embodiment, the invention provides a method comprising administering to a patient in need of such treatment an effective amount of HKI-357.

The treatment may also involve a combination of treatments, including, but not limited to a tyrosine kinase inhibitor in combination with other tyrosine kinase inhibitors, chemotherapy, radiation, etc.

Cancers may initially be diagnosed as gefitinib/erlotinib sensitive or predicted to be gefitinib/erlotinib sensitive by means of the methods described in Lynch et al., 2004; 350:2129-2139. Gefitinib/erlotinib sensitivity may be predicted by the presence in the tumor of EGFR mutations including, for example, deletion of residues 747 (lysine) to 749 (glutamic acid) combined with a mutation in 750 (alanine), deletion of residues 747 (lysine) to 750 (alanine), substitution of arginine for leucine at residue 858, of substitution of glutamine for leucine at residue 861.

Cancers may be diagnosed as gefitinib and/or erlotinib resistant after treatment with gefitinib and/or erlotinib has commenced. Alternatively, cancers may be diagnosed as gefitinib and/or erlotinib resistant prior to initiation of treatment with such compounds. Gefitinib and/or erlotinib resistance in the tumor may occur after, e.g., 6 months or longer of gefitinib and/or erlotinib treatment. Alternatively, gefitinib and/or erlotinib resistance of the tumor may be diagnosed less than 6 months after gefitinib and/or erlotinib treatment has commenced. Diagnosis of gefitinib and/or erlotinib resistance may be accomplished by way of monitoring tumor progression during gefitinib and/or erlotinib treatment. Tumor progression may be determined by comparison of tumor status between time points after treatment has commenced or by comparison of tumor status between a time point after treatment has commenced to a time point prior to initiation of gefitinib and/or erlotinib treatment. Tumor progression may be monitored during gefitinib and/or erlotinib treatment visually, for example, by means of radiography, for example, X-ray, CT scan, or other monitoring methods known to the skilled artisan, including palpitation of the cancer or methods to monitor tumor biomarker levels. Progression of the cancer during treatment with gefitinib and/or erlotinib indicates gefitinib and/or erlotinib resistance. A rise in level of tumor biomarkers indicates tumor progression. Thus, a rise in tumor biomarker levels during treatment with gefitinib and/or erlotinib indicates gefitinib and/or erlotinib resistance. Detection of new tumors or detection of metastasis indicates tumor progression. Cessation of tumor shrinkage indicates tumor progression. Growth of the cancer is indicated by, for example, increase in tumor size, metastasis or detection of new cancer, and/or a rise in tumor biomarker levels.

The development of gefitinib and/or erlotinib resistance may be monitored by means of testing for presence of a gefitinib and/or erlotinib resistance associated mutation in circulating tumor cells obtained from the circulation, or other bodily fluid, of the subject. Presence of gefitinib and/or erlotinib resistance associated mutations in tumor cells from the subject is indicative of a gefitinib and/or erlotinib resistant tumor.

In one embodiment, the subject's tumor harbors mutations indicative of gefitinib and/or erlotinib sensitivity, yet it is resistant to gefitinib and/or erlotinib treatment. In one embodiment, the subject's tumor harbors mutations indicative gefitinib and/or erlotinib sensitivity and harbors mutations indicative of gefitinib and/or erlotinib resistance, e.g., the T790M mutation, that is, where a methione residue is substituted for the native threonine residue, in EGFR, e.g. increased EGFR internalization. In one embodiment, the subject's tumor does not harbor mutations indicative of gefitinib and/or erlotinib sensitivity and does harbor mutations indicative of gefitinib and/or erlotinib resistance, e.g., the T790M mutation in EGFR, e.g., increased EGFR internalization.

In connection with the administration of the drug, an "effective amount" indicates an amount that results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

The effective dosage of active ingredient employed may vary depending on the particular compound employed, the mode of administration and the severity of the condition being treated. The skilled artisan is aware of the effective dose for each patient, which may vary with disease severity, individual genetic variation, or metabolic rate. However, in general, satisfactory results are obtained when the compounds of the invention are administered at a daily dosage of from about 0.5 to about 1000 mg/kg of body weight, optionally given in divided doses two to four times a day, or in sustained release form. The total daily dosage is projected to be from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like. The compounds of the invention can be administered parenterally by injection or by gradual infusion over time and can be delivered by peristaltic means.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the invention are formulated into conventional oral administration forms such as capsules, tablets and tonics.

For topical administration, the pharmaceutical composition (inhibitor of kinase activity) is formulated into ointments, salves, gels, or creams, as is generally known in the art.

The therapeutic compositions of this invention, e.g. irreversible EGFR inhibitors, are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluents; i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

The therapeutic composition useful for practicing the methods of the present invention, e.g. irreversible EGFR inhibitors, are described herein. Any formulation or drug delivery system containing the active ingredients, which is suitable for the intended use, as are generally known to those of skill in the art, can be used. Suitable pharmaceutically acceptable carriers for oral, rectal, topical or parenteral (including inhaled, subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

Formulations suitable for parenteral administration conveniently include sterile aqueous preparation of the active compound which is preferably isotonic with the blood of the recipient Thus, such formulations may conveniently contain distilled water, 5% dextrose in distilled water or saline. Useful formulations also include concentrated solutions or solids containing the compound which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethyl-ammonio-1-propanesulfonate), Big-CHAPS (N, N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

In one embodiment, the tyrosine kinase inhibitor of the present invention can be formulated into a liposome or microparticle which is suitably sized to lodge in capillary beds following intravenous administration. When the liposome or mnicroparticle is lodged in the capillary beds surrounding ischemic tissue, the agents can be administered locally to the site at which they can be most effective. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

The formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Compounds of the present methods (i.e. irreversible EGFR inhibitors) may be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, more preferably between 2 and 5 microns.

Generally for nasal administration a mildly acid pH will be preferred. Preferably the compositions of the invention have a pH of from about 3 to 5, more preferably from about 3.5 to about 3.9 and most preferably 3.7. Adjustment of the pH is achieved by addition of an appropriate acid, such as hydrochloric acid.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The irreversible kinase inhibitors of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers am sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

Definitions

The terms "ErbB1", "epidermal growth factor receptor" and "EGFR" are used interchangeably herein and refer to native sequence EGFR as disclosed, for example, in Carpenter et al. Ann. Rev. Biochem. 56:881-914 (1987), including variants thereof (e.g. a deletion mutant EGFR as in Humphrey et al. PNAS (USA) 87:4207-4211 (1990)). erbB1 refers to the gene encoding the EGFR protein product. As used herein, the EGFR protein is disclosed as GenBank accession no. NP_005219 (SEQ ID NO: 1) which is encoded by the erbB1 gene, GenBank accession no. NM_005228 (SEQ ID NO: 2). Nucleotide and amino acid sequences of erbB1/EGFR may be found in FIG. 5.

The term "kinase activity increasing nucleic acid variance" as used herein refers to a variance (i.e. mutation) in the nucleotide sequence of a gene that results in an increased kinase activity. The increased kinase activity is a direct result of the variance in the nucleic acid and is associated with the protein for which the gene encodes.

The term "drug" or "compound" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

Nucleic acid molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994).

As used herein, a "cancer" in a subject or patient refers to the presence of cells possessing characteristics typical of cancer-causing cells, such as uncontrolled proliferation, immortality, metastatic potential, rapid growth and proliferation rate, and certain characteristic morphological features. In some circumstances, cancer cells will be in the form of a tumor, or such cells may exist locally within an animal, or circulate in the blood stream as independent cells.

EXAMPLES

Compounds. Compounds used herein, including EKB-569, HK1-357, and HK1-272 as described in U.S. Pat. No. 6,002,008; Greenberger et al., Proc. 11$^{th}$ NCI EORTC-AACR Symposium on New Drugs in Cancer Therapy, Clinical Cancer Res. Vol. 6 Supplement, November 2000, ISSN 1078-0432; in Rabindran et al., Cancer Res. 64: 3958-3965 (2004); Holbro and Hynes, Ann. Rev. Pharm. Tox. 44:195-217 (2004); and Tejpar et al., J. Clin. Oncol. ASCO Annual Meeting Proc. Vol. 22, No. 14S: 3579 (2004).

Analysis of Recurrent NSCLC and Generation of Gefitinib-Resistant NCI-H1650 Cells. Clinical specimens of recurrent NSCLC were obtained at autopsy after appropriate consent. The entire kinase domain of EGFR was sequenced after analysis of uncloned PCR products. Multiple clones of exon 20 were sequenced to examine codon 790. Mutational analysis of EGFR (exons 1-28), ERBB2 (exons 1-24), PTEN (exons 1-9), Kras (codons 12, 13, and 61), and p53 (exons 5-8) in gefitinib-resistant clones as well as the parental NCI-H1650 cell line was performed by automated sequencing of individual exons and flanking intronic sequence (PCR conditions available on request) with bidirectional sequencing by using dye terminator chemistry (BIGDYE version 1.1, Applied Biosystems). Sequencing reactions were run on an ABI3100 sequencer (Applied Biosystems), and electropherograms were analyzed by using SEQUENCE NAVIGATOR and FACTURA software (Applied Biosystems).

To generate resistant subclones of NCI-H1650 cells, these were treated with ethyl methane sulfonate (EMS; 600 μg/ml), allowed to recover for 72 h, and then seeded at a density of $6 \times 10^4$ cells per 10-cm$^2$ dish in 20 μM gefitinib. Relative resistance of these cells to gefitinib, compared with the irreversible inhibitors, was achieved by seeding $5 \times 10^4$ cells in six-well plates in 5% FCS and 100 ng/ml EGF (Sigma), in the presence of varying concentrations of drugs, followed after 72 h by fixing cells with 4% formaldehyde, staining with 0.1% crystal violet, and quantifying cell mass by using the Odyssey Infrared Imaging System (LI-COR Biosciences, Lincoln, Nebr.). For small interfering RNA (siRNA) knockdown experiments, cells were transfected with double-stranded RNA oligonucleotides targeting EGFR, ERBB2 (both SMARTpool from Dharmacon, Lafayette, Colo.), or nonspecific control (LRT1B), using X-treme GENE transfection reagent (Roche Applied Science). After 72 h, cells were stained with crystal violet and analyzed on the Odyssey Infrared scanner.

Immunoblotting and Signaling Studies. Inhibition of EGFR signaling by increasing concentrations of gefitinib or the irreversible inhibitors was determined by seeding $9 \times 10^4$ cells in 24-well plates, adding the drugs to medium containing 5% FCS for 15 min, followed by a 2-h pulse with 100 ng/ml EGF, and harvesting of lysates. Lysates were prepared in 2× gel loading buffer, sonicated, boiled, and then separated by 10% SDS/PAGE, followed by electrotransfer to polyvinylidene fluoride (PVDF) membranes, and immunoblotting. Antibodies used were phospho-EGFR Y1068 and phospho-mitogen-activated protein kinase (MAPK) (Cell Signaling Technology, Beverly, Mass.), phospho-AKT (BioSource International, Camarillo, Calif.), and total EGFR, MAPK, AKT, and tubulin (Santa Cruz Biotechnology).

Analysis of EGFR Internalization. To demonstrate internalization of EGFR by fluorescence microscopy, cells were grown on coverslips and incubated with 1 ng/ml recombinant human (rh) EGF (Molecular Probes, Eugene, Oreg.) for various intervals before fixing in 4% paraformaldehyde for 10 min. Coverslips were washed in PBS and mounted with ProLong Gold antifade reagent (Molecular Probes). To quantify EGFR internalization by cell surface biotinylation, cells were grown to confluency, pretreated with cyclohexamide, incubated on ice for 1 h with 1.5 mg/ml sulfosuccinimidyl-2-(biotinamido)ethyl-1,3-dithiopropionate (sulfo-NHS-SS-biotin; Pierce), and washed with blocking buffer (50 nM NH$_4$CL/1 mM MgCl$_2$/0.1 mM CaCl$_2$ in PBS) to quench free sulfo-NHS-SS-biotin, followed by several further washes with PBS. The cells were then incubated in culture medium at 37° C. for various intervals to allow internalization of the biotinylated molecules, washed twice for 20 min in a glutathione solution (50 mM glutathione/75 mM NaCl/75 mM NaOH/1% BSA) on ice to strip all of the biotinyl groups from the cell surface, and then scraped and lysed in 500 μM radioimmunoprecipitation assay (RIPA) buffer (25 mM Tris-HCl, pH 7.4, with 150 mM NaCL/0.1% SDS/1% Triton X-100) supplemented with NaF, Na-orthovanadate, and protease inhibitors. Cell extracts were centrifuged, and the supernatants were incubated with streptavidin beads (Sigma) to collect the biotinylated proteins, which were then analyzed by SDS/PAGE and immunoblotting with anti-EGFR antibody (SC-03, Santa Cruz Biotechnology) or antibody against transferrin receptor (Santa Cruz Biotechnology).

Results and Discussion

Analysis of Recurrent Lung Cancers with Acquired Resistance to Gefitinib. Recurrent gefitinib-resistant NSCLC developed in two patients whose tumors had harbored an activating mutation of the EGFR kinase at the time of diagnosis and who had shown a dramatic initial clinical response to the drug (1). In both cases, progressive metastatic disease in the liver led to the patients' demises, 1-2 years after initiation of treatment. In case 1, analysis of the major liver metastasis obtained at the time of autopsy indicated persistence of the sensitizing EGFR mutation (L858R), as well as the presence of a newly acquired T790M mutation (FIG. 1A). Interestingly, analysis of uncloned PCR products showed the initial L858R mutation to be present at an abundance consistent with a heterozygous mutation that is present in all tumor cells, whereas the secondary T790M mutation was seen at approximately one-fifth the abundance of the corresponding wild-type allele. Thus, this resistance-associated mutation seems to be present in only a fraction of cells within the recurrent tumor.

Figure 1B:
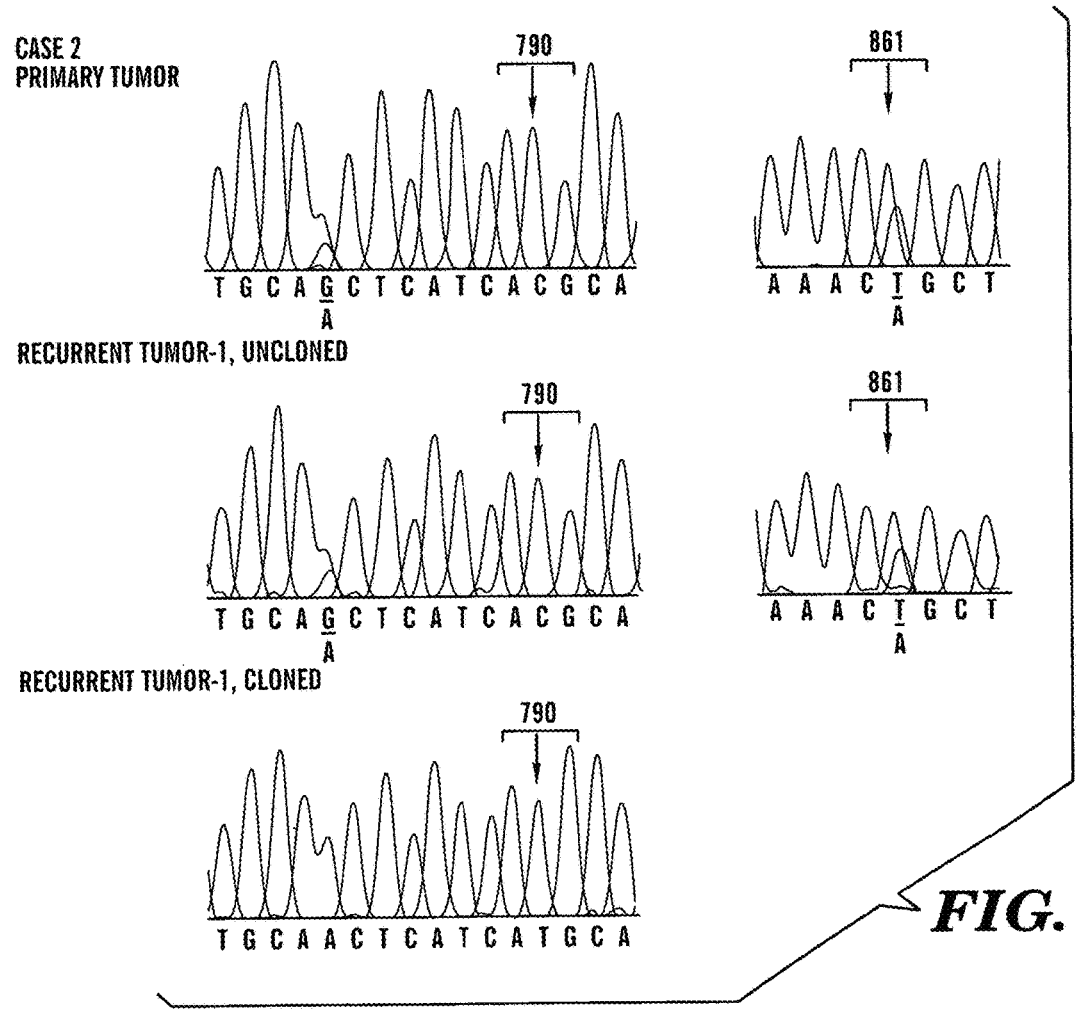

Case 2 involved eight distinct recurrent metastases in the liver after the failure of gefitinib therapy. In all of these independent lesions, the sensitizing L861Q EGFR mutation was present at the expected ratio for a heterozygous mutation. No secondary EGFR mutation was detectable by analysis of uncloned PCR products from any of these metastases. However, after subcloning of the PCR products, the T790M mutation was found to be present at very low frequency in two of the four metastatic tumors analyzed (T790M, 2 of 50 clones sequenced from lesion 1 and 1 of 56 from lesion 2), but not from two other recurrent metastases (0 of 55 clones from lesion 3 and 0 of 59 from lesion 4), or the primary tumor (0 of 75 clones) (FIG. 1B and Table 1). Taken together, these results are consistent with previous reports that the T790M mutation is present in some, but not all, cases of acquired gefitinib resistance (three of seven tumors; see refs. 17, 18, and 21). Furthermore, as previously noted (18), even in some cases with this resistance-associated mutation, it seems to be present in only a small fraction of tumor cells within a recurrent lesion. These observations suggest that additional mechanisms of resistance are involved in cases without a secondary EGFR mutation and that such mechanisms coexist with the T790M mutation in other cases.

Figure 2A:
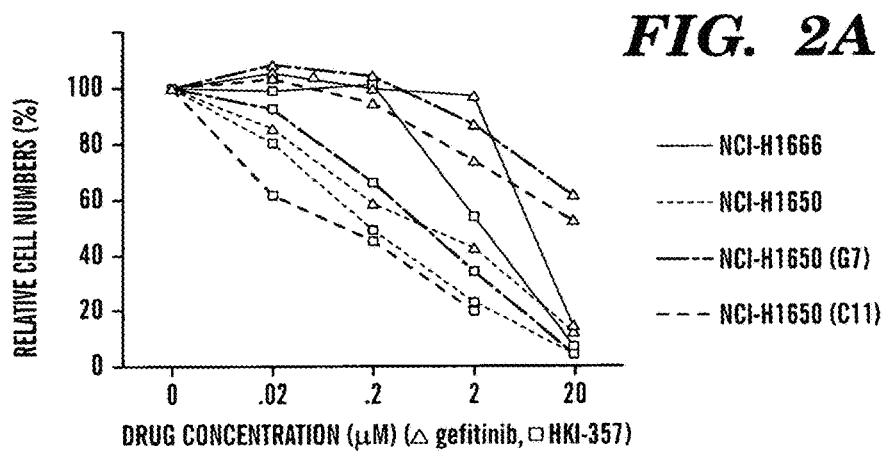
FIGS. 2A-2C show acquired resistance to gefitinib in bronchoalveolar cancer cell lines and persistent sensitivity to irreversible ERBB family inhibitors.
Figure 2B:
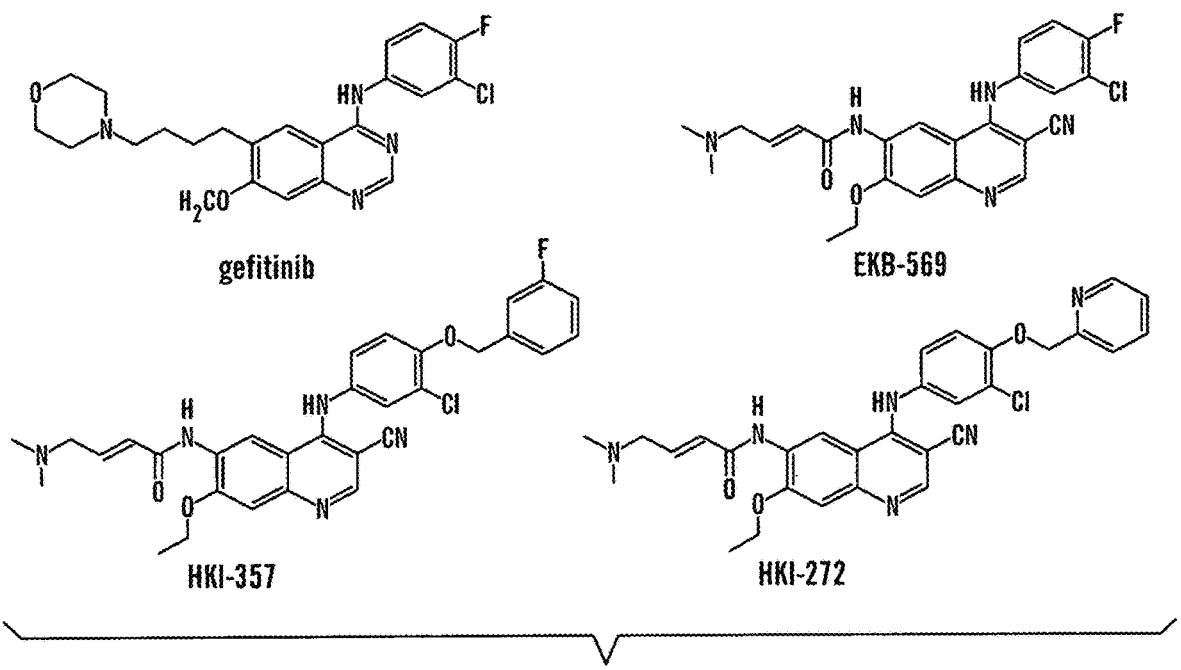
Figure 2C:
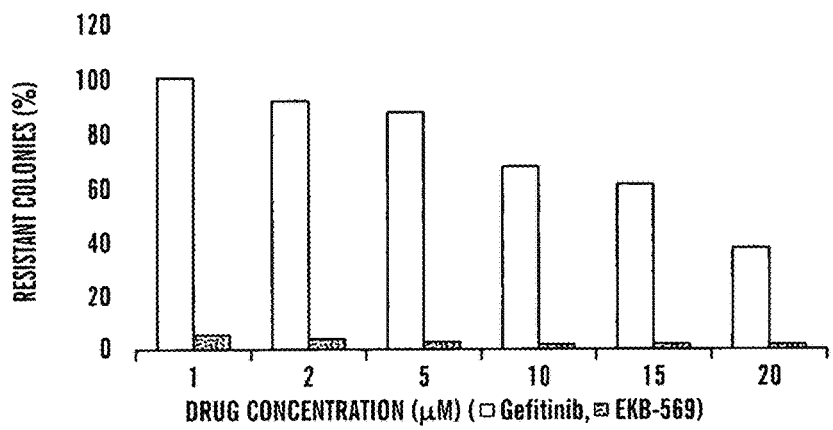

Generation of Gefitinib-Resistant Cell Lines with Susceptibility to Irreversible Inhibitors. Given the excellent correlation between the clinical responsiveness of EGFR-mutant NSCLC and the enhanced gefitinib-sensitivity of NSCLC cell lines with these mutations (2, 6, 22, 23), and the limited availability of clinical specimens from relapsing patients, we modeled gefitinib resistance in vitro. We cultured the bronchoalveolar cancer cell line NCI-H1650, which has an in-frame deletion of the EGFR kinase (delE746-A750), in 20 μM gefitinib, either with or without prior exposure to the mutagen ethyl methane sulfonate. This cell line exhibits 100-fold increased sensitivity to gefitinib, compared with some NSCLC lines expressing wild-type EGFR (6). Whereas the vast majority of these cells are efficiently killed by 20 μM gefitinib, drug-resistant colonies were readily observed at a frequency of $\approx 10^{-5}$, irrespective of mutagen treatment. Forty-nine independent drug-resistant clones were isolated, showing an average 50-fold decrease in gefitinib sensitivity (FIG. 2A). All of these showed persistence of the sensitizing mutation without altered expression of EGFR, and none had acquired a secondary EGFR mutation or new mutations in ERBB2, p53, Kas, or PTEN. Gefitinib-resistant clones demonstrated comparable resistance to related inhibitors of the anilinoquinazoline class. Remarkably, however, they displayed persistent sensitivity to three inhibitors of the ERBB family (FIG. 2A): HKI-272 (24) and HKI-357 (compound 7f in ref. 25), which are dual inhibitors of EGFR and ERBB2 ($IC_{50}$ values of 92 and 34 nM, respectively, for EGFR and 59 and 33 nM, respectively, for ERBB2), and EKB-569 (26), a selective inhibitor of EGFR ($IC_{50}$ values of 39 nM for EGFR and 1.3 μM for ERBB2) (Wyeth) (FIG. 2B). All three drugs are irreversible inhibitors, most likely via a covalent bond with the cys773 residue within the EGFR catalytic domain or the cys805 of ERBB2. Like gefitinib, these compounds demonstrate increased killing of NSCLC cells harboring an EGFR mutation, compared with cells expressing wild-type receptor (FIG. 2A). However, in contrast to gefitinib, against which resistant clones are readily generated, even at high drug concentrations, we were unable to establish clones of cells that were resistant to the irreversible inhibitors at concentrations above 10 μM, even after ethyl methane sulfonate mutagenesis (FIG. 2C).

Figure 3A:
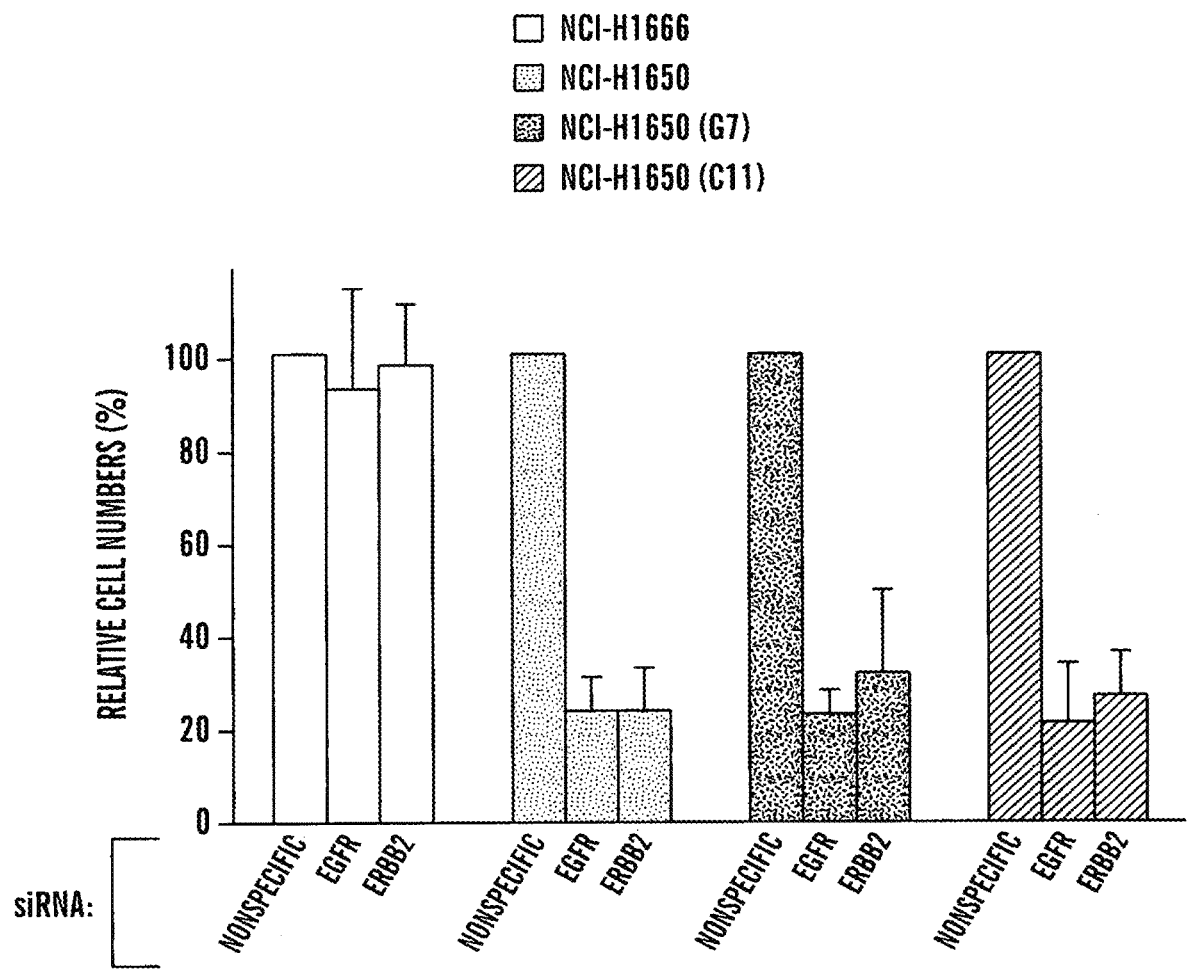
FIGS. 3A-3D show persistent dependence on EGFR and ERBB2 signaling in gefitinib-resistant cells, and altered receptor trafficking.

Dependence of Gefitinib-Resistant Cells on EGFR and ERBB2 Expression. To gain insight into the mechanisms underlying the acquisition of gefitinib resistance and the persistent sensitivity to the irreversible inhibitors, we first determined whether resistant cell lines remain dependent upon EGFR for their viability. We have previously shown that siRNA-mediated knockdown of EGFR triggers apoptosis in cells harboring mutant EGFRs, but not in those with wild-type alleles (6). Significantly, parental NCI-H1650 cells as well as their gefitinib-resistant derivatives showed comparable reduction in cell viability after transfection with siRNA targeting EGFR (FIG. 3A). Thus, acquisition of gefitinib-resistance does not involve EGFR-independent activation of downstream effectors. Because HKI-272 and HKI-357 target both EGFR and ERBB2, we also tested suppression of this related receptor. Knockdown of ERBB2 in NCI-H1650 and its gefitinib-resistant derivatives also caused loss of viability (FIG. 3A), suggesting a role for EGFR-ERBB2 heterodimers in transducing essential survival signals in tumor cells harboring EGFR mutations. Inhibition of EGFR alone by an irreversible inhibitor seems to be sufficient to induce apoptosis in gefitinib-resistant cells, as demonstrated by the effectiveness of EKB-569, which primarily targets EGFR (26). However, given the potentially complementary effects of targeting both EGFR and ERBB2 by using siRNA and the availability of irreversible inhibitors that target both of these family members, the potential benefit of dual inhibition warrants consideration.

Figure 3B:
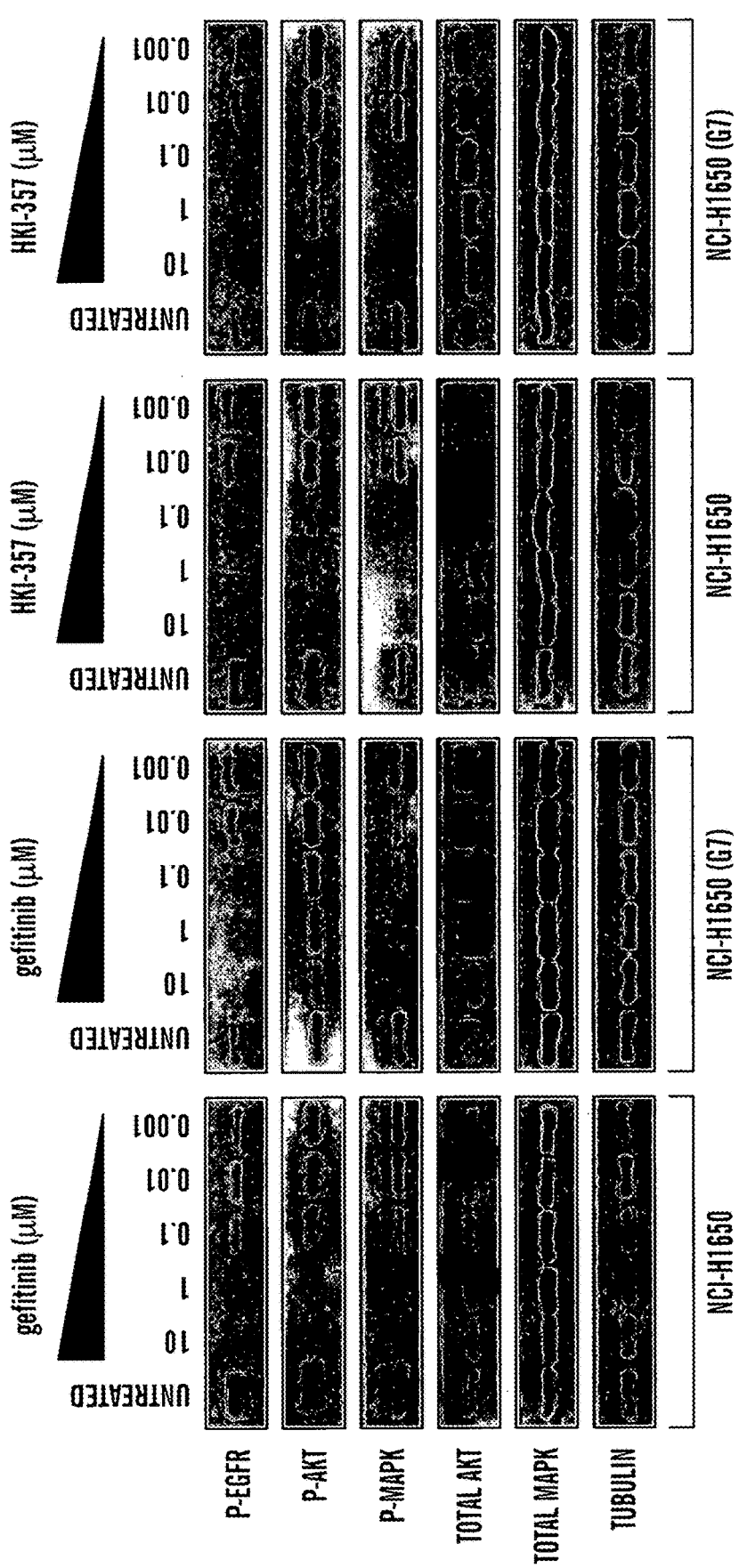

We compared the ability of gefitinib and irreversible ERBB family inhibitors to suppress signaling via downstream effectors of EGFR that mediate its proliferative and survival pathways. HKI-357 was 10-fold more effective than gefitinib in suppressing EGFR autophosphorylation (measured at residue Y1068), and AKT and MAPK phosphorylation in parental NCI-H1650 cells harboring the delE746-A750 EGFR mutation (FIG. 3B). In a gefitinib-resistant derivative, NCI-H1650(G7), gefitinib exhibited considerably reduced efficacy in suppressing AKT phosphorylation, a key EGFR signaling effector linked to gefitinib responsiveness (6), whereas HKI-357 demonstrated persistent activity (FIG. 3B).

Figure 3D:
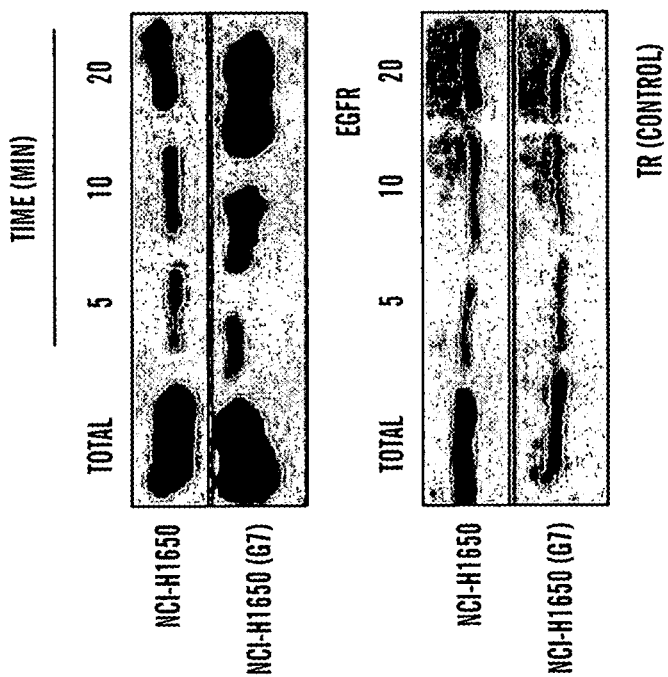
Figure 3C:
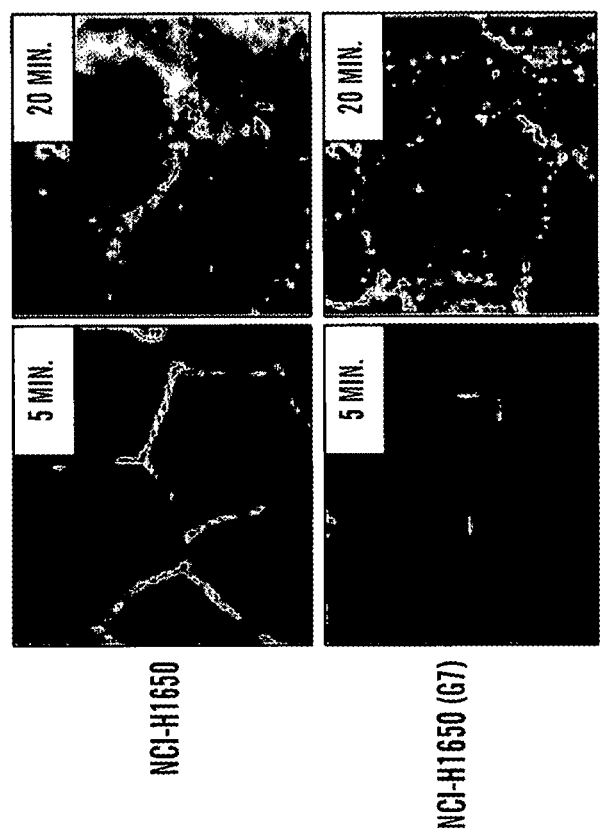

Altered EGFR Internalization in Gefitinib-Resistant Clones. Given the absence of secondary mutations in EGFR and the persistent susceptibility of gefitinib-resistant cells to siRNA-mediated suppression of EGFR, we tested whether the mechanism underlying the differential inhibition of EGFR signaling in gefitinib-resistant cells by reversible and irreversible inhibitors might be correlated with alterations in receptor trafficking, a well documented modulator of EGFR-dependent signaling (20). Indeed, analysis of EGFR trafficking in NCI-H1650-derived resistant cells demonstrated a consistent increase in EGFR internalization, compared with the parental drug-sensitive cells, as measured both by internalization of fluorescein-labeled EGF (FIG. 3C) and quantitation of cytoplasmic biotinylated EGFR (FIG. 3D). No such effect was observed with the transferrin receptor, suggesting that this did not result from a generalized alteration in all receptor processing. Although further work is required to define the precise mechanism for this alteration in EGFR trafficking, a complex process in which numerous regulatory proteins have been implicated, these results suggest that gefitinib's ability to inhibit EGFR activation is compromised in these cells, whereas the action of the irreversible inhibitors are not detectably affected.

Figure 4A:
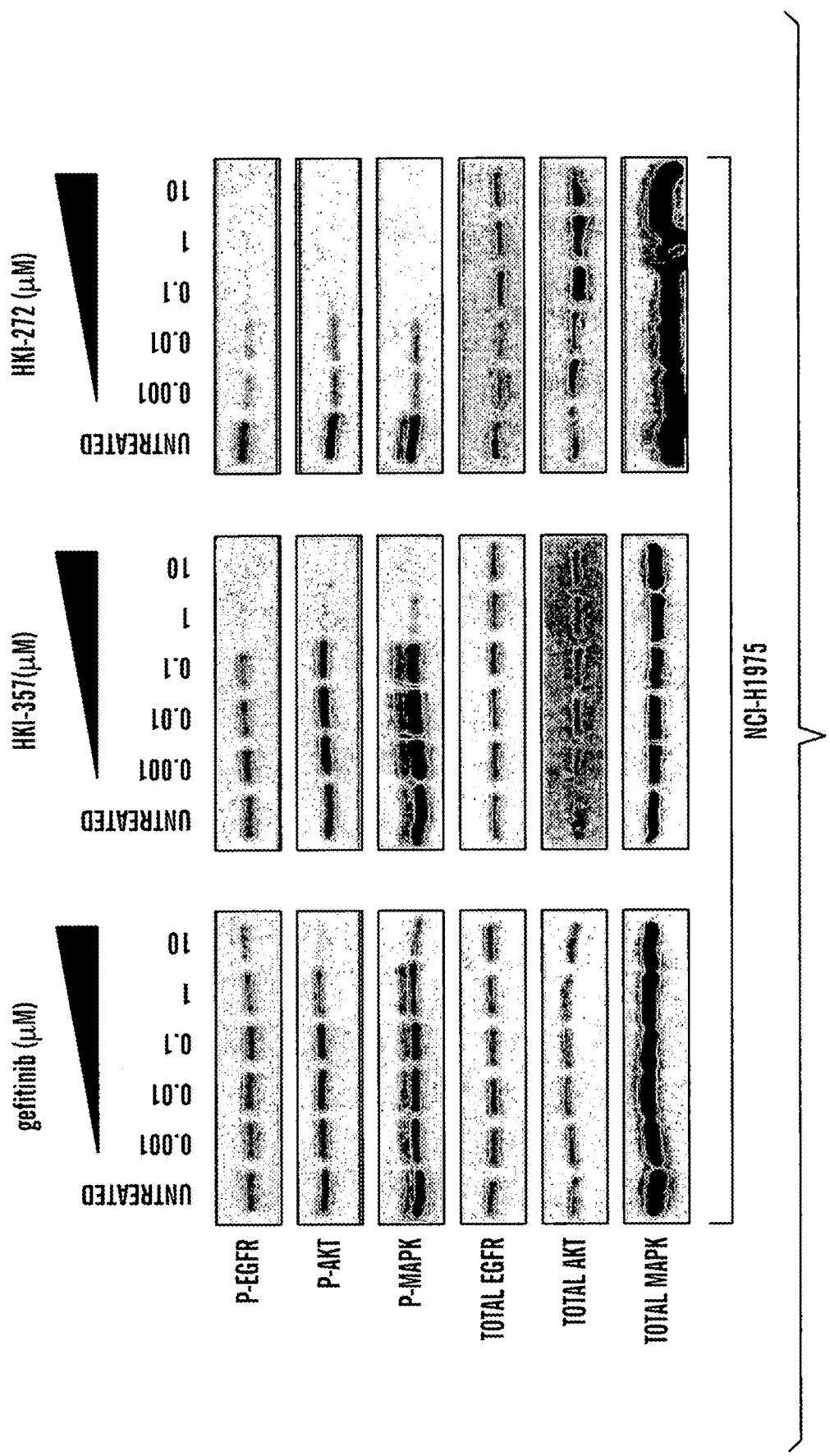
FIGS. 4A-4B show Effectiveness of irreversible ERBB inhibitors in suppressing the T790M EGFR mutant.
Figure 4B:
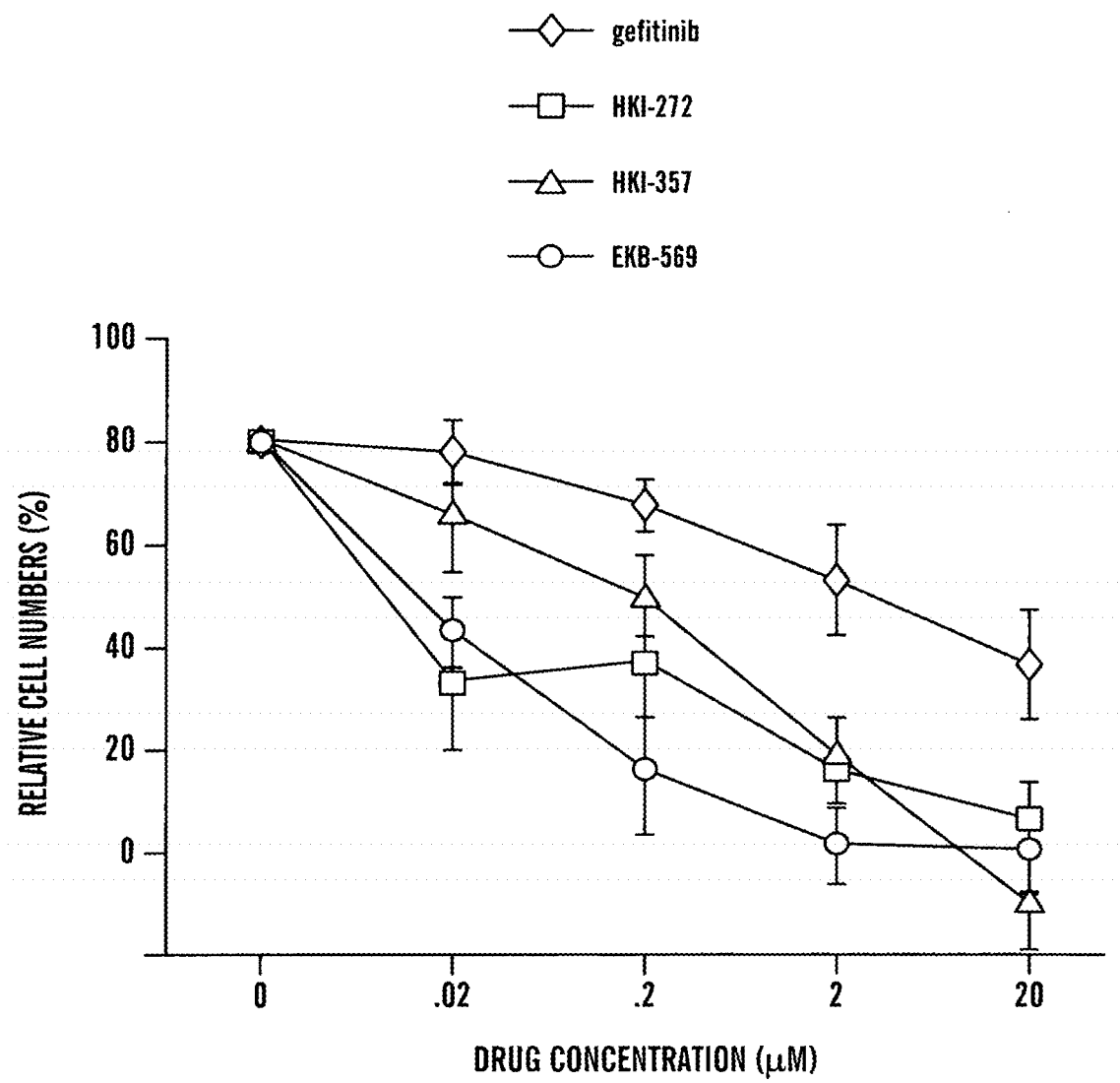
Figure 6:
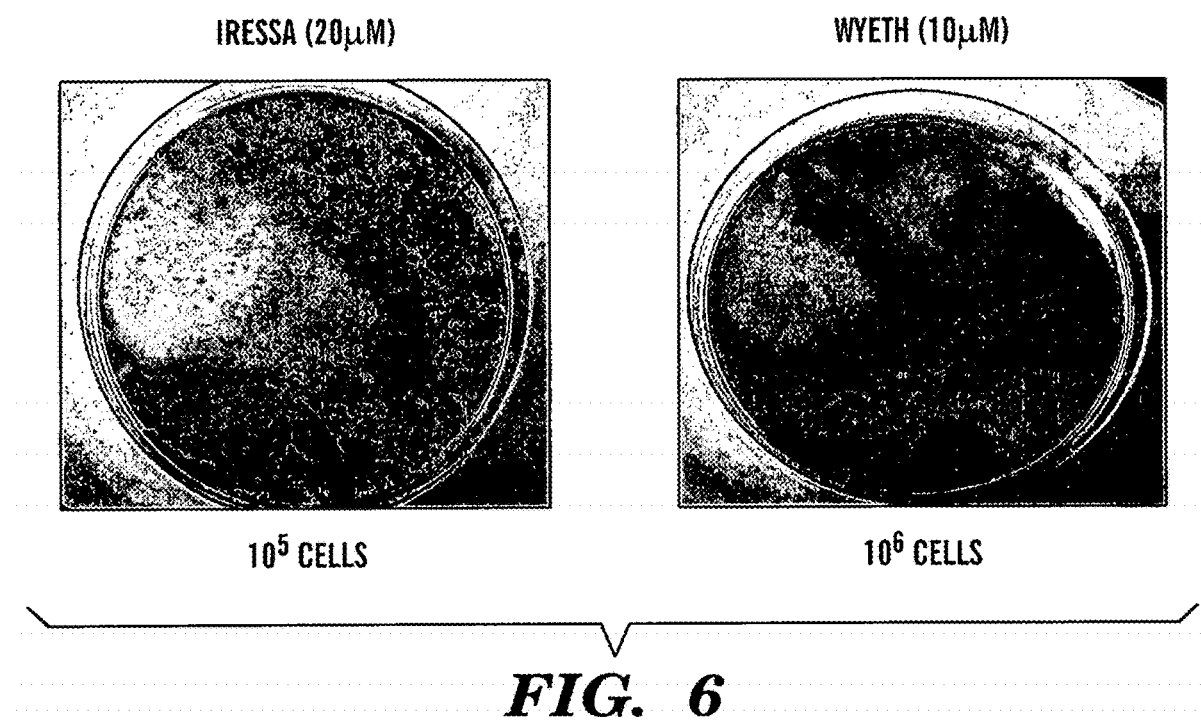
FIG. 6 shows that like gefitinib, HKI 357 and EKB 569 (labeled "Wyeth") demonstrated increased cell killing of NSCLC cells harboring an EGFR mutation, but unlike gefitinib, clones resistant to these drugs were not readily generated in vitro and they retained their effectiveness against gefitinib-resistant clones.

Inhibition of T790M EGFR Signaling and Enhanced Cell Killing by Irreversible Inhibitors. The enhanced suppression of EGFR signaling by irreversible ERBB inhibitors raised the possibility that these drugs may also exhibit persistent activity in the context of cells harboring the T790M secondary mutation in EGFR. We therefore tested the effect of these inhibitors on the NCI-H1975 bronchoalveolar cancer cell line, which harbors both L858R and T790M mutations in EGFR (18). Significantly, this cell line was derived from a patient that had not been treated with an EGFR inhibitor, indicating that this mutation is not uniquely associated with acquired drug resistance. Both HKI-357 and HKI-272 were considerably more effective than gefitinib in suppressing ligand-induced EGFR autophosphorylation and its downstream signaling, as determined by AKT and MAPK phosphorylation (FIG. 4A). Similarly, all three irreversible inhibitors suppressed proliferation, in this cell line under conditions where it is resistant to gefitinib (FIG. 4B). Thus, irreversible ERBB inhibitors seem to be effective in cells harboring the T790M EGFR as well as in cells with altered trafficking of the wild-type receptor.

Our results confirm the report of T790M mutations in EGFR as secondary mutations that arise in previously sensitive NSCLCs harboring an activating mutation, associated with the emergence of acquired resistance (17, 18). However, this mutation is present only in a subset of cases, and even tumors that harbor the T790M mutation may contain only a small fraction of cells with this mutation. These observations imply that multiple resistance mechanisms can coexist in recurrent tumors after an initial response to gefitinib or similar reversible EGFR inhibitors. Moreover, these findings suggest that T790M-independent resistance mechanisms may be equally, if not more, effective than the T790M substitution itself in conferring drug resistance and may explain why recurrent tumors rarely exhibit clonality for T790M (17, 18). In vitro mechanisms of acquired gefitinib resistance do not involve secondary EGFR mutations at a significant frequency, but instead are correlated with altered receptor trafficking. However, it should be noted that we have not examined EGFR trafficking in all of the resistant clones that we established in vitro, and it remains possible that additional mechanisms may contribute to gefitinib resistance in some of the clones. Nonetheless, virtually all gefitinib-resistant clones exhibited comparable sensitivity to the irreversible ERBB inhibitors.

Our results indicate striking differences between competitive EGFR inhibitors such as gefitinib, whose effectiveness is limited by the rapid development of drug resistance in vitro, and irreversible inhibitors, to which acquired resistance appears to be rare (FIG. 2C). We speculate that increased internalization of ligand-bound EGFR in resistant cells may be linked to dissociation of the gefitinib-EGFR complex at the low pH of intracellular vesicles. In contrast, irreversible cross-linking of the receptor would be unaffected by such alterations in receptor trafficking. Acquired resistance to gefitinib is stably maintained after passage of cells for up to 20 generations in the absence of drug, suggesting that genetic or epigenetic alterations in genes that modulate EGFR turnover may underlie this phenomenon. Because receptor trafficking cannot be readily studied by using available clinical specimens, identification of such genomic alterations may be required before clinical correlations are possible. Nonetheless, such a mechanism may contribute to in vivo acquired gefitinib-resistance in patients with recurrent disease who do not have secondary mutations in EGFR.

Irreversible ERBB inhibitors also seem to be effective in overcoming gefitinib resistance mediated by the T790M mutation, an effect that presumably results from the preservation of inhibitor binding despite alteration of this critical residue. While this work was in progress, another irreversible inhibitor of EGFR [CL-387,785, Calbiochem (27)] was shown to inhibit the kinase activity of the T790M EGFR mutant (17). The effectiveness of CL-387,785 in the context of T790M was proposed to result from the absence of a chloride at position 3 of the aniline group, which is present in gefitinib and was postulated to interfere sterically with binding to the mutant methionine at codon 790. However, EKB-569, HKI-272, and HKI-357 all have chloride moieties at that position in the aniline ring, suggesting that their shared ability to bind irreversibly to EGFR is likely to explain their effectiveness, rather than the absence of a specific steric interaction with T790M (24-26). Thus, these irreversible inhibitors may prove to be broadly effective in circumventing a variety of resistance mechanisms, in addition to the T790M mutation.

TABLE 1

Presence of EGFR T790M mutation at very tow frequency in recurrent tumors from case 2

| Tumor | No. of clones | |
| --- | --- | --- |
| | T790M mutant | Wild type |
| Primary | 0 | 75 |
| Recurrent 1 | 2 | 48 |
| Recurrent 2 | 1 | 55 |
| Recurrent 3 | 0 | 55 |
| Recurrent 4 | 0 | 59 |

Sequencing of large numbers of cloned PCR products revealed that a minority of alleles within two of four liver lesions contain the T790M mutation.

The references cited throughout the application are incorporated herein by reference in their entirety.

REFERENCES

1. Schiller J H, Harrington D, Belani C P, et al. Comparison of four chemotherapy regimens for advanced non-small cell lung cancer. N Engl J Med 2002; 346:92-98.

2. Druker B J, Talpaz M, Resta D J et al. Efficacy and safety of a specific inhibitor of the BCR-ABL tyrosine kinase in Chronic Myeloid Leukemia. N Engl J Med 2001; 344:1031-1037.
3. Arteaga C L. ErhB-targeted therapeutic approaches in human cancer. Exp Cell Res. 2003; 284:122-30.
4. Jorissen R N, Walker F, Pouliot N, Garrett T P, Ward C W, Burgess A W. Epidermal growth faiotor receptor: mechanisms of activation and signaling. Exp Cell Res 2003; 284:31-53
5. Luetteke N C, Phillips H K, Qui T H, Copeland N O, Earp H S, Jenkins N A, Lee D C. The mouse waved-2 phenotype results from a point mutation in the EGF receptor tyrosine kinase. Genes Dev 1994; 8:399-413.
6. Nicholson R I, Gee J M W, Harper M E. EGFR and cancer prognosis. Eur J Cancer. 2001; 37:S9-15
7. Wong A J, Ruppert J M, Bigner S H, et al. Structural alterations of the epidermal growth factor receptor gene in human gliomas. Proc Natl Acad Sci. 1992; 89:2965-2969.
8. Ciesiciski M J, Genstermaker R A. Oncogenic epidermal growth factor receptor mutants with tandem duplication: gene structure and effects on receptor function. Oncogene 2000; 19:810-820.
9. Frederick L, Wang W-Y, Eley G, James C D. Diversity and frequency of epidermal growth factor receptor mutations in human glioblastomas. Cancer Res 2000; 60:1383-1387.
10. Huang H-J S, Nagane M. Klingbeil C K, et al. The enhanced tumorigenic activity of a mutant epidermal growth factor receptor common in human cancers is mediated by threshold levels of constitutive tyrosine phophorylation and unattenuated signaling. J Biol Chem 1997; 272:2927-2935
11. Pegram M D, Konecny G, Slamon D J. The molecular and cellular biology of HER2/neu gene amplification/overexpression and the clinical development of herceptin (trastuzumab) therapy for breast cancer. Cancer Treat Res 2000; 103:57-75.
12. Ciardiello F, Tortora G. A novel approach in the treatment of cancer targeting the epidermal growth factor receptor. Clin Cancer Res. 2001; 7:2958-2970
13. Wakeling A E, Guy S P, Woodburn J R et al. ZD1839 (Iressa): An orally active inhibitor of Epidermal Growth Factor signaling with potential for cancer therapy. Cancer Res 2002; 62:5749-5754.
14. Moulder S L, Yakes F M, Muthuswamy S K, Bianco R, Simpson J F, Arteaga C L. Epidermal growth factor receptor (HER1) tyrosine kinase inhibitor ZD1839 (Iressa) inhibits HER2/neu (erbB2)-overexpressing breast cancer cells in vitro and in vivo. Cancer Res 2001; 61:8887-8895.
15. Moasser M M, Basso A, Averbuch S D, Rosen N. The tyrosine kinase inhibitor ZD1839 ("Iressa") inhibits HER2-driven signaling and suppresses the growth of HER-2 overexpressing tumor cells. Cancer Res 2001; 61:7184-7188.
16. Ranson M, Hammond L A, Ferry D, et al. ZD1839, a selective oral epidermal growth factor receptor-tyrosine kinase inhibitor, is well tolerated and active in patients with solid, malignant tumors: results of a phase I trial. J Clin Oncol. 2002; 20: 2240-2250.
17. Herbst R S, Maddox A-M, Rothernberg M L, et al. Selective oral epidermal growth factor receptor tyrosine kinase inhibitor ZD1839 is generally well tolerated and has activity in non-small cell lung cancer and other solid tumors: results of a phase I trial. J Clin Oncol. 2002; 20:3815-3825.
18. Baselga J, Rischin J B, Ranson M, et al. Phase I safety, pharmacokinetic and pharmacodynamic trial of ZD1839, a selective oral Epidermal Growth Factor Receptor tyrosine kinase inhibitor, in patients with five selected solid tumor types. J Clin One 2002; 20:4292-4302.
19. Albanell J, Rojo F, Averbuch S, et al. Pharmacodynamic studies of the epidermal growth factor receptor inhibitor ZD1839 in skin from cancer patients: histopathologic and molecular consequences of receptor inhibition. J Clin Oncol. 2001; 20:110-124.
20. Kris M G, Natale R B, Herbst R S, et al. Efficacy of Gefitinib, an inhibitor of the epidermal growth factor receptor tyrosine kinase, in symptomatic patients with non-small cell lung cancer: A randomized trial. JAMA 2003; 290:2149-2158.
21. Fukuoka M, Yano S, Giaccone G, et al. Multi-institutional randomized phase II trial of gefitinib for previously treated patients with advanced non-small-cell lung cancer. J Clin Oncol 2003; 21:2237-2246.
22. Giaccone G, Herbst R S, Manegold C, et al. Gefitinib in combination with gemcitabine and cisplatin in advanced non-small-cell lung cancer: A phase III trial-INTACT 1. J Clin Oncol 2004; 22:777-784.
23. Herbst R S, Giaccone G, Schiller J H, et al. Gefitinib in combination with paclitaxel and carboplatin in advanced non-small-cell lung cancer: A phase III trial—INTACT 2. J Clin Oncol 2004; 22:785-794.
24. Rich J N, Reardon D A, Peery T, et al. Phase II Trial of Gefitinib in recurrent glioblastoma. J Clin Oncol 2004; 22:133-142
25. Cohen M H, Williams G A, Sridhara R, et al. United States Food and Drug Administration Drug Approval Summary: Gefitinib (ZD1839; Iressa) Tablets. Clin Cancer Res. 2004; 10:1212-1218.
26. Cappuzzo F, Gregorc V, Rossi E, et al. Gefitinib in pretreated non-small-cell lung cancer (NSCLC): Analysis of efficacy and correlation with HER2 and epidermal growth factor receptor expression in locally advanced or Metastatic NSCLC. J Clin Oncol. 2003; 21:2658-2663.
27. Fitch K R, McGowan K A, van Raamsdonk C D, et al. Genetics of Dark Skin in mice. Genes & Dev 2003; 17:214-228.
28. Nielsen U B, Cardone M H I, Sinskey A J, MacBeath G, Sorger P K. Profiling receptor tyrosine kinase activation by using Ab microarrays. Proc Natl Acad Sci USA 2003; 100:9330-5.
29. Burgess A W, Cho H, Eigenbrot C, et al. An open-and-shut case?Recent insights into the activation of EGF/ErbB receptors. Mol Cell 2003; 12:541-552.
30. Stamos J, Sliwkowski M X, Eigenbrot C. Structure of the epidermal growth factor receptor kinase domain alone and in complex with a 4-anilinoquinazoline inhibitor. J Biol Chem. 2002; 277:46265-46272.
31. Lorenzato A, Olivero M, Patrane S, et al. Novel somatic mutations of the MET oncogene in human carcinoma metastases activating cell motility and invasion. Cancer Res 2002; 62:7025-30.
32. Davies H, Bignell G R, Cox C, et al. Mutations of the BRAF gene in human cancer. Nature 2002; 417:906-7.
33. Bardelli A, Parsons D W, Silliman N, et al. Mutational analysis of the tyrosine kinome in colorectal cancers. Science 2003; 300:949.
34. Daley G Q, Van Etten R A, Baltimore D. Induction of chronic myelogenous leukemia in mice by the P210ber/abl gene of the Philadelphia chromosome. Science 1990; 247:824-30.

35. Heinrich, M C, Corless C L, Demetri G D, et al. Kinase mutations and imatinib response in patients with metastatic gastrointestinal stromal tumor. J Clin Oncol 2003; 21:4342-4349.

36. Li B, Chang C, Yuan M, McKenna W G, Shu H G. Resistance to small molecule inhibitors of epidermal growth factor receptor in malignant gliomas. Cancer Res 2003; 63:7443-7450.

The invention claimed is:

1. A method of treating gefitinib and/or erlotinib resistant non-small cell lung cancer having a T790M mutation in SEQ ID NO: 1 in a patient, comprising administering daily to the patient having gefitinib and/or erlotinib resistant non-small cell lung cancer having a T790M mutation in SEQ ID NO: 1 a pharmaceutical composition comprising a unit dosage of 2-500 mg of an irreversible EGFR inhibitor that covalently binds to cysteine 773 of the catalytic domain within the SEQ ID NO: 1 having a T790M mutation; wherein the irreversible EGFR inhibitor is not CL-387, 785.

2. The method of claim 1, wherein the irreversible EGFR inhibitor is selected from the group consisting of EKB-569, HKI-272 and HKI-357.

3. The method of claim 1, wherein the irreversible EGFR inhibitor is HKI-272.

4. The method of claim 1, wherein the irreversible EGFR inhibitor covalently binds to cysteine 805 in the ligand-binding pocket of ERBB2.

* * * * *

```
                         SEQUENCE LISTING

<160> NUMBER OF SEQ ID NOS: 5

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335
```

-continued

```
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
        370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
```

```
                755                 760                 765
Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
                930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
                980                 985                 990

Thr Asp Ser Asn Phe Tyr Arg Ala Leu Met Asp Glu Glu Asp Met Asp
                995                 1000                1005

Asp Val Val Asp Ala Asp Glu Tyr Leu Ile Pro Gln Gln Gly Phe Phe
1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
                1060                1065                1070

Pro Thr Gly Ala Leu Thr Glu Asp Ser Ile Asp Asp Thr Phe Leu Pro
                1075                1080                1085

Val Pro Glu Tyr Ile Asn Gln Ser Val Pro Lys Arg Pro Ala Gly Ser
                1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
                1140                1145                1150

Ser Pro Ala His Trp Ala Gln Lys Gly Ser His Gln Ile Ser Leu Asp
                1155                1160                1165

Asn Pro Asp Tyr Gln Gln Asp Phe Phe Pro Lys Glu Ala Lys Pro Asn
                1170                1175                1180
```

```
Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
            1205                1210

<210> SEQ ID NO 2
<211> LENGTH: 3878
<212> TYPE: DNA
<213> ORGANISM: Homo sapiens
<220> FEATURE:
<221> NAME/KEY: CDS
<222> LOCATION: (246)..(3875)

<400> SEQUENCE: 2
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240 cagcg atg cga ccc tcc ggg acg gcc ggg gca gcg ctc ctg gcg ctg ctg    290
      Met Arg Pro Ser Gly Thr Ala Gly Ala Ala Leu Leu Ala Leu Leu
      1               5                   10                  15 gct gcg ctc tgc ccg gcg agt cgg gct ctg gag gaa aag aaa gtt tgc      338
Ala Ala Leu Cys Pro Ala Ser Arg Ala Leu Glu Glu Lys Lys Val Cys
            20                  25                  30 caa ggc acg agt aac aag ctc acg cag ttg ggc act ttt gaa gat cat      386
Gln Gly Thr Ser Asn Lys Leu Thr Gln Leu Gly Thr Phe Glu Asp His
        35                  40                  45 ttt ctc agc ctc cag agg atg ttc aat aac tgt gag gtg gtc ctt ggg      434
Phe Leu Ser Leu Gln Arg Met Phe Asn Asn Cys Glu Val Val Leu Gly
    50                  55                  60 aat ttg gaa att acc tat gtg cag agg aat tat gat ctt tcc ttc tta      482
Asn Leu Glu Ile Thr Tyr Val Gln Arg Asn Tyr Asp Leu Ser Phe Leu
65                  70                  75 aag acc atc cag gag gtg gct ggt tat gtc ctc att gcc ctc aac aca      530
Lys Thr Ile Gln Glu Val Ala Gly Tyr Val Leu Ile Ala Leu Asn Thr
80                  85                  90                  95 gtg gag cga att cct ttg gaa aac ctg cag atc atc aga gga aat atg      578
Val Glu Arg Ile Pro Leu Glu Asn Leu Gln Ile Ile Arg Gly Asn Met
                100                 105                 110 tac tac gaa aat tcc tat gcc tta gca gtc tta tct aac tat gat gca      626
Tyr Tyr Glu Asn Ser Tyr Ala Leu Ala Val Leu Ser Asn Tyr Asp Ala
            115                 120                 125 aat aaa acc gga ctg aag gag ctg ccc atg aga aat tta cag gaa atc      674
Asn Lys Thr Gly Leu Lys Glu Leu Pro Met Arg Asn Leu Gln Glu Ile
        130                 135                 140 ctg cat ggc gcc gtg cgg ttc agc aac aac cct gcc ctg tgc aac gtg      722
Leu His Gly Ala Val Arg Phe Ser Asn Asn Pro Ala Leu Cys Asn Val
    145                 150                 155 gag agc atc cag tgg cgg gac ata gtc agc agt gac ttt ctc agc aac      770
Glu Ser Ile Gln Trp Arg Asp Ile Val Ser Ser Asp Phe Leu Ser Asn
160                 165                 170                 175 atg tcg atg gac ttc cag aac cac ctg ggc agc tgc caa aag tgt gat      818
Met Ser Met Asp Phe Gln Asn His Leu Gly Ser Cys Gln Lys Cys Asp
                180                 185                 190 cca agc tgt ccc aat ggg agc tgc tgg ggt gca gga gag gag aac tgc      866
Pro Ser Cys Pro Asn Gly Ser Cys Trp Gly Ala Gly Glu Glu Asn Cys
            195                 200                 205 cag aaa ctg acc aaa atc atc tgt gcc cag cag tgc tcc ggg cgc tgc      914
```

```
                    Gln Lys Leu Thr Lys Ile Ile Cys Ala Gln Gln Cys Ser Gly Arg Cys
                                210                 215                 220 cgt ggc aag tcc ccc agt gac tgc tgc cac aac cag tgt gct gca ggc              962
Arg Gly Lys Ser Pro Ser Asp Cys Cys His Asn Gln Cys Ala Ala Gly
            225                 230                 235 tgc aca ggc ccc cgg gag agc gac tgc ctg gtc tgc cgc aaa ttc cga             1010
Cys Thr Gly Pro Arg Glu Ser Asp Cys Leu Val Cys Arg Lys Phe Arg
240                 245                 250                 255 gac gaa gcc acg tgc aag gac acc tgc ccc cca ctc atg ctc tac aac             1058
Asp Glu Ala Thr Cys Lys Asp Thr Cys Pro Pro Leu Met Leu Tyr Asn
                260                 265                 270 ccc acc acg tac cag atg gat gtg aac ccc gag ggc aaa tac agc ttt             1106
Pro Thr Thr Tyr Gln Met Asp Val Asn Pro Glu Gly Lys Tyr Ser Phe
            275                 280                 285 ggt gcc acc tgc gtg aag aag tgt ccc cgt aat tat gtg gtg aca gat             1154
Gly Ala Thr Cys Val Lys Lys Cys Pro Arg Asn Tyr Val Val Thr Asp
290                 295                 300 cac ggc tcg tgc gtc cga gcc tgt ggg gcc gac agc tat gag atg gag             1202
His Gly Ser Cys Val Arg Ala Cys Gly Ala Asp Ser Tyr Glu Met Glu
305                 310                 315 gaa gac ggc gtc cgc aag tgt aag aag tgc gaa ggg cct tgc cgc aaa             1250
Glu Asp Gly Val Arg Lys Cys Lys Lys Cys Glu Gly Pro Cys Arg Lys
320                 325                 330                 335 gtg tgt aac gga ata ggt att ggt gaa ttt aaa gac tca ctc tcc ata             1298
Val Cys Asn Gly Ile Gly Ile Gly Glu Phe Lys Asp Ser Leu Ser Ile
                340                 345                 350 aat gct acg aat att aaa cac ttc aaa aac tgc acc tcc atc agt ggc             1346
Asn Ala Thr Asn Ile Lys His Phe Lys Asn Cys Thr Ser Ile Ser Gly
            355                 360                 365 gat ctc cac atc ctg ccg gtg gca ttt agg ggt gac tcc ttc aca cat             1394
Asp Leu His Ile Leu Pro Val Ala Phe Arg Gly Asp Ser Phe Thr His
370                 375                 380 act cct cct ctg gat cca cag gaa ctg gat att ctg aaa acc gta aag             1442
Thr Pro Pro Leu Asp Pro Gln Glu Leu Asp Ile Leu Lys Thr Val Lys
385                 390                 395 gaa atc aca ggg ttt ttg ctg att cag gct tgg cct gaa aac agg acg             1490
Glu Ile Thr Gly Phe Leu Leu Ile Gln Ala Trp Pro Glu Asn Arg Thr
400                 405                 410                 415 gac ctc cat gcc ttt gag aac cta gaa atc ata cgc ggc agg acc aag             1538
Asp Leu His Ala Phe Glu Asn Leu Glu Ile Ile Arg Gly Arg Thr Lys
                420                 425                 430 caa cat ggt cag ttt tct ctt gca gtc gtc agc ctg aac ata aca tcc             1586
Gln His Gly Gln Phe Ser Leu Ala Val Val Ser Leu Asn Ile Thr Ser
            435                 440                 445 ttg gga tta cgc tcc ctc aag gag ata agt gat gga gat gtg ata att             1634
Leu Gly Leu Arg Ser Leu Lys Glu Ile Ser Asp Gly Asp Val Ile Ile
450                 455                 460 tca gga aac aaa aat ttg tgc tat gca aat aca ata aac tgg aaa aaa             1682
Ser Gly Asn Lys Asn Leu Cys Tyr Ala Asn Thr Ile Asn Trp Lys Lys
465                 470                 475 ctg ttt ggg acc tcc ggt cag aaa acc aaa att ata agc aac aga ggt             1730
Leu Phe Gly Thr Ser Gly Gln Lys Thr Lys Ile Ile Ser Asn Arg Gly
480                 485                 490                 495 gaa aac agc tgc aag gcc aca ggc cag gtc tgc cat gcc ttg tgc tcc             1778
Glu Asn Ser Cys Lys Ala Thr Gly Gln Val Cys His Ala Leu Cys Ser
                500                 505                 510 ccc gag ggc tgc tgg ggc ccg gag ccc agg gac tgc gtc tct tgc cgg             1826
Pro Glu Gly Cys Trp Gly Pro Glu Pro Arg Asp Cys Val Ser Cys Arg
            515                 520                 525
```

-continued

| | | |
|---|---|---|
| aat gtc agc cga ggc agg gaa tgc gtg gac aag tgc aac ctt ctg gag<br>Asn Val Ser Arg Gly Arg Glu Cys Val Asp Lys Cys Asn Leu Leu Glu<br>530 535 540 | | 1874 |
| ggt gag cca agg gag ttt gtg gag aac tct gag tgc ata cag tgc cac<br>Gly Glu Pro Arg Glu Phe Val Glu Asn Ser Glu Cys Ile Gln Cys His<br>545 550 555 | | 1922 |
| cca gag tgc ctg cct cag gcc atg aac atc acc tgc aca gga cgg gga<br>Pro Glu Cys Leu Pro Gln Ala Met Asn Ile Thr Cys Thr Gly Arg Gly<br>560 565 570 575 | | 1970 |
| cca gac aac tgt atc cag tgt gcc cac tac att gac ggc ccc cac tgc<br>Pro Asp Asn Cys Ile Gln Cys Ala His Tyr Ile Asp Gly Pro His Cys<br>580 585 590 | | 2018 |
| gtc aag acc tgc ccg gca gga gtc atg gga gaa aac aac acc ctg gtc<br>Val Lys Thr Cys Pro Ala Gly Val Met Gly Glu Asn Asn Thr Leu Val<br>595 600 605 | | 2066 |
| tgg aag tac gca gac gcc ggc cat gtg tgc cac ctg tgc cat cca aac<br>Trp Lys Tyr Ala Asp Ala Gly His Val Cys His Leu Cys His Pro Asn<br>610 615 620 | | 2114 |
| tgc acc tac gga tgc act ggg cca ggt ctt gaa ggc tgt cca acg aat<br>Cys Thr Tyr Gly Cys Thr Gly Pro Gly Leu Glu Gly Cys Pro Thr Asn<br>625 630 635 | | 2162 |
| ggg cct aag atc ccg tcc atc gcc act ggg atg gtg ggg gcc ctc ctc<br>Gly Pro Lys Ile Pro Ser Ile Ala Thr Gly Met Val Gly Ala Leu Leu<br>640 645 650 655 | | 2210 |
| ttg ctg ctg gtg gtg gcc ctg ggg atc ggc ctc ttc atg cga agg cgc<br>Leu Leu Leu Val Val Ala Leu Gly Ile Gly Leu Phe Met Arg Arg Arg<br>660 665 670 | | 2258 |
| cac atc gtt cgg aag cgc acg ctg cgg agg ctg ctg cag gag agg gag<br>His Ile Val Arg Lys Arg Thr Leu Arg Arg Leu Leu Gln Glu Arg Glu<br>675 680 685 | | 2306 |
| ctt gtg gag cct ctt aca ccc agt gga gaa gct ccc aac caa gct ctc<br>Leu Val Glu Pro Leu Thr Pro Ser Gly Glu Ala Pro Asn Gln Ala Leu<br>690 695 700 | | 2354 |
| ttg agg atc ttg aag gaa act gaa ttc aaa aag atc aaa gtg ctg ggc<br>Leu Arg Ile Leu Lys Glu Thr Glu Phe Lys Lys Ile Lys Val Leu Gly<br>705 710 715 | | 2402 |
| tcc ggt gcg ttc ggc acg gtg tat aag gga ctc tgg atc cca gaa ggt<br>Ser Gly Ala Phe Gly Thr Val Tyr Lys Gly Leu Trp Ile Pro Glu Gly<br>720 725 730 735 | | 2450 |
| gag aaa gtt aaa att ccc gtc gct atc aag gaa tta aga gaa gca aca<br>Glu Lys Val Lys Ile Pro Val Ala Ile Lys Glu Leu Arg Glu Ala Thr<br>740 745 750 | | 2498 |
| tct ccg aaa gcc aac aag gaa atc ctc gat gaa gcc tac gtg atg gcc<br>Ser Pro Lys Ala Asn Lys Glu Ile Leu Asp Glu Ala Tyr Val Met Ala<br>755 760 765 | | 2546 |
| agc gtg gac aac ccc cac gtg tgc cgc ctg ctg ggc atc tgc ctc acc<br>Ser Val Asp Asn Pro His Val Cys Arg Leu Leu Gly Ile Cys Leu Thr<br>770 775 780 | | 2594 |
| tcc acc gtg cag ctc atc acg cag ctc atg ccc ttc ggc tgc ctc ctg<br>Ser Thr Val Gln Leu Ile Thr Gln Leu Met Pro Phe Gly Cys Leu Leu<br>785 790 795 | | 2642 |
| gac tat gtc cgg gaa cac aaa gac aat att ggc tcc cag tac ctg ctc<br>Asp Tyr Val Arg Glu His Lys Asp Asn Ile Gly Ser Gln Tyr Leu Leu<br>800 805 810 815 | | 2690 |
| aac tgg tgt gtg cag atc gca aag ggc atg aac tac ttg gag gac cgt<br>Asn Trp Cys Val Gln Ile Ala Lys Gly Met Asn Tyr Leu Glu Asp Arg<br>820 825 830 | | 2738 |
| cgc ttg gtg cac cgc gac ctg gca gcc agg aac gta ctg gtg aaa aca<br>Arg Leu Val His Arg Asp Leu Ala Ala Arg Asn Val Leu Val Lys Thr<br>835 840 845 | | 2786 |

-continued

| | |
|---|---|
| ccg cag cat gtc aag atc aca gat ttt ggg ctg gcc aaa ctg ctg ggt<br>Pro Gln His Val Lys Ile Thr Asp Phe Gly Leu Ala Lys Leu Leu Gly<br>850                      855                      860 | 2834 |
| gcg gaa gag aaa gaa tac cat gca gaa gga ggc aaa gtg cct atc aag<br>Ala Glu Glu Lys Glu Tyr His Ala Glu Gly Gly Lys Val Pro Ile Lys<br>865                      870                      875 | 2882 |
| tgg atg gca ttg gaa tca att tta cac aga atc tat acc cac cag agt<br>Trp Met Ala Leu Glu Ser Ile Leu His Arg Ile Tyr Thr His Gln Ser<br>880                      885                      890                      895 | 2930 |
| gat gtc tgg agc tac ggg gtg acc gtt tgg gag ttg atg acc ttt gga<br>Asp Val Trp Ser Tyr Gly Val Thr Val Trp Glu Leu Met Thr Phe Gly<br>                     900                      905                      910 | 2978 |
| tcc aag cca tat gac gga atc cct gcc agc gag atc tcc tcc atc ctg<br>Ser Lys Pro Tyr Asp Gly Ile Pro Ala Ser Glu Ile Ser Ser Ile Leu<br>                     915                      920                      925 | 3026 |
| gag aaa gga gaa cgc ctc cct cag cca ccc ata tgt acc atc gat gtc<br>Glu Lys Gly Glu Arg Leu Pro Gln Pro Pro Ile Cys Thr Ile Asp Val<br>           930                      935                      940 | 3074 |
| tac atg atc atg gtc aag tgc tgg atg ata gac gca gat agt cgc cca<br>Tyr Met Ile Met Val Lys Cys Trp Met Ile Asp Ala Asp Ser Arg Pro<br>945                      950                      955 | 3122 |
| aag ttc cgt gag ttg atc atc gaa ttc tcc aaa atg gcc cga gac ccc<br>Lys Phe Arg Glu Leu Ile Ile Glu Phe Ser Lys Met Ala Arg Asp Pro<br>960                      965                      970                      975 | 3170 |
| cag cgc tac ctt gtc att cag ggg gat gaa aga atg cat ttg cca agt<br>Gln Arg Tyr Leu Val Ile Gln Gly Asp Glu Arg Met His Leu Pro Ser<br>                     980                      985                      990 | 3218 |
| cct aca gac tcc aac ttc tac cgt gcc ctg atg gat gaa gaa gac atg<br>Pro Thr Asp Ser Asn Phe Tyr Arg Ala Leu Met Asp Glu Glu Asp Met<br>                     995                      1000                      1005 | 3266 |
| gac gac gtg gtg gat gcc gac gag tac ctc atc cca cag cag ggc ttc<br>Asp Asp Val Val Asp Ala Asp Glu Tyr Leu Ile Pro Gln Gln Gly Phe<br>           1010                      1015                      1020 | 3314 |
| ttc agc agc ccc tcc acg tca cgg act ccc ctg ctg agc tct ctg agt<br>Phe Ser Ser Pro Ser Thr Ser Arg Thr Pro Leu Leu Ser Ser Leu Ser<br>1025                      1030                      1035 | 3362 |
| gca acc agc aac aat tcc acc gtg gct tgc att gat aga aat ggg ctg<br>Ala Thr Ser Asn Asn Ser Thr Val Ala Cys Ile Asp Arg Asn Gly Leu<br>1040                      1045                      1050                      1055 | 3410 |
| caa agc tgt ccc atc aag gaa gac agc ttc ttg cag cga tac agc tca<br>Gln Ser Cys Pro Ile Lys Glu Asp Ser Phe Leu Gln Arg Tyr Ser Ser<br>           1060                      1065                      1070 | 3458 |
| gac ccc aca ggc gcc ttg act gag gac agc ata gac gac acc ttc ctc<br>Asp Pro Thr Gly Ala Leu Thr Glu Asp Ser Ile Asp Asp Thr Phe Leu<br>                     1075                      1080                      1085 | 3506 |
| cca gtg cct gaa tac ata aac cag tcc gtt ccc aaa agg ccc gct ggc<br>Pro Val Pro Glu Tyr Ile Asn Gln Ser Val Pro Lys Arg Pro Ala Gly<br>           1090                      1095                      1100 | 3554 |
| tct gtg cag aat cct gtc tat cac aat cag cct ctg aac ccc gcg ccc<br>Ser Val Gln Asn Pro Val Tyr His Asn Gln Pro Leu Asn Pro Ala Pro<br>1105                      1110                      1115 | 3602 |
| agc aga gac cca cac tac cag gac ccc cac agc act gca gtg ggc aac<br>Ser Arg Asp Pro His Tyr Gln Asp Pro His Ser Thr Ala Val Gly Asn<br>1120                      1125                      1130                      1135 | 3650 |
| ccc gag tat ctc aac act gtc cag ccc acc tgt gtc aac agc aca ttc<br>Pro Glu Tyr Leu Asn Thr Val Gln Pro Thr Cys Val Asn Ser Thr Phe<br>                     1140                      1145                      1150 | 3698 |
| gac agc cct gcc cac tgg gcc cag aaa ggc agc cac caa att agc ctg<br>Asp Ser Pro Ala His Trp Ala Gln Lys Gly Ser His Gln Ile Ser Leu | 3746 |

```
                    1155                1160                1165
gac aac cct gac tac cag cag gac ttc ttt ccc aag gaa gcc aag cca    3794
Asp Asn Pro Asp Tyr Gln Gln Asp Phe Phe Pro Lys Glu Ala Lys Pro
        1170                1175                1180 aat ggc atc ttt aag ggc tcc aca gct gaa aat gca gaa tac cta agg    3842
Asn Gly Ile Phe Lys Gly Ser Thr Ala Glu Asn Ala Glu Tyr Leu Arg
    1185                1190                1195 gtc gcg cca caa agc agt gaa ttt att gga gca tga                    3878
Val Ala Pro Gln Ser Ser Glu Phe Ile Gly Ala
1200                1205                1210

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgcarctcat cacgca                                                      16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgcarctcat caygca                                                      16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgcaactcat catgca                                                      16
```